US012766134B2

(12) United States Patent
Stauffer et al.

(10) Patent No.: US 12,766,134 B2
(45) Date of Patent: Oct. 20, 2026

(54) PROTEASE INHIBITORS AND METHODS OF USE

(71) Applicant: The Cleveland Clinic Foundation, Cleveland, OH (US)

(72) Inventors: Shaun R. Stauffer, Cleveland, OH (US); Jonathan D. Macdonald, Cleveland, OH (US); Alice Hooper, Cleveland, OH (US); Sang Hoon Han, Cleveland, OH (US); Dhiraj P. Sonawane, Cleveland, OH (US); Matthew R. Porter, Cleveland, OH (US); Joshua Maw, Cleveland, OH (US); Steven Martinez, Cleveland, OH (US); Joseph Alvarado, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 365 days.

(21) Appl. No.: 18/570,520

(22) PCT Filed: Jun. 16, 2022

(86) PCT No.: PCT/US2022/033861

§ 371 (c)(1),
(2) Date: Dec. 14, 2023

(87) PCT Pub. No.: WO2022/266368

PCT Pub. Date: Dec. 22, 2022

(65) Prior Publication Data

US 2024/0293380 A1 Sep. 5, 2024

Related U.S. Application Data

(60) Provisional application No. 63/211,084, filed on Jun. 16, 2021.

(51) Int. Cl.

| | |
|---|---|
| ***C07D 217/16*** | (2006.01) |
| ***A61K 31/423*** | (2006.01) |
| ***A61K 31/437*** | (2006.01) |
| ***A61K 31/4439*** | (2006.01) |
| ***A61K 31/444*** | (2006.01) |
| ***A61K 31/4725*** | (2006.01) |
| ***A61K 31/496*** | (2006.01) |
| ***A61K 31/497*** | (2006.01) |
| ***A61K 31/498*** | (2006.01) |
| ***A61K 31/501*** | (2006.01) |
| ***A61K 31/502*** | (2006.01) |
| ***A61K 31/5025*** | (2006.01) |
| ***A61P 31/14*** | (2006.01) |
| ***C07D 401/12*** | (2006.01) |
| ***C07D 401/14*** | (2006.01) |
| ***C07D 403/12*** | (2006.01) |
| ***C07D 413/12*** | (2006.01) |
| ***C07D 471/04*** | (2006.01) |
| ***C07D 487/04*** | (2006.01) |

(52) U.S. Cl.

CPC .......... *A61K 31/437* (2013.01); *A61K 31/423* (2013.01); *A61K 31/4439* (2013.01); *A61K 31/444* (2013.01); *A61K 31/4725* (2013.01); *A61K 31/496* (2013.01); *A61K 31/497* (2013.01); *A61K 31/498* (2013.01); *A61K 31/501* (2013.01); *A61K 31/502* (2013.01); *A61K 31/5025* (2013.01); *A61P 31/14* (2018.01); *C07D 217/16* (2013.01); *C07D 401/12* (2013.01); *C07D 401/14* (2013.01); *C07D 403/12* (2013.01); *C07D 413/12* (2013.01); *C07D 471/04* (2013.01); *C07D 487/04* (2013.01)

(58) Field of Classification Search

CPC .............. A61K 31/437; A61K 31/4439; A61K 31/444; A61K 31/4725; A61K 31/496; A61K 31/497; A61K 31/498; A61K 31/501; A61K 31/502; A61K 31/5025; A61P 31/14; C07D 217/16; C07D 401/12; C07D 403/12; C07D 413/12; C07D 471/04; C07D 487/04

See application file for complete search history.

(56) References Cited

U.S. PATENT DOCUMENTS

| | | | | |
|---|---|---|---|---|
| 5,033,252 | A | 7/1991 | Carter | |
| 5,052,558 | A | 10/1991 | Carter | |
| 5,323,907 | A | 6/1994 | Kalvelage | |
| 9,975,885 | B2 | 5/2018 | St et al. | |
| 2024/0239772 | A1* | 7/2024 | Stauffer ............... | A61K 31/496 |

FOREIGN PATENT DOCUMENTS

| | | | |
|---|---|---|---|
| WO | WO-2005121095 | A1 | 12/2005 |
| WO | WO-2020214858 | A1 | 10/2020 |

OTHER PUBLICATIONS

CAS Registry No. 2637061-41-5 (Apr. 23, 2021) (Year: 2021).*
Tintori et al. (Bioorganic & Medicinal Chemistry Letters 2014; 24:280-282, including Supplemental data) (Year: 2014).*
International Search Report and Written Opinion for International Application No. PCT/US2022/033861, mailed Oct. 25, 2022, 12 Pages.
Jacobs J., et al., "Discovery, Synthesis, And Structure-Based Optimization of a Series of N-(tert-Butyl)-2-(N-arylamido)-2-(pyridin-3-yl) Acetamides (ML188) as Potent Noncovalent Small Molecule Inhibitors of the Severe Acute Respiratory Syndrome Coronavirus (SARS-CoV) 3CL Protease," Journal of Medicinal Chemistry, Jan. 24, 2013, vol. 56, No. 02, pp. 534-546 (Year: 2013).

(Continued)

*Primary Examiner* — Brandon J Fetterolf
(74) *Attorney, Agent, or Firm* — Casimir Jones, S.C.; Anne M. Reynolds

(57) ABSTRACT

Disclosed herein are compounds that inhibit the 3C-like protease of SARS-CoV-2. Also disclosed herein are pharmaceutical compositions comprising the compounds, and methods of using the compounds, e.g., in a method of treating a viral infection, such as a coronavirus infection.

19 Claims, No Drawings

(56) References Cited

OTHER PUBLICATIONS

Jin Z., et al., "Structure of $M^{pro}$ from COVID-19 Virus and Discovery of its Inhibitors," Nature, Apr. 9, 2020, vol. 582, No. 7811, pp. 289-293.
John S., et al., "Targeting Zoonotic Viruses: Structure-based Inhibition of the 3c-like Protease From Bat Coronavirus Hku4—the Likely Reservoir Host to the Human Coronavirus That Causes Middle East Respiratory Syndrome (MERS)," Bioorganic and Medicinal Chemistry, Sep. 1, 2015, vol. 23, No. 17, pp. 1-30, DOI: 10.1016/j.bmc.2015.06.039, XP055826372.
Nasoff M.S., et al., "Identification of an immunodominant Epitope within the Capsid Protein of Hepatitis C Virus", Proceedings of the National Academy of Sciences, Jun. 1991, vol. 88, No. 12, pp. 5462-5466.
Nishioka K., eta l., "Viral Hepatitis and Liver Disease," Proceedings of the International Symposium on Viral Hepatitis and Liver Disease: Molecules Today, More Cures Tomorrow, Tokyo, May 10-14, 1993 (1993 ISVHLD), 17 pages.
Pubchem: "2-Imidazo[1,2-A]Pyridin-5-Yl-N-(4-Thiophen-2-Ylphenyl)Acetamide C19H15N3OS," Database Pubchem NCBI Database Accession No. 125473641, XP093016319.
Pubchem: "Tert-Butyl 2-[4-[[2-(Benzotriazol-1-yl)Acetyl]-(Thiophen-3-ylmethyl)Amino]Phenyl]Pyrrole-1-Carboxylate", Database Pubchem NCBI Database Accession No. 56973496, Created on Jun. 6, 2012, XP055983174, 8 Pages.
Shin W-J., et al., "Development of Thermostable Lyophilized Sabin Inactivated Poliovirus Vaccine", mBio, Nov./Dec. 2018, vol. 9, No. 6, pp. 1-13.
Shin W.J., et al., "Identification of a Small Benzamide Inhibitor of Influenza Virus Using a Cell-Based Screening", Chemotherapy, Jun. 2016, vol. 61, No. 3, pp. 159-166.
Tomar S., et al., "Ligand-Induced Dimerization of Middle East Respiratory Syndrome (MERS) Coronavirus nsp5 Protease (3CLpro)", Journal of Biological Chemistry, Aug. 7, 2015, vol. 290, No. 32, pp. 19403-19422.
Turlington M., et al., "Discovery of N-(Benzo[1,2,3]Triazol-1-yl)-N-(Benzyl)Acetamido) Phenyl) Carboxamides as Severe Acute Respiratory Syndrome Coronavirus (SARS-CoV) 3CLpro Inhibitors: Identification of ML300 and Noncovalent Nanomolar Inhibitors with an Induced-Fit Binding", Bioorganic & Medicinal Chemistry Letters, Dec. 2013, vol. 23, No. 22, pp. 6172-6177.
Turlington M., et al., "Non-covalent Triazole-based Inhibitors of the SARS main proteinase 3CLpro," Probe Reports from NIH Molecular Libraries Program, Mar. 14, 2013, pp. 1-9, XP055983176.
Wang W., et al., "The Cap-Snatching SFTSV Endonuclease Domain Is an Antiviral Target," Cell Reports, Jan. 7, 2020, vol. 30, No. 1, pp. 153-163.e5.
Xue X., et al., "Production of Authentic SARS-CoV $M^{pro}$ with Enhanced Activity: Application as a Novel Tag-Cleavage Endopeptidase for Protein Overproduction", Journal of Molecular Biology, Feb. 2007, vol. 366, No. 3, pp. 965-975, https://doi.Org/10.1016/j.jmb.2006.11.073.
Yu., et al., "Transfusion," The Journal of the American Association of Blood Banks, Jul. 1994, vol. 34, No. 07, pp. 596-602.

* cited by examiner

PROTEASE INHIBITORS AND METHODS OF USE

CROSS-REFERENCE TO RELATED APPLICATIONS

This application is a U.S. national stage filing under 35 U.S.C. § 371 of International Patent Application No. PCT/US2022/033861, which claims priority to and the benefit of U.S. Provisional Patent Application No. 63/211,084, filed on Jun. 16, 2021, each of which is incorporated herein by reference in its entirety.

TECHNICAL FIELD

Disclosed herein are compounds that inhibit the 3C-like protease of SARS-CoV-2. Also disclosed herein are pharmaceutical compositions comprising the compounds, and methods of using the compounds, e.g., in a method of treating a viral infection, such as a coronavirus infection.

BACKGROUND

Coronaviruses are enveloped, large plus-strand RNA viruses associated with mild to severe respiratory symptoms, including the common cold, Severe Acquired Respiratory Syndrome (SARS), Middle East Respiratory Syndrome (MERS), and Coronavirus Disease 2019 (COVID-19). SARS, MERS, and COVID-19 can each present an atypical pneumonia that can lead to progressive respiratory failure. Although a rigorous public healthcare campaign was successful in controlling the SARS and MERS outbreaks, the global pandemic caused by SARS-CoV-2, the causative agent of COVID-19, is ongoing.

The SARS-CoV, MERS-CoV, and SARS-CoV-2 viruses encode two proteases, a papain-like protease (PLpro) and a 3-chymotrypsin-like protease (3CLpro), which are essential for viral replication. The viral polyprotein is cleaved at three unique sites by PLpro and eleven unique sites by 3CLpro. As there is no known close human analog of these proteases, a selective inhibitor could provide a critically important therapeutic for coronaviruses while avoiding unwanted polypharmacologies. Initial reports of 3CLpro inhibitors focused on peptidomimetics bearing a reactive 'warhead' group, with several demonstrating a covalent interaction with the active site Cys-145 residue. However, although covalent protease inhibitors have been successfully launched to market, they may bring inherent risks due to the increased potential of off-target activities.

SUMMARY

In one aspect, disclosed herein is a compound of formula (I):

(I)

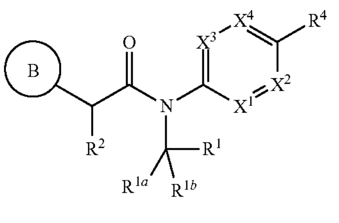

or a pharmaceutically acceptable salt thereof, wherein:

$R^1$ is selected from: aryl; a monocyclic heteroaryl having 1, 2, or 3 heteroatoms independently selected from N, O, and S; $C_3$-$C_6$ cycloalkyl; a monocyclic heterocyclyl having 1, 2, or 3 heteroatoms independently selected from N, O, and S; $C_3$-$C_6$ alkyl; and $C_1$-$C_6$ haloalkyl;

$R^{1a}$ and $R^{1b}$ are each independently selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, $C_1$-$C_3$ aminoalkyl, —CON($R^{1c}$)($R^{1d}$), and —$(CH_2)_{n1}$-$G^1$, wherein n1 is 0, 1, or 2, and wherein $G^1$ is selected from $C_3$-$C_6$ cycloalkyl, a 4- to 6-membered monocyclic heterocycle, and a 5- or 6-membered monocyclic heteroaryl; or wherein $R^{1a}$ and $R^{1b}$ are taken together with the carbon atom to which they are attached to form a $C_3$-$C_6$ cycloalkyl;

$R^{1c}$ and $R^{1d}$ are each independently selected from hydrogen, $C_1$-$C_4$ alkyl, $C_1$-$C_4$ haloalkyl, and $C_3$-$C_6$ cycloalkyl;

B is a monocyclic heteroaryl, a bicyclic heteroaryl, or a bicyclic heterocyclyl, wherein B is linked to the remainder of the molecule via a carbon atom;

$R^2$ is hydrogen or $C_1$-$C_3$ alkyl;

$X^1$ is $CR^{3a}$ or N, $X^2$ is $CR^{3b}$ or N, $X^3$ is $CR^{3c}$ or N, and $X^4$ is $CR^{3d}$ or N;

$R^{3a}$, $R^{3b}$, $R^{3c}$ and $R^{3d}$ are each independently selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —CON($R^{3g}$)($R^{3h}$), and —$(CH_2)_{n3}$-$G^3$, wherein $R^{3e}$, $R^{3f}$, $R^{3g}$, and $R^{3h}$ are each independently selected from hydrogen and $C_1$-$C_3$ alkyl, wherein n3 is 0, 1, or 2, and wherein $G^3$ is selected from $C_3$-$C_6$ cycloalkyl and a 4- to 6-membered monocyclic heterocycle;

$R^4$ is selected from: a 5-membered monocyclic heteroaryl having 1, 2, 3, or 4 heteroatoms independently selected from N, O, and S; a 5- or 6-membered heterocyclyl having 1, 2, or 3 heteroatoms independently selected from N, O, and S; cyano; —$CR^{4c}R^{4d}$—$NR^{4a}R^{4b}$, and —C(O)$NR^{4a}R^{4b}$;

$R^{4a}$ and $R^{4b}$ are each independently selected from hydrogen and $C_1$-$C_3$ alkyl; and $R^{4c}$ and $R^{4d}$ are each independently selected from hydrogen, $C_1$-$C_3$ alkyl, $C_1$-$C_3$ haloalkyl, and $C_3$-$C_6$ cycloalkyl, or $R^{4c}$ and $R^{4d}$, together with the carbon atom to which they are attached, are taken together to form a 3- to 6-membered ring;

wherein each alkyl, heteroaryl, aryl, cycloalkyl, and heterocyclyl is independently unsubstituted or substituted with 1, 2, or 3 substituents independently selected from $C_1$-$C_3$ alkyl, $C_1$-$C_3$ alkoxy, $C_1$-$C_3$ hydroxyalkyl, halo, $C_1$-$C_3$ haloalkyl, $C_1$-$C_3$ haloalkoxy, $C_3$-$C_6$ cycloalkyl, aryl, arylalkyl, amino, hydroxy, cyano, oxo, and thioxo.

In some embodiments, $R^1$ is selected from: aryl; a monocyclic heteroaryl having 1 or 2 heteroatoms independently selected from N, O, and S; $C_3$-$C_5$ cycloalkyl; a monocyclic 4- or 5-membered heterocyclyl having 1 heteroatom selected from N, O, and S; $C_3$-$C_5$ alkyl; and $C_1$-$C_2$ haloalkyl. In some embodiments, $R^1$ is selected from phenyl, pyridyl, thiophenyl, thiazolyl, cyclopropyl, cyclobutyl, cyclopentyl, oxetanyl, tetrahydrofuranyl, isobutyl, tert-butyl, and trifluoromethyl. In some embodiments, $R^1$ is phenyl or pyridyl, each of which is independently unsubstituted or substituted with 1 or 2 substituents independently selected from halo, $C_1$-$C_3$ alkyl, $C_1$-$C_3$ haloalkyl, $C_1$-$C_3$ haloalkoxy, and $C_1$-$C_3$ alkoxy. In some embodiments, $R^1$ is selected from:

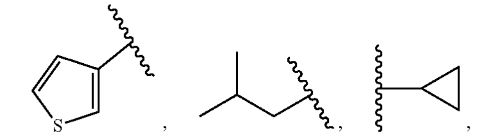
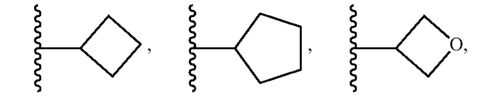
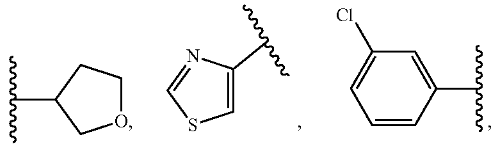
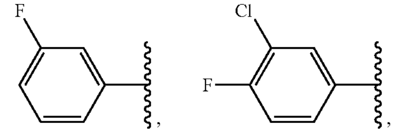
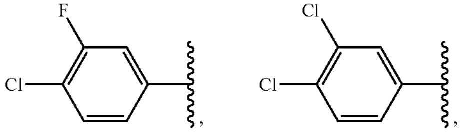
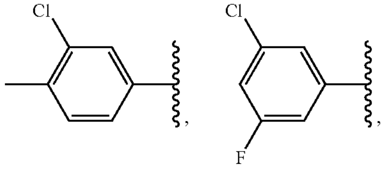
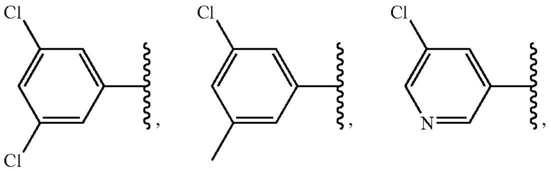
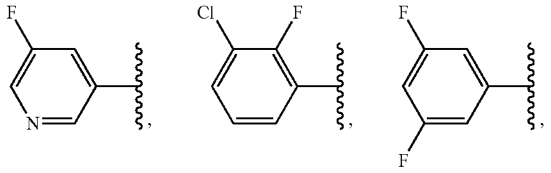
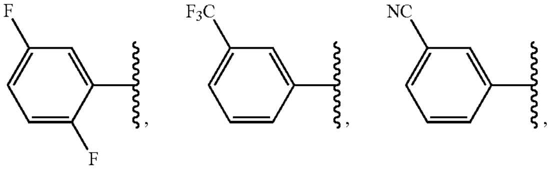
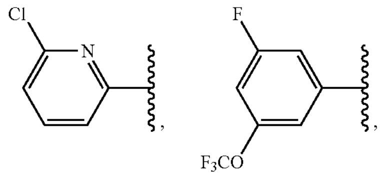
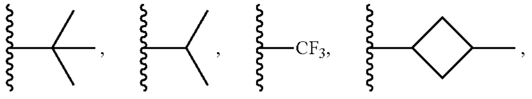
-continued
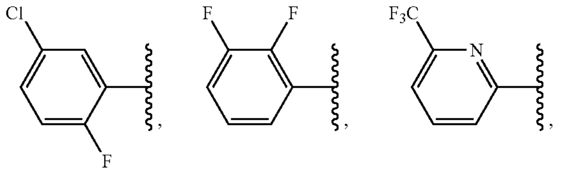
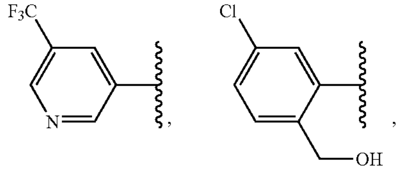
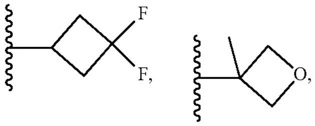
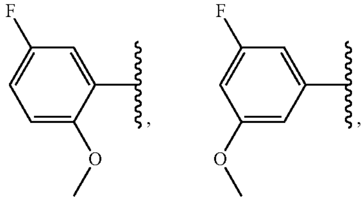
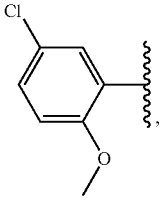
and
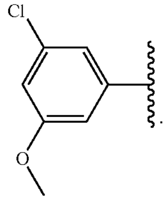
In some embodiments, $R^1$ is selected from:
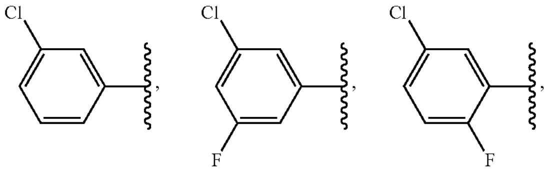
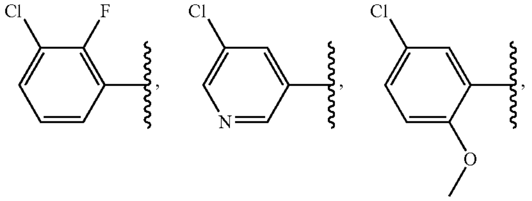
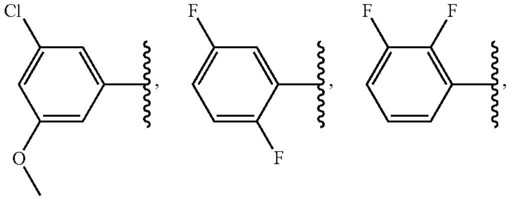
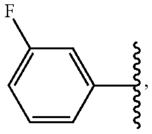

-continued

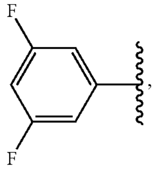, 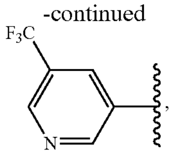, 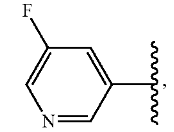, 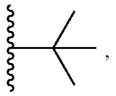, 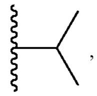, 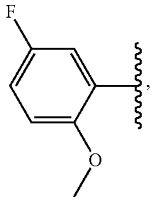, 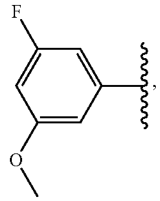, 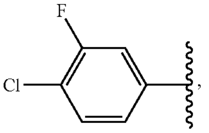, and 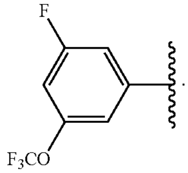.

In some embodiments, $R^{1a}$ is hydrogen and $R^{1b}$ is selected from hydrogen, $C_1$-$C_3$ alkyl, $C_1$-$C_3$ haloalkyl, $C_1$-$C_3$ hydroxyalkyl, $C_1$-$C_3$ aminoalkyl, —CON($R^{1c}$)($R^{1d}$), and —$(CH_2)_{n1}$-$G^1$. In some embodiments, $R^{1a}$ is hydrogen and $R^{1b}$ is hydrogen.

In some embodiments, B is selected from: a five-membered heteroaryl having 1, 2, 3, or 4 heteroatoms independently selected from N, O, and S; a six-membered heteroaryl having 1, 2, 3, or 4 nitrogen atoms; and an 8-10 membered bicyclic heteroaryl having 1, 2, 3, or 4 heteroatoms independently selected from N, O, and S; and an 8-10 membered bicyclic heterocyclyl having 1, 2, 3, or 4 heteroatoms independently selected from N, O, and S. In some embodiments, B is selected from pyridyl, pyridazinyl, pyrimidinyl, pyrazinyl, pyrrolyl, pyrazolyl, imidazolyl, triazolyl, tetrazolyl, oxazolyl, thiazolyl, oxadiazolyl, and thiadiazolyl, quinolinyl, isoquinolinyl, imidazopyridinyl, benzoisoxazolyl, benzoisothiazolyl, triazolopyridinyl, and isoindolinyl. In some embodiments, B is unsubstituted or substituted with 1 or 2 substituents independently selected from methyl, fluoro, chloro, bromo, trifluoromethyl, methoxy, cyclopropyl, oxo, and phenyl. In some embodiments, Bis selected from:

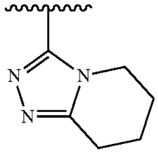, 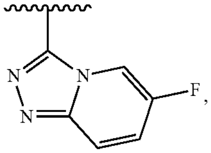, 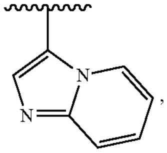, 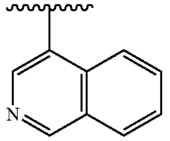, 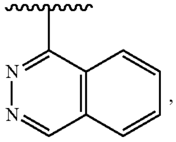, 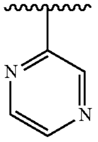, 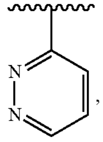, -continued

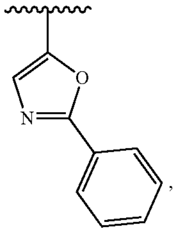, 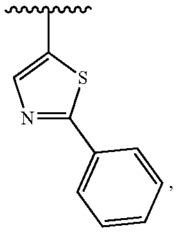, 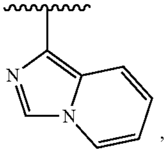, 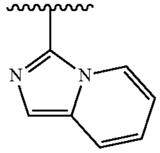, 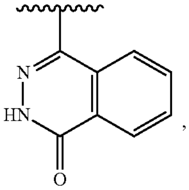, 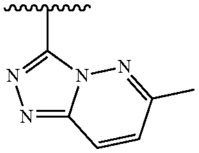, 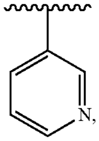 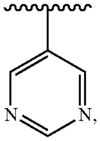 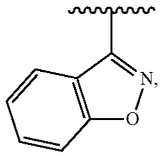 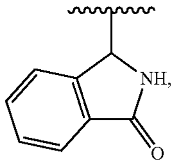 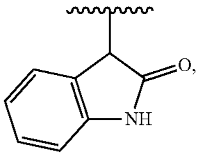 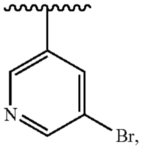 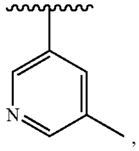, 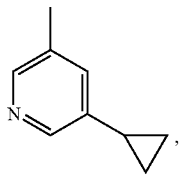, 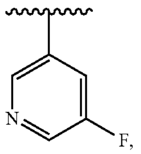 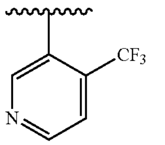, 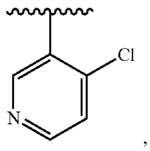, 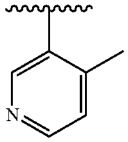, and 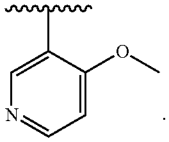.

In some embodiments. E is selected

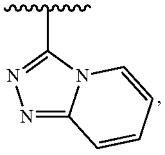, 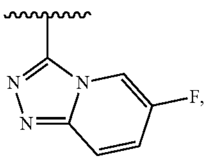 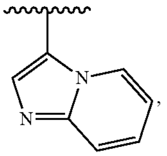, 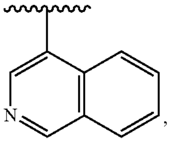, 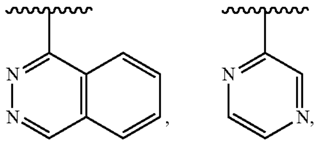

-continued

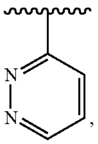, 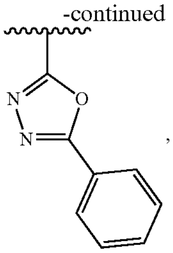, 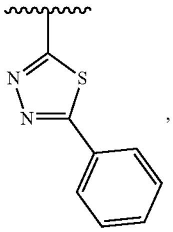,

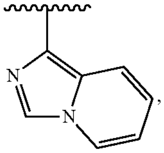, and 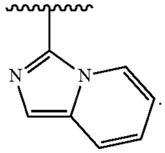.

In some embodiments, $R^2$ is hydrogen.

In some embodiments, $X^1$ is $CR^{3a}$, $X^2$ is $CR^{3b}$, $X^3$ is $CR^{3c}$, and $X^4$ is $CR^{3d}$, and one of $R^{3a}$, $R^{3b}$, $R^{3c}$ and $R^{3d}$ is selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, $—OR^{3e}$, $—COOR^{3f}$, $—CON(R^{3g})(R^{3h})$, and $—(CH_2)_{n3}$-$G^3$, and the remaining three of $R^{3a}$, $R^{3b}$, $R^{3c}$ and $R^{3d}$ are hydrogen. In some embodiments, one or two of $X^1$, $X^2$, $X^3$, and $X^4$ is N.

In some embodiments, $R^4$ is selected from: a 5-membered monocyclic heteroaryl having 1, 2, 3, or 4 nitrogen atoms, which is unsubstituted or substituted with 1 or 2 substituents independently selected from $C_1$-$C_3$ alkyl; and a 5- or 6-membered heterocyclyl having 1, 2, or 3 heteroatoms independently selected from N and O, which is unsubstituted or substituted with 1 or 2 substituents independently selected from oxo and thioxo; cyano; $—CR^{4c}R^{4d}—NR^{4a}R^{4b}$; and $—C(O)NR^{4a}R^{4b}$; wherein $R^{4a}$ and $R^{4b}$ are each independently selected from hydrogen and methyl, and $R^{4c}$ and $R^{4d}$ are each independently selected from hydrogen, methyl, and halomethyl (e.g., difluoromethyl or trifluoromethyl). In some embodiments, $R^4$ is a 5-membered monocyclic heteroaryl selected from pyrazolyl, imidazolyl, triazolyl, and tetrazolyl, each of which is independently unsubstituted or substituted with one substituent selected from $C_1$-$C_3$ alkyl. In some embodiments, $R^4$ is a 5- or 6-membered heterocyclyl selected from pyrrolidinyl, piperidinyl, dihydropyrrolyl, dihydrotriazolyl, dihydrooxadiazolyl, and dihydropyridinyl, each of which is independently unsubstituted or substituted with one substituent selected from oxo and thioxo. In some embodiments, $R^4$ is selected from cyano, $—CH_2NR^{4a}R^{4b}$, and $—C(O)NR^{4a}R^{4b}$ wherein $R^{4a}$ and $R^{4b}$ are each independently selected from hydrogen and methyl. In some embodiments, $R^4$ is selected from:

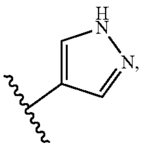 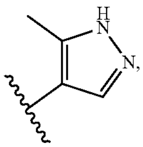 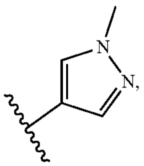

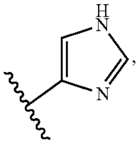 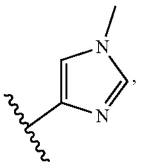 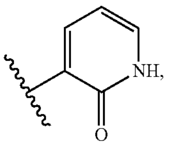

-continued

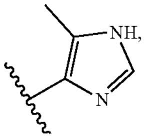 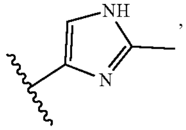, 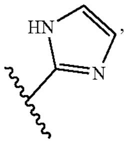

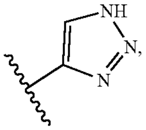 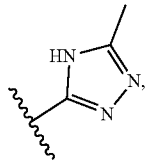 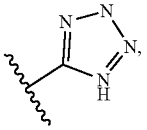

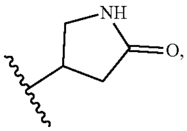 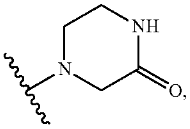 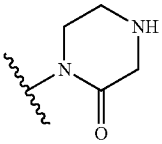,

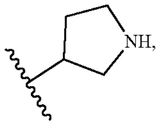 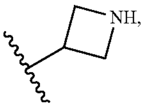 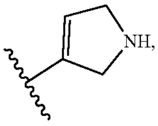

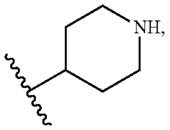 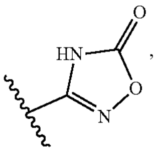, 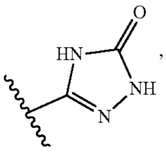,

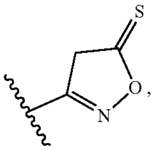 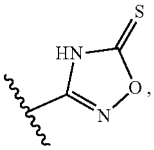 

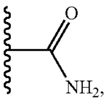 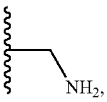 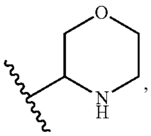,

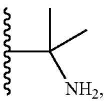 and 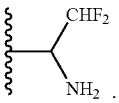.

In some embodiments, $R^4$ is:

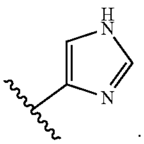 [SMILES: *c1c[nH]cn1].

In some embodiments, the compound is selected from:
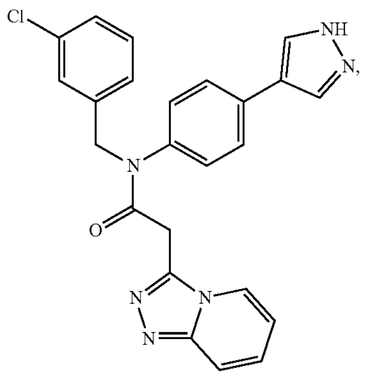
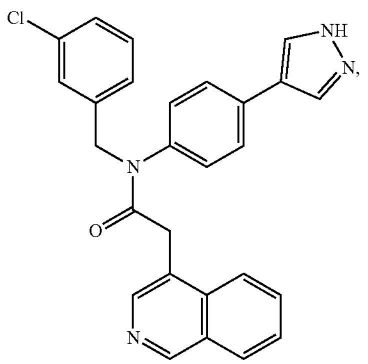
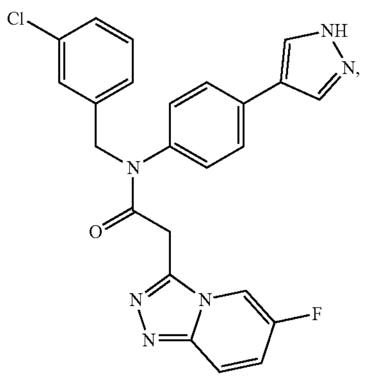
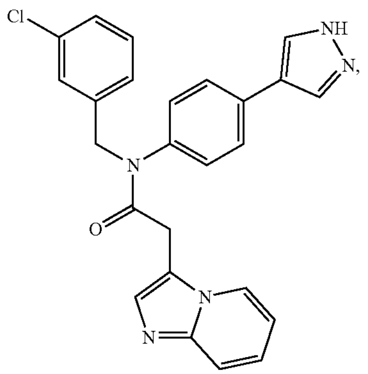
-continued
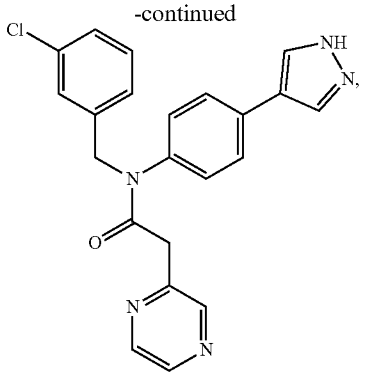
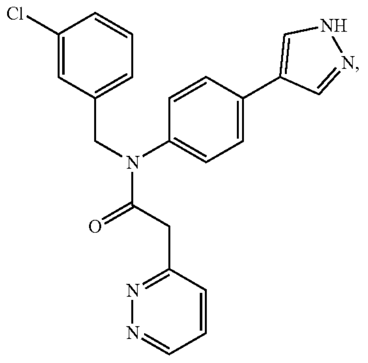
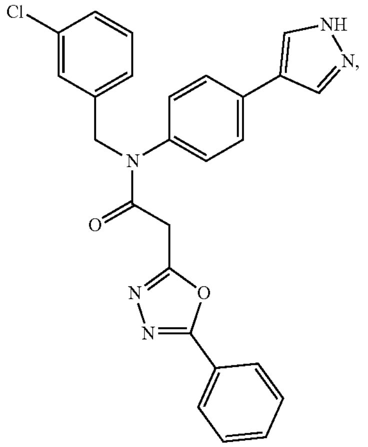
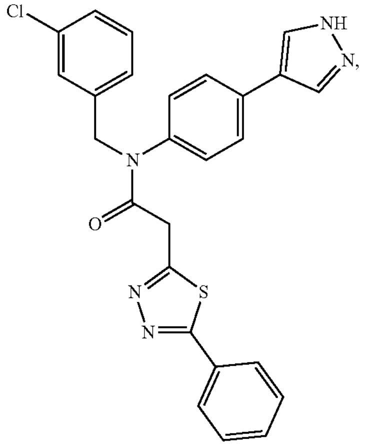

-continued
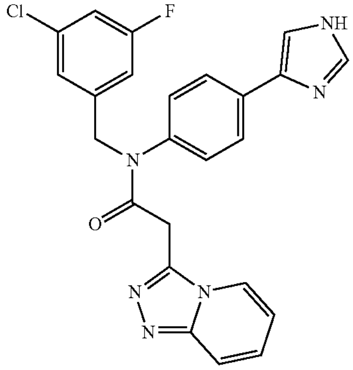
,
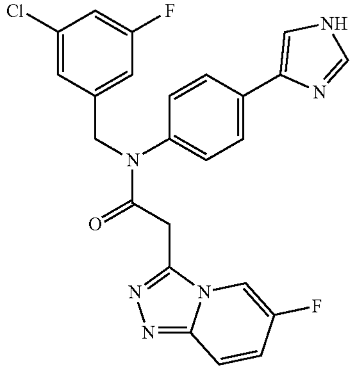
,
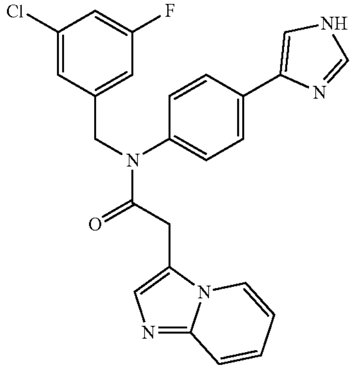
,
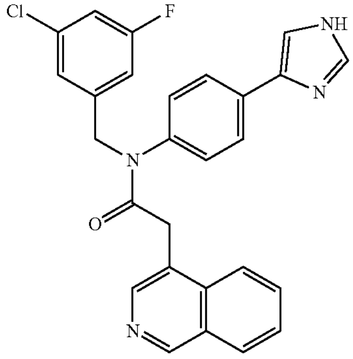
,
-continued
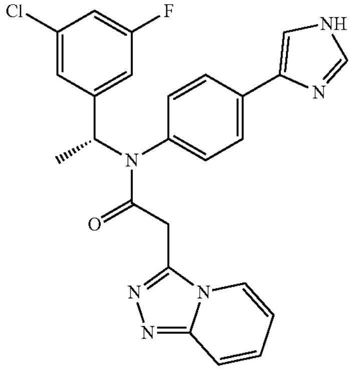
,
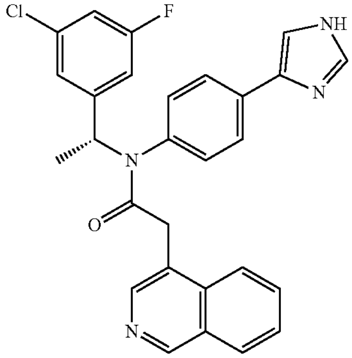
,
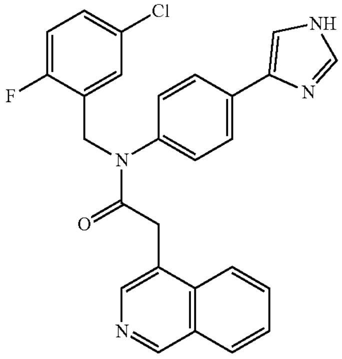
,
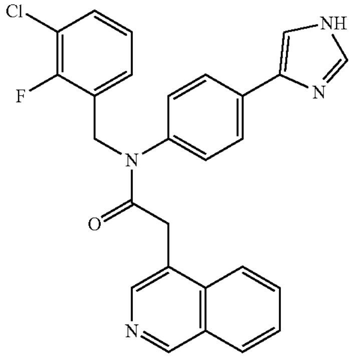
, -continued
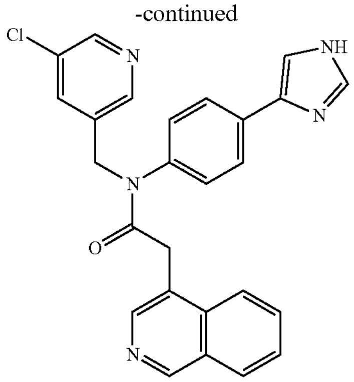
,
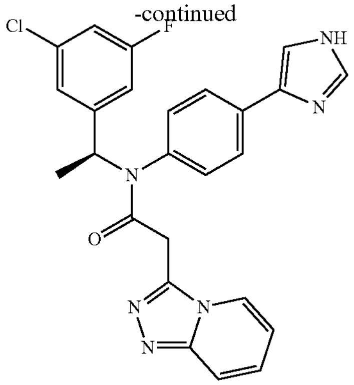
,
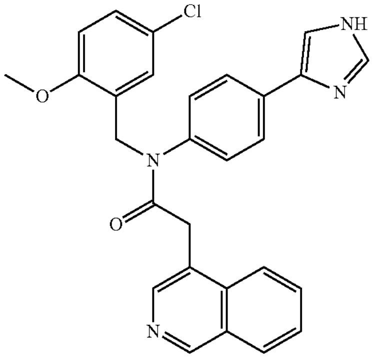
,
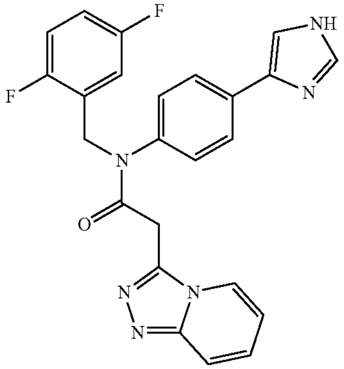
,
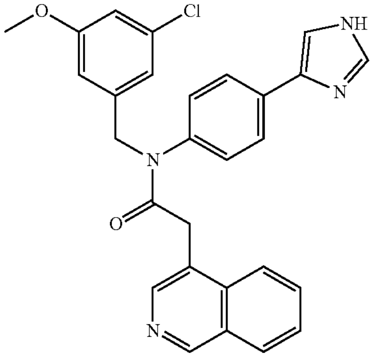
,
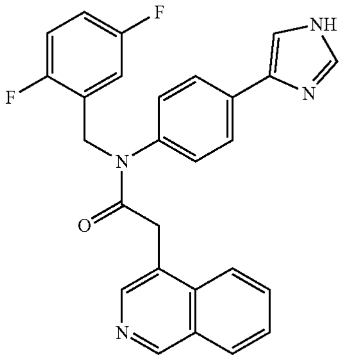
,
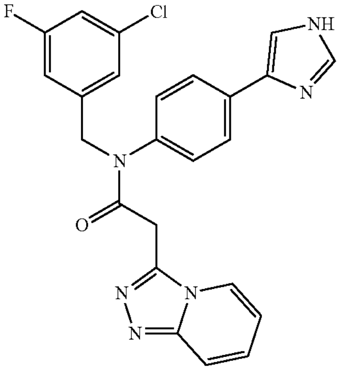
,
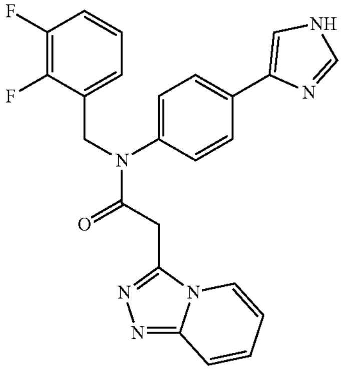
, -continued
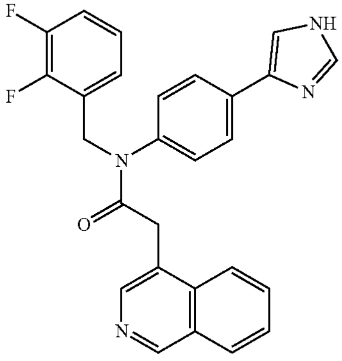
,
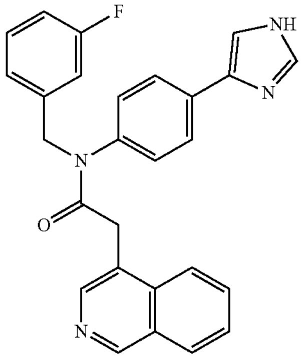
,
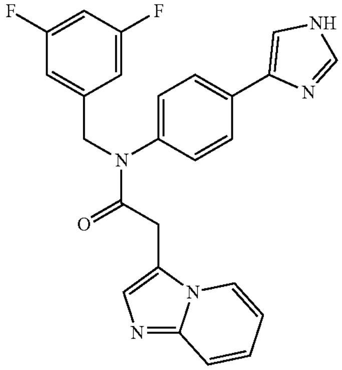
,
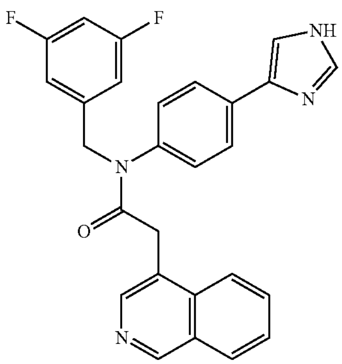
,
-continued
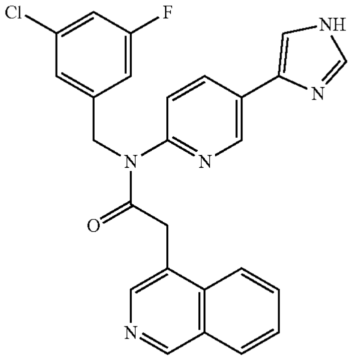
,
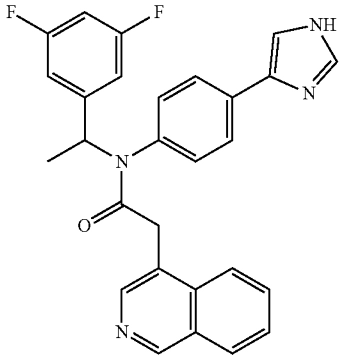
,
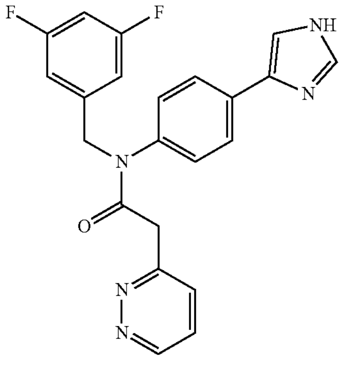
,
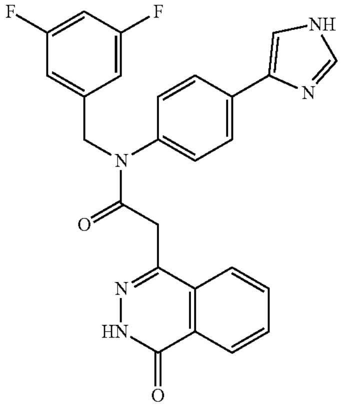
, -continued
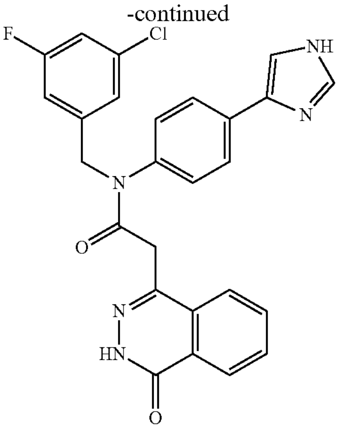
,
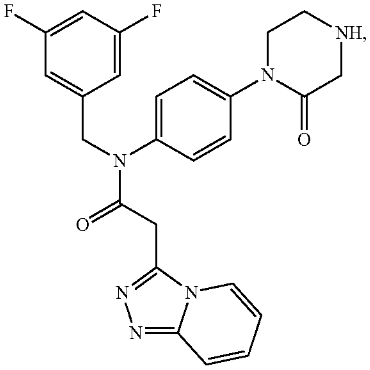
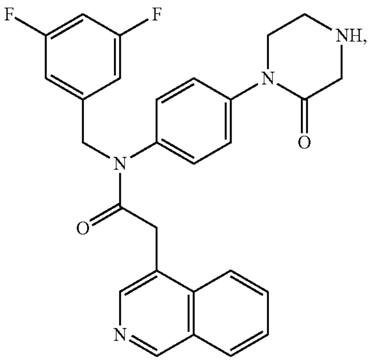
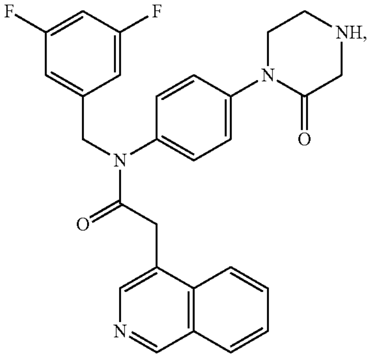
-continued
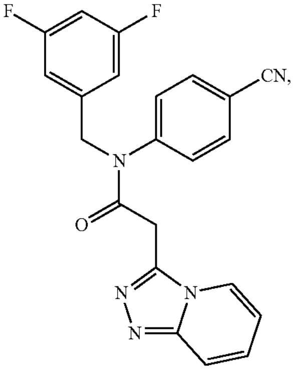
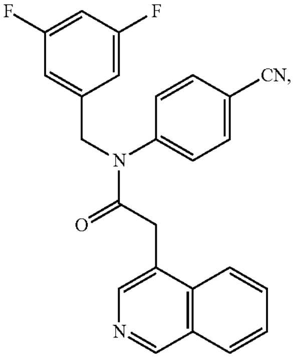
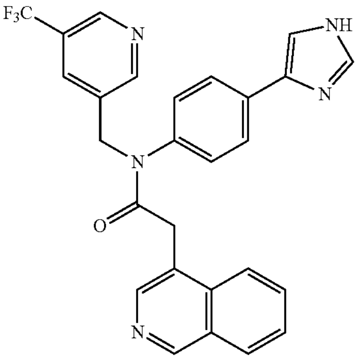
,
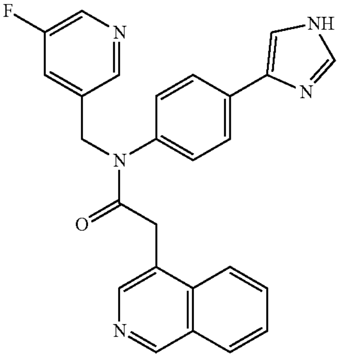
, -continued
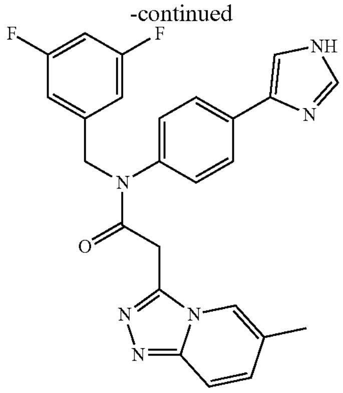
,
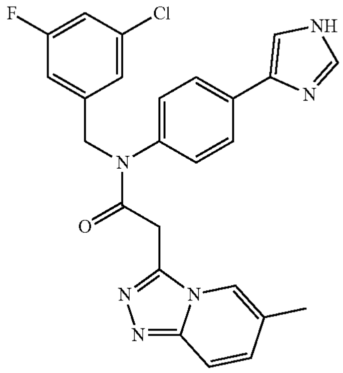
,
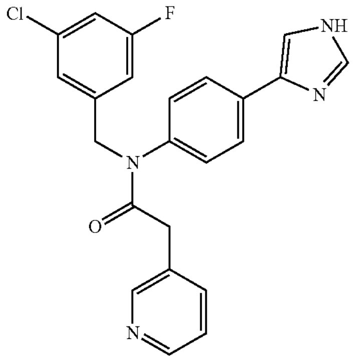
,
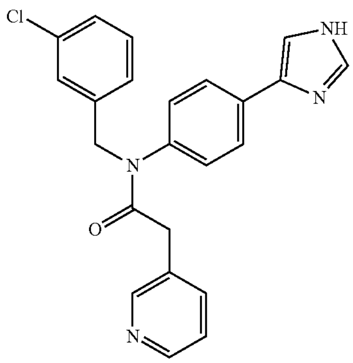
,
-continued
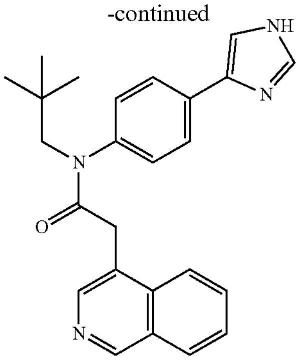
,
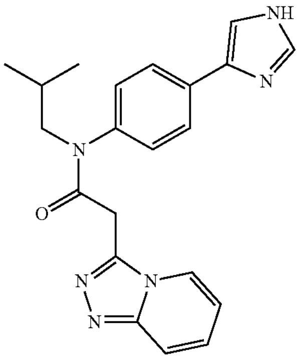
,
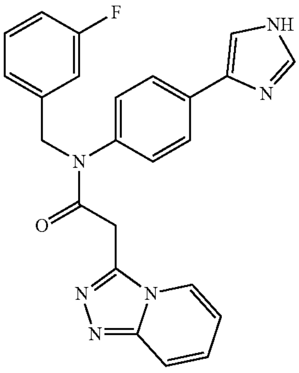
,
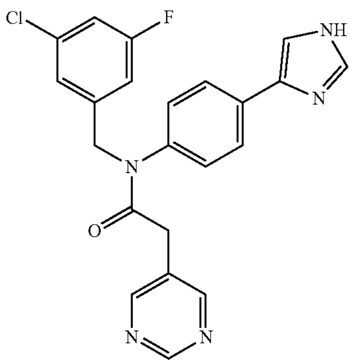
, -continued
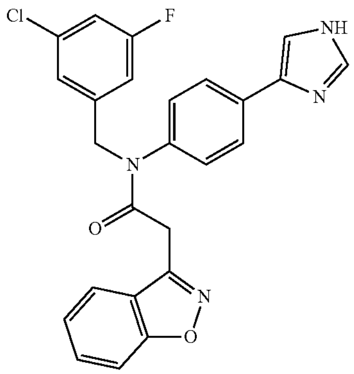
,
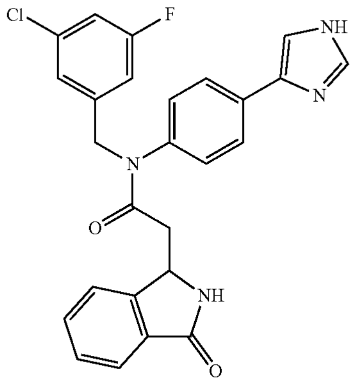
,
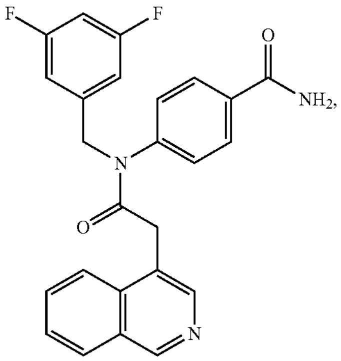
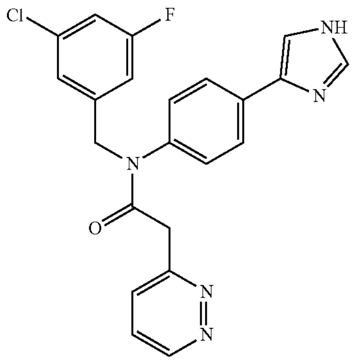
,
-continued
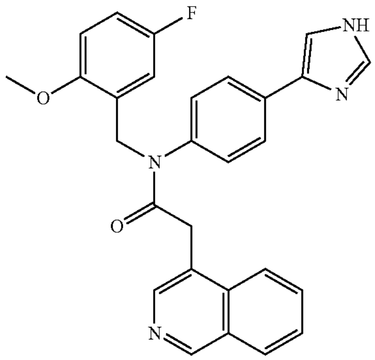
,
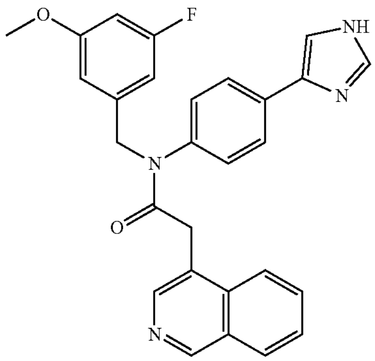
,
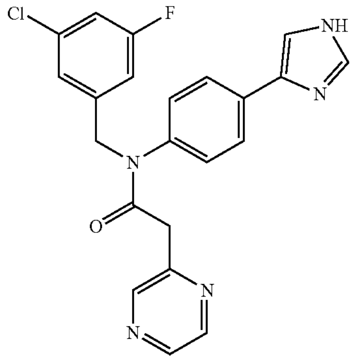
,
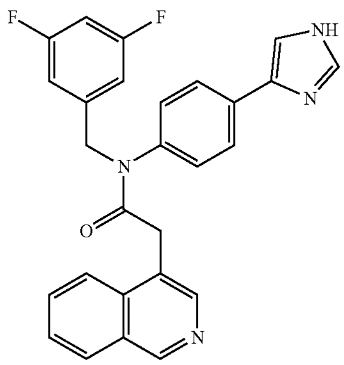
, -continued
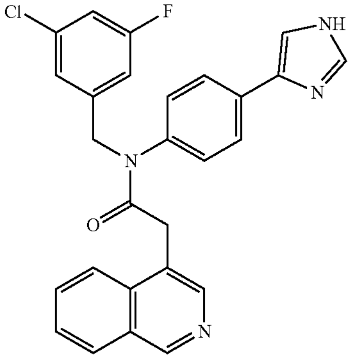
,
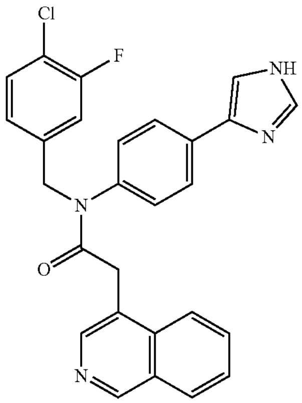
,
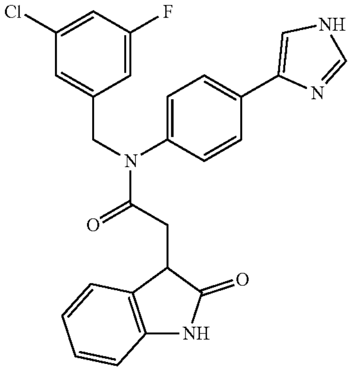
,
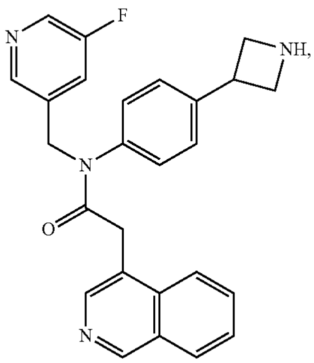
-continued
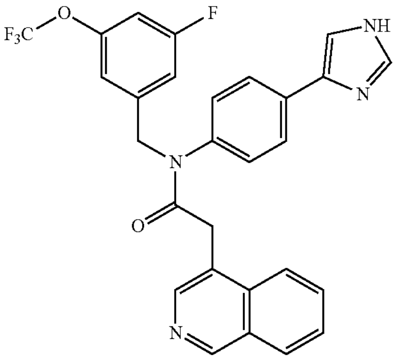
,
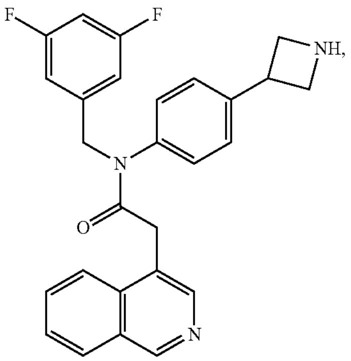
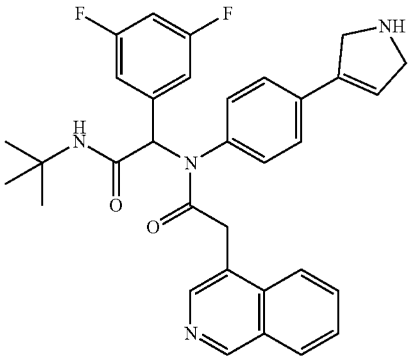
,
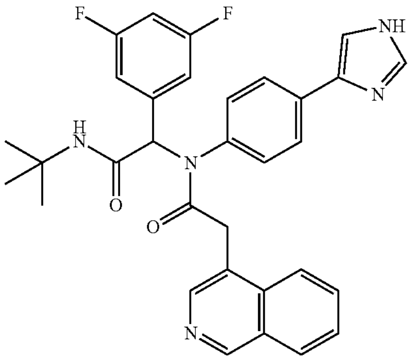
, -continued
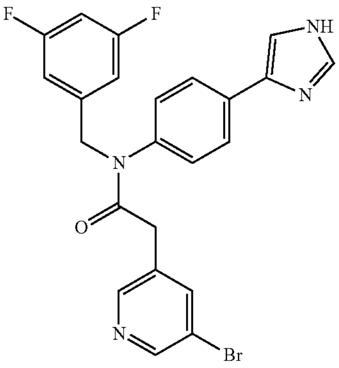
,
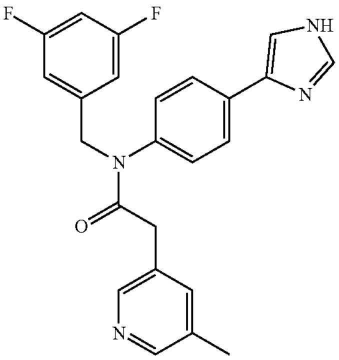
,
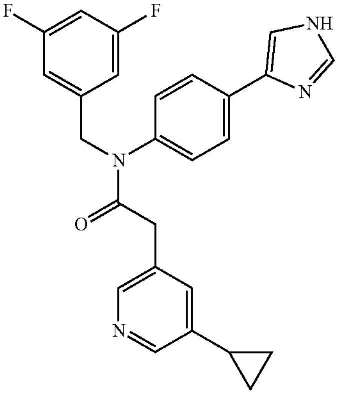
,
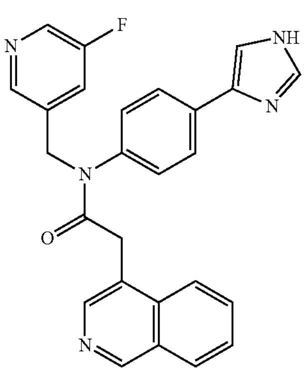
,
-continued
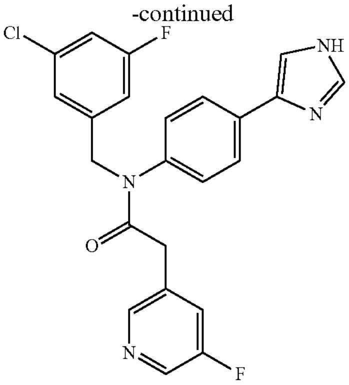
,
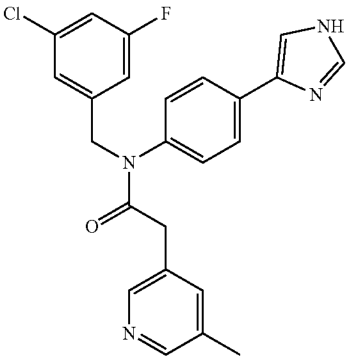
,
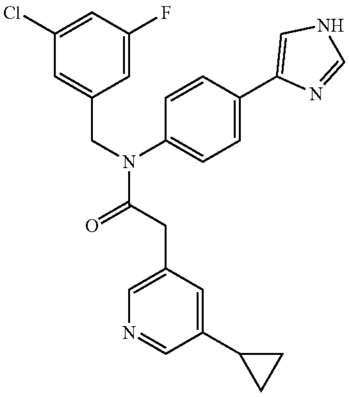
,
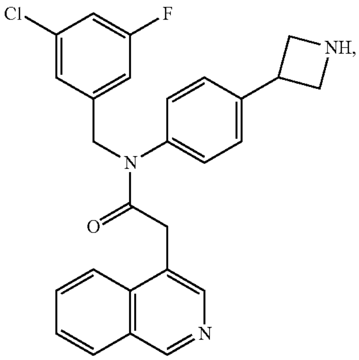
, -continued
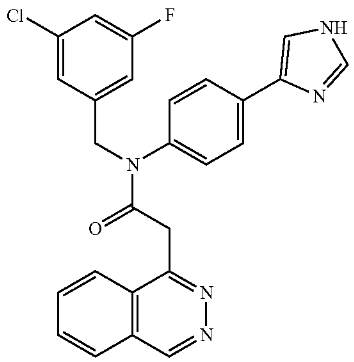
,
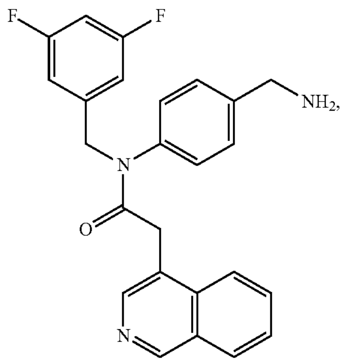
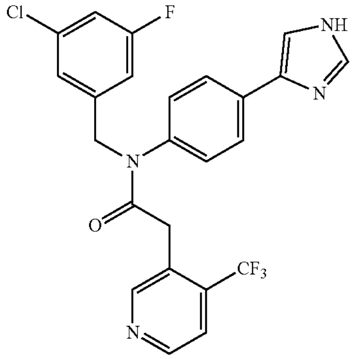
,
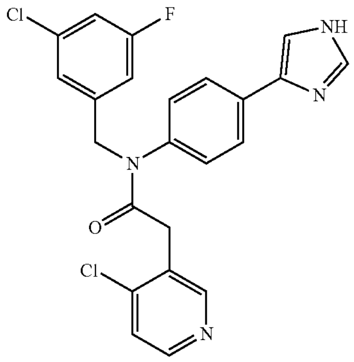
,
-continued
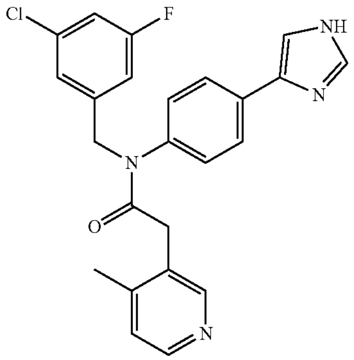
,
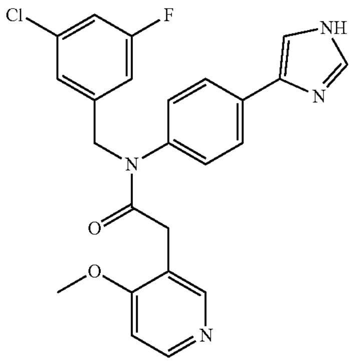
,
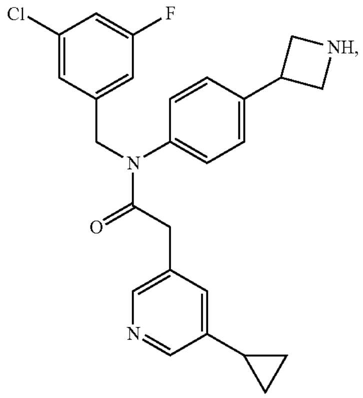
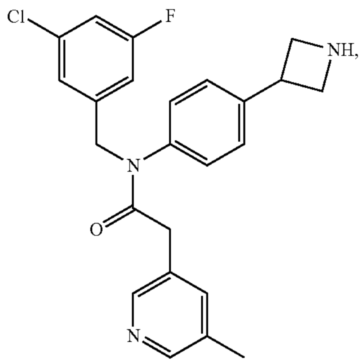

-continued

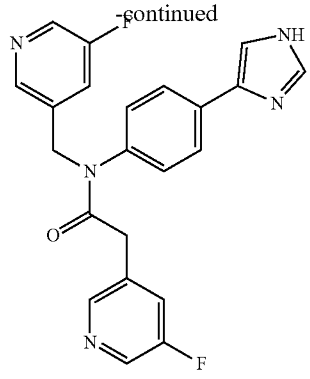

,

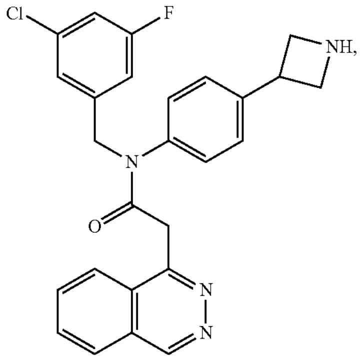

, and

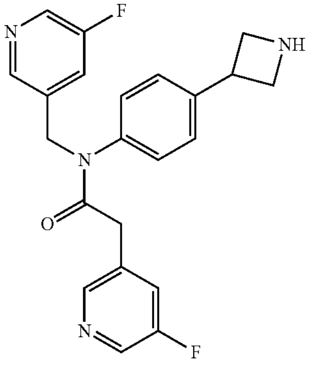

and pharmaceutically acceptable salts thereof.

In another aspect, the disclosure provides a pharmaceutical composition comprising a compound disclosed herein (e.g., a compound of formula (I)), or a pharmaceutically acceptable salt thereof, and a pharmaceutically acceptable carrier.

In another aspect, the disclosure provides a method of treating a viral infection in a subject in need thereof, comprising administering to the subject a therapeutically effective amount of a compound disclosed herein (e.g., a compound of formula (I)), or a pharmaceutically acceptable salt thereof. In some embodiments, the viral infection is a coronavirus infection. In some embodiments, the coronavirus infection is a SARS-CoV-2 infection.

In another aspect, the disclosure provides a method of inhibiting viral replication in a sample, comprising contacting the sample with a compound disclosed herein (e.g., a compound of formula (I)), or a pharmaceutically acceptable salt thereof, in an amount effective to inhibit viral replication. In some embodiments, the sample comprises a coronavirus. In some embodiments, the coronavirus is a SARS-CoV-2 virus In another aspect, the disclosure provides a method inhibiting a 3C-like protease in a sample, comprising contacting the sample with a compound disclosed herein (e.g., a compound of formula (I)), or a pharmaceutically acceptable salt thereof, in an amount effective to inhibit the 3C-like protease. In some embodiments, the 3C-like protease is a SARS-CoV-2 3C-like protease.

DETAILED DESCRIPTION

The disclosure relates to compounds of formula (I), pharmaceutical compositions comprising the compounds, and methods of using the compounds, e.g., in methods of inhibiting viral replication, and in methods of treating a viral infection, such as a coronavirus infection. Compounds of formula (I) are potent inhibitors of coronavirus 3CLpro.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, $3^{rd}$ Edition, John Wiley & Sons, Inc., New York, 2018; and Carruthers, Some Modern Methods of Organic Synthesis, $3^{rd}$ Edition, Cambridge University Press, Cambridge, 1987; the entire contents of each of which are incorporated herein by reference.

As used herein, the term "alkyl" means a straight or branched saturated hydrocarbon chain containing from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), 1 to 4 carbon atoms ($C_1$-$C_4$ alkyl), 6 to 20 carbon atoms ($C_6$-$C_{20}$ alkyl), or 8 to 14 carbon atoms ($C_8$-$C_{14}$ alkyl). Representative examples of alkyl include, but are not limited to, methyl, ethyl, n-propyl, iso propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

As used herein, the term "amino" refers to a group —$NR_2$, wherein each R is independently selected from hydrogen and alkyl (as defined herein). Accordingly, when the term "amino" is used herein, the term encompasses an —$NH_2$ group, an alkylamino group (e.g., —$NHCH_3$), and a dialkylamino group (—$N(CH_3)_2$).

As used herein, the term "aminoalkyl" refers to an alkyl group, as defined herein, appended to the parent molecular moiety through an —NH— group. Representative examples of aminoalkyl include methylamino (—$NH(CH_3)$) and ethylamino (i.e. —$NH(CH_2CH_3)$).

As used herein, the term "aryl" refers to an aromatic carbocyclic ring system having a single ring (monocyclic) or multiple rings (bicyclic or tricyclic) including fused ring systems, and zero heteroatoms. As used herein, aryl contains 6-20 carbon atoms ($C_6$-$C_{20}$ aryl), 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl). Representative examples of aryl groups include, but are not limited to, phenyl, naphthyl, anthracenyl, and phenanthrenyl.

As used herein, the term "arylalkyl" refers to an aryl group, as defined herein, appended to the parent molecular moiety through an alkyl group, as defined herein. Representative examples of arylalkyl include, but are not limited to, phenylmethyl (i.e., benzyl) and phenylethyl.

As used herein, the term "cyano" means a —CN group.

As used herein, the term "cycloalkyl" refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "halogen" or "halo" means F, Cl, Br, or I.

As used herein, the term "haloalkyl" means an alkyl group, as defined herein, in which at least one hydrogen atom (e.g., one, two, three, four, five, six, seven or eight hydrogen atoms) is replaced by a halogen. Representative examples of haloalkyl include, but are not limited to, fluoromethyl, difluoromethyl, trifluoromethyl, 2,2,2-trifluoroethyl, and 3,3,3-trifluoropropyl.

As used herein, the term "haloalkoxy" means a haloalkyl group, as defined herein, is appended to the parent molecular moiety through an oxygen atom. Representative examples of haloalkoxy include, but are not limited to, difluoromethoxy, trifluoromethoxy, and 2,2,2-trifluoroethoxy.

As used herein, the term "heteroaryl" refers to an aromatic group having a single ring (monocyclic) or multiple rings (bicyclic or tricyclic) having one or more ring heteroatoms independently selected from O, N, and S. The aromatic monocyclic rings are five- or six-membered rings containing at least one heteroatom independently selected from O, N, and S (e.g. 1, 2, 3, or 4 heteroatoms independently selected from O, N, and S). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, and a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, benzoisoxazolyl, benzoisothiazolyl, chromenyl, imidazopyridinyl, imidazothiazolyl, indazolyl, indolyl, isobenzofuranyl, isoindolyl, isoquinolinyl, naphthyridinyl, phthalazinyl, purinyl, pyridoimidazolyl, quinazolinyl, quinolinyl, quinoxalinyl, thiazolopyridinyl, thiazolopyrimidinyl, thienopyrrolyl, thienothienyl, and triazolopyridinyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

As used herein, the term "heterocycle" or "heterocyclic" refers to a saturated or partially unsaturated non-aromatic cyclic group having one or more ring heteroatoms independently selected from O, N, and S. The heterocycle can be monocyclic heterocycle, a bicyclic heterocycle, or a tricyclic heterocycle. The monocyclic heterocycle is a three-, four-, five-, six-, seven-, or eight-membered ring containing at least one heteroatom independently selected from O, N, and S. The three- or four-membered ring contains zero or one double bond, and one heteroatom selected from O, N, and S. The five-membered ring contains zero or one double bond and one, two or three heteroatoms selected from O, N, and S. The six-membered ring contains zero, one, or two double bonds and one, two, or three heteroatoms selected from O, N, and S. The seven- and eight-membered rings contains zero, one, two, or three double bonds and one, two, or three heteroatoms selected from O, N, and S. The heteroatom in the ring can be oxidized (e.g., if the ring heteroatom is S, it can be oxidized to SO or $SO_2$). Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.$1^{3,7}$]decane), and oxa-adamantane (2-oxatricyclo[3.3.1.$1^{3,7}$]decane). The monocyclic, bicyclic, and tricyclic heterocycles are connected to the parent molecular moiety through any carbon atom or any nitrogen atom contained within the rings.

As used herein, the term "hydroxy" means an —OH group.

As used herein, the term "hydroxyalkyl" means an alkyl group, as defined herein, in which at least one hydrogen atom is replaced by a hydroxy group. Representative examples of haloalkyl include, but are not limited to, hydroxymethyl, 1-hydroxyethyl, and 2-hydroxyethyl.

As used herein, the term "substituent" refers to a group substituted on an atom of the indicated group. When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroalkyl, heteroaryl, heterocyclyl, hydroxy, hydrazino, imino, oxo, nitro, phosphate, phosphonate, sulfonic acid, thiol, thione, or combinations thereof.

As used herein, in chemical structures the indication:

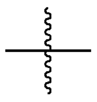

represents a point of attachment of one moiety to another moiety (e.g., a substituent group to the core compound).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., $—CH_2O—$ optionally also recites $—OCH_2—$, and —OC(O)NH— also optionally recites —NHC(O)O—.

The terms "administer," "administering," "administered," or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Effective amount," as used herein, refers to a dosage of a compound or a composition effective for eliciting a desired effect. This term as used herein may also refer to an amount effective at bringing about a desired in vivo effect in a subject, such as a human.

As used herein, the term "subject" is intended to include human and non-human animals. Exemplary human subjects include a human patient having a disorder, e.g., a viral infection. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Compounds

The present disclosure provides a compound of formula (I):

(I)

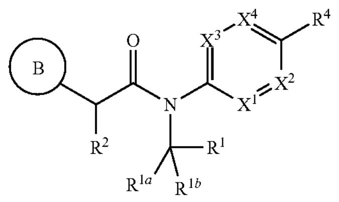

or a pharmaceutically acceptable salt thereof, wherein:

$R^1$ is selected from: aryl; a monocyclic heteroaryl having 1, 2, or 3 heteroatoms independently selected from N, O, and S; $C_3$-$C_6$ cycloalkyl; a monocyclic heterocyclyl having 1, 2, or 3 heteroatoms independently selected from N, O, and S; $C_3$-$C_6$ alkyl; and $C_1$-$C_6$ haloalkyl;

$R^{1a}$ and $R^{1b}$ are each independently selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, $C_1$-$C_3$ aminoalkyl, $—CON(R^{1c})(R^{1d})$, and $—(CH_2)_{n1}$-$G^1$, wherein n1 is 0, 1, or 2, and wherein $G^1$ is selected from $C_3$-$C_6$ cycloalkyl, a 4- to 6-membered monocyclic heterocycle, and a 5- or 6-membered monocyclic heteroaryl; or wherein $R^{1a}$ and $R^{1b}$ are taken together with the carbon atom to which they are attached to form a $C_3$-$C_6$ cycloalkyl;

$R^{1c}$ and $R^{1d}$ are each independently selected from hydrogen, $C_1$-$C_4$ alkyl, $C_1$-$C_4$ haloalkyl, and $C_3$-$C_6$ cycloalkyl;

B is a monocyclic heteroaryl, a bicyclic heteroaryl, or a bicyclic heterocyclyl, wherein B is linked to the remainder of the molecule via a carbon atom;

$R^2$ is hydrogen or $C_1$-$C_3$ alkyl;

$X^1$ is $CR^{3a}$ or N, $X^2$ is $CR^{3b}$ or N, $X^3$ is $CR^{3c}$ or N, and $X^4$ is $CR^{3d}$ or N;

$R^{3a}$, $R^{3b}$, $R^{3c}$ and $R^{3d}$ are each independently selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, wherein $R^{3e}$, $R^{3f}$, $R^{3g}$, and $R^{3h}$ are each independently selected from hydrogen and $C_1$-$C_3$ alkyl, wherein n3 is 0, 1, or 2, and wherein $G^3$ is selected from $C_3$-$C_6$ cycloalkyl and a 4- to 6-membered monocyclic heterocycle;

$R^4$ is selected from: a 5-membered monocyclic heteroaryl having 1, 2, 3, or 4 heteroatoms independently selected from N, O, and S; a 5- or 6-membered heterocyclyl having 1, 2, or 3 heteroatoms independently selected from N, O, and S; cyano; —$CR^{4c}R^{4d}$—$NR^{4a}R^{4b}$, and —$C(O)NR_{4a}R^{4b}$;

$R^{4a}$ and $R^{4b}$ are each independently selected from hydrogen and $C_1$-$C_3$ alkyl; and $R^{4c}$ and $R^{4d}$ are each independently selected from hydrogen, $C_1$-$C_3$ alkyl, $C_1$-$C_3$ haloalkyl, and $C_3$-$C_6$ cycloalkyl, or $R^{4c}$ and $R^{4d}$, together with the carbon atom to which they are attached, are taken together to form a 3- to 6-membered ring;

wherein each alkyl, heteroaryl, aryl, cycloalkyl, and heterocyclyl is independently unsubstituted or substituted with 1, 2, or 3 substituents independently selected from $C_1$-$C_3$ alkyl, $C_1$-$C_3$ alkoxy, $C_1$-$C_3$ hydroxyalkyl, halo, $C_1$-$C_3$ haloalkyl, $C_1$-$C_3$ haloalkoxy, $C_3$-$C_6$ cycloalkyl, aryl, arylalkyl, amino, hydroxy, cyano, oxo, and thioxo.

The present disclosure also provides a compound of formula (Ia):

(Ia)

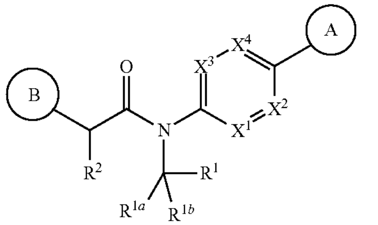

or a pharmaceutically acceptable salt thereof, wherein:

A is selected from: a 5-membered monocyclic heteroaryl having 1, 2, 3, or 4 heteroatoms independently selected from N, O, and S; and a 4-, 5-, or 6-membered heterocyclyl having 1, 2, or 3 heteroatoms independently selected from N, O, and S;

$R^1$ is selected from: aryl; a monocyclic heteroaryl having 1, 2, or 3 heteroatoms independently selected from N, O, and S; $C_3$-$C_6$ cycloalkyl; a monocyclic heterocyclyl having 1, 2, or 3 heteroatoms independently selected from N, O, and S; $C_3$-$C_6$ alkyl; and $C_1$-$C_6$ haloalkyl;

$R^{1a}$ and $R^{1b}$ are each independently selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, $C_1$-$C_3$ aminoalkyl, —$CON(R^{1c})(R^{1d})$, and —$(CH_2)_{n1}$-$G^1$, wherein n1 is 0, 1, or 2, and wherein $G^1$ is selected from $C_3$-$C_6$ cycloalkyl, a 4- to 6-membered monocyclic heterocycle, and a 5- or 6-membered monocyclic heteroaryl; or wherein $R^{1a}$ and $R^{1b}$ are taken together with the carbon atom to which they are attached to form a $C_3$-$C_6$ cycloalkyl;

$R^{1c}$ and $R^{1d}$ are each independently selected from hydrogen, $C_1$-$C_4$ alkyl, $C_1$-$C_4$ haloalkyl, and $C_3$-$C_6$ cycloalkyl;

B is a monocyclic or bicyclic heteroaryl linked to the remainder of the molecule via a carbon atom;

$R^2$ is hydrogen or $C_1$-$C_3$ alkyl;

$X^1$ is $CR^{3a}$ or N, $X^2$ is $CR^{3b}$ or N, $X^3$ is $CR^{3c}$ or N, and $X^4$ is $CR^{3d}$ or N; and $R^{3a}$, $R^{3b}$, $R^{3c}$ and $R^{3d}$ are each independently selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, wherein $R^{3e}$, $R^{3f}$, $R^{3g}$, and $R^{3h}$ are each independently selected from hydrogen and $C_1$-$C_3$ alkyl, wherein n3 is 0, 1, or 2, and wherein $G^3$ is selected from $C_3$-$C_6$ cycloalkyl and a 4- to 6-membered monocyclic heterocycle;

wherein each alkyl, heteroaryl, aryl, cycloalkyl, and heterocyclyl is independently unsubstituted or substituted with 1, 2, or 3 substituents independently selected from $C_1$-$C_3$ alkyl, $C_1$-$C_3$ alkoxy, $C_1$-$C_3$ hydroxyalkyl, halo, $C_1$-$C_3$ haloalkyl, $C_1$-$C_3$ haloalkoxy, $C_3$-$C_6$ cycloalkyl, aryl, arylalkyl, amino, hydroxy, cyano, oxo, and thioxo.

In some embodiments, $R^1$ is selected from: aryl; a monocyclic heteroaryl having 1 or 2 heteroatoms independently selected from N, O, and S; $C_3$-$C_5$ cycloalkyl; a monocyclic 4- or 5-membered heterocyclyl having 1 heteroatom selected from N, O, and S; $C_3$-$C_5$ alkyl; and $C_1$-$C_2$ haloalkyl. In some embodiments, $R^1$ is selected from phenyl, pyridyl, thiophenyl, thiazolyl, cyclopropyl, cyclobutyl, cyclopentyl, oxetanyl, tetrahydrofuranyl, isobutyl, tert-butyl, and trifluoromethyl. In some embodiments, $R^1$ is selected from aryl and a monocyclic 6-membered heteroaryl having 1 or 2 nitrogen atoms, each of which is independently unsubstituted or substituted with 1 or 2 substituents independently selected from halo, $C_1$-$C_3$ alkyl, $C_1$-$C_3$ alkoxy, $C_1$-$C_3$ hydroxyalkyl, $C_1$-$C_3$ haloalkyl, $C_1$-$C_3$ haloalkoxy, and cyano. In some embodiments, $R^1$ is phenyl or pyridyl, each of which is independently unsubstituted or substituted with 1 or 2 substituents independently selected from fluoro, chloro, methyl, methoxy, trifluoromethyl, trifluoromethoxy, hydroxymethyl, and cyano. In some embodiments, $R^1$ is phenyl or pyridyl, each of which is independently unsubstituted or substituted with 1 or 2 substituents independently selected from halo, $C_1$-$C_3$ alkyl, $C_1$-$C_3$ haloalkyl, $C_1$-$C_3$ haloalkoxy, and $C_1$-$C_3$ alkoxy. In some embodiments, $R^1$ is phenyl or pyridyl, each of which is independently unsubstituted or substituted with 1 or 2 substituents independently selected from fluoro and chloro. In some embodiments, $R^1$ is phenyl substituted with 1 or 2 substituents independently selected from fluoro and chloro.

In some embodiments, $R^1$ is selected from:

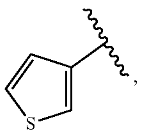, 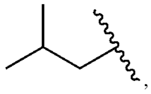, 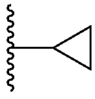,

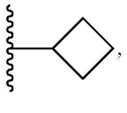, 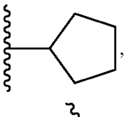, 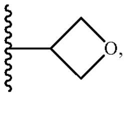,

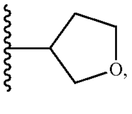, 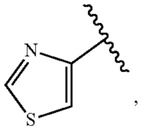, 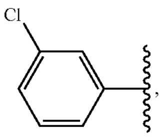,

-continued
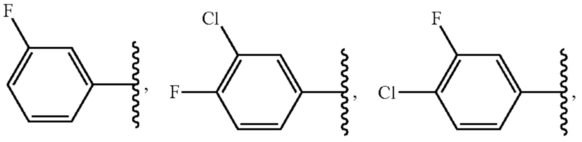
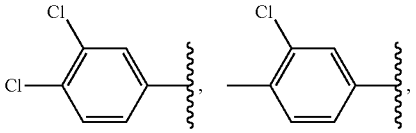
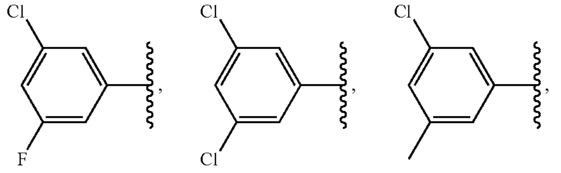
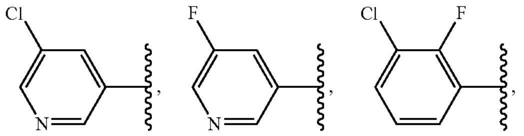
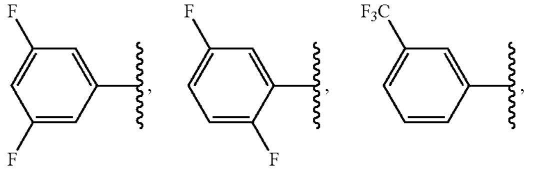
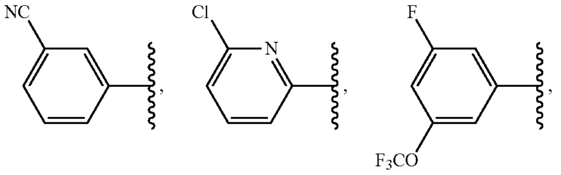
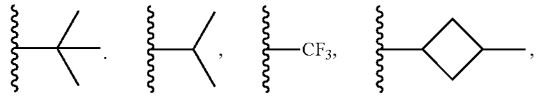
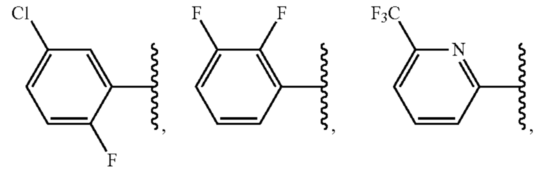
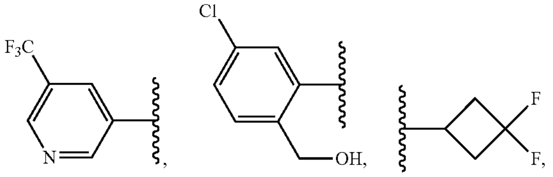
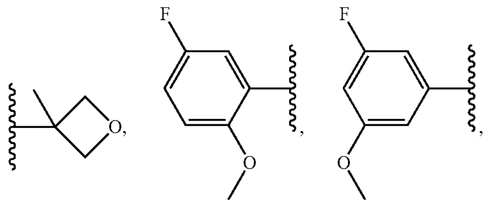
-continued
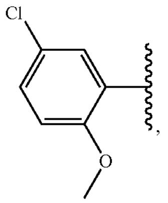
and
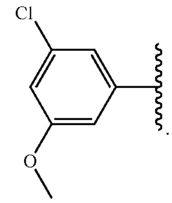
In some embodiments, $R^1$ is selected from:
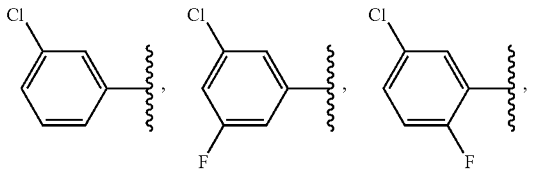
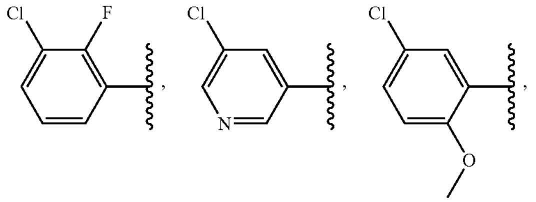
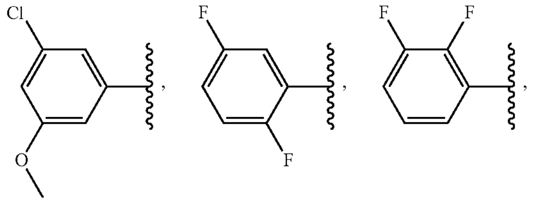
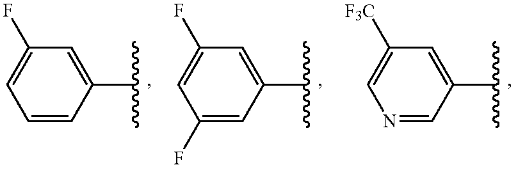
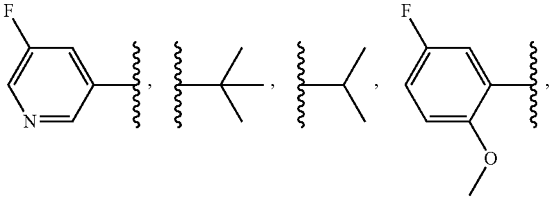
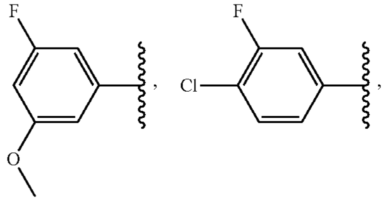
and
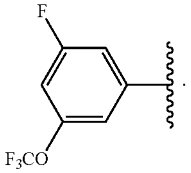

In some embodiments, $R^1$ is selected from:

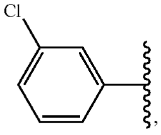, 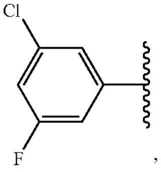, and 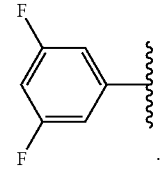.

In some embodiments, $R^1$ is selected from:

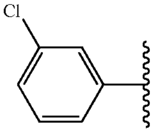 and 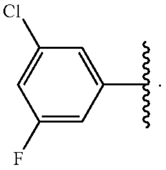.

In some embodiments, $R^{1a}$ is hydrogen and $R^{1b}$ is selected from hydrogen, $C_1$-$C_3$ alkyl, $C_1$-$C_3$ haloalkyl, $C_1$-$C_3$ hydroxyalkyl, $C_1$-$C_3$ aminoalkyl, —CON($R^{1c}$)($R^{1d}$), and —$(CH_2)_{n1}$-$G^1$. In some embodiments, $R^{1a}$ is hydrogen and $R^{1b}$ is selected from hydrogen, methyl, hydroxymethyl, —$CONH_2$, —$CONH(C(CH_3)_3$, —$CH_2N(CH_3)_2$, —CH(OH)$CF_3$, and —$(CH_2)_{n1}$-$G^1$, n1 is 0 or 1, and $G^1$ is selected from pyrazolyl, morpholino, and N-methylpiperazinyl. In some embodiments, $R^{1a}$ is hydrogen and $R^{1b}$ is hydrogen or methyl. In some embodiments, $R^{1a}$ is hydrogen and $R^{1b}$ is hydrogen. In some embodiments, $R^{1a}$ and $R^{1b}$ are taken together with the carbon atom to which they are attached to form a $C_3$-$C_6$ cycloalkyl (e.g., cyclopropyl).

In some embodiments, $R^2$ is hydrogen. In some embodiments, $R^2$ is $C_1$-$C_3$ alkyl (e.g., methyl).

In some embodiments, B is selected from: a five-membered heteroaryl having 1, 2, 3, or 4 heteroatoms independently selected from N, O, and S; a six-membered heteroaryl having 1, 2, 3, or 4 nitrogen atoms; an 8-10 membered bicyclic heteroaryl having 1, 2, 3, or 4 heteroatoms independently selected from N, O, and S; and an 8-10 membered bicyclic heterocyclyl having 1, 2, 3, or 4 heteroatoms independently selected from N, O, and S; wherein B is linked to the remainder of the molecule via a carbon atom (i.e., a carbon atom of B is linked to the group —$CHR^2$— in formula (I)). In some embodiments, B is selected from: a five-membered heteroaryl having 1, 2, 3, or 4 heteroatoms independently selected from N, O, and S; a six-membered heteroaryl having 1, 2, 3, or 4 nitrogen atoms; and an 8-10 membered bicyclic heteroaryl having 1, 2, 3, or 4 heteroatoms independently selected from N, O, and S; wherein B is linked to the remainder of the molecule via a carbon atom (i.e., a carbon atom of B is linked to the group —$CHR^2$— in formula (I)). In some embodiments, B is selected from: a five-membered heteroaryl having 1, 2, 3, or 4 heteroatoms independently selected from N, O, and S; a six-membered heteroaryl having 1, 2, 3, or 4 nitrogen atoms; and an 8-10 membered bicyclic heteroaryl having 1, 2, 3, or 4 nitrogen atoms; wherein B is linked to the remainder of the molecule via a carbon atom (i.e., a carbon atom of B is linked to the group —$CHR^2$— in formula (I)).

In some embodiments, B is selected from: pyridyl, pyridazinyl, pyrimidinyl, pyrazinyl, pyrrolyl, pyrazolyl, imidazolyl, triazolyl (e.g., 1,2,3-triazolyl or 1,2,4-triazolyl), tetrazolyl, oxazolyl, thiazolyl, oxadiazolyl, and thiadiazolyl, quinolinyl, isoquinolinyl (e.g., isoquinolin-4-yl), phthalazinyl (e.g., phthalazin-1-yl), imidazopyridinyl (e.g., imidazo[1,2-a]pyridinyl or imidazo[1,5-a]pyridinyl, e.g., imidazo[1,2-a]pyridin-3-yl, imidazo[1,5-a]pyridin-1-yl, imidazo[1,5-a]pyridin-3-yl), benzoisoxazolyl (e.g., benzo[d]isoxazol-3-yl), benzoisothiazolyl (e.g., benzo[d]isothiazol-3-yl), triazolopyridinyl (e.g., [1,2,4]triazolo[4,3-a]pyridinyl, e.g., [1,2,4]triazolo[4,3-a]pyridin-3-yl), and isoindolinyl (e.g., isoindolin-1-yl or isoindolin-3-yl). In some embodiments, B is an 8-10 membered bicyclic heteroaryl having 1, 2, 3, or 4 nitrogen atoms (e.g., quinolinyl, isoquinolinyl, phthalizinyl, imidazopyridinyl, or triazolopyridinyl). In some embodiments, B is unsubstituted or substituted with 1, 2, or 3 substituents independently selected from 1, 2, or 3 substituents independently selected from $C_1$-$C_3$ alkyl, $C_1$-$C_3$ alkoxy, halo, $C_1$-$C_3$ haloalkyl, $C_3$-$C_5$ cycloalkyl, aryl, and oxo. In some embodiments, B is substituted with 1 or 2 substituents independently selected from methyl, fluoro, chloro, and phenyl. In some embodiments, B is substituted with 1 or 2 substituents independently selected from methyl, fluoro, chloro, bromo, trifluoromethyl, methoxy, cyclopropyl, oxo, and phenyl.

In some embodiments, B is selected from:

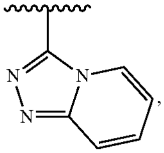, 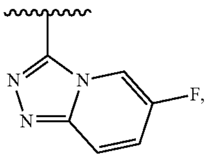, 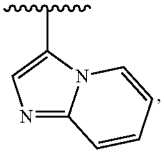,

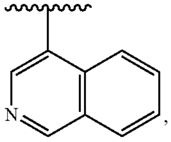, 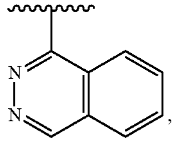, 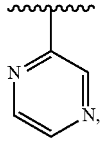

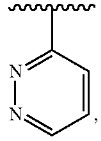, 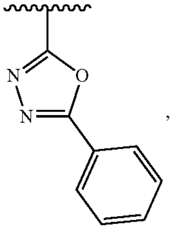, 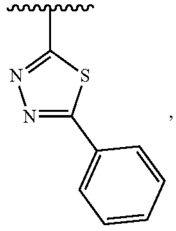,

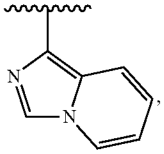, 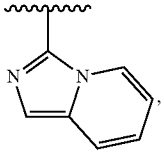, 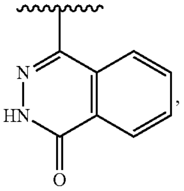,

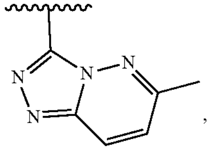, 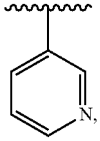 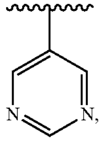

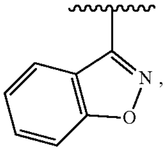, 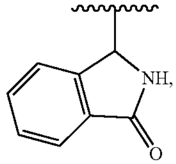 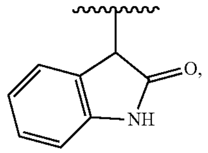

-continued

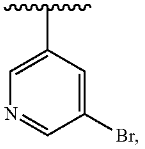 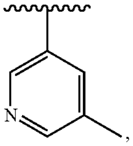 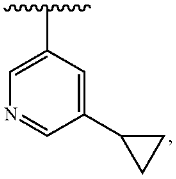

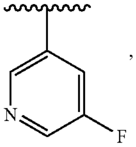, 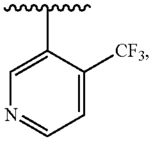 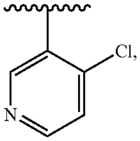

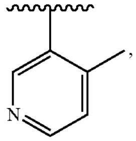 and 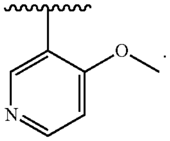

In some embodiments, B is selected from:

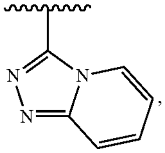 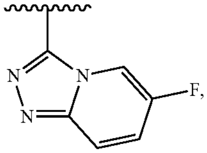 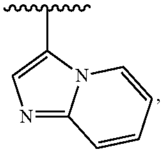

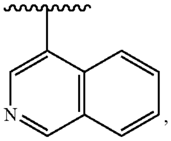 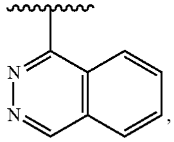 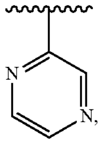

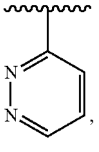 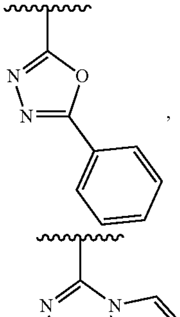, 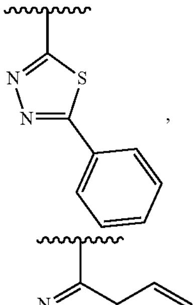,

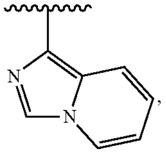 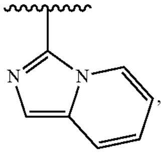 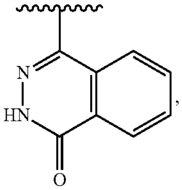

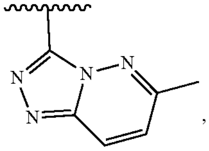, 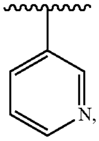 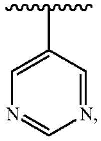

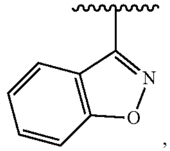, 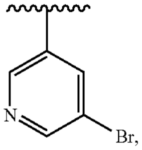 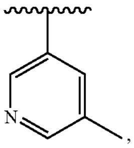

-continued

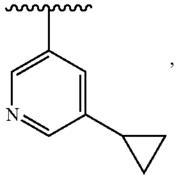, 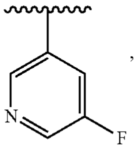, 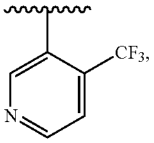

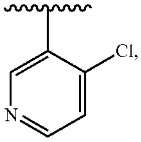 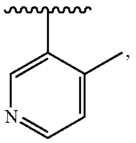 and 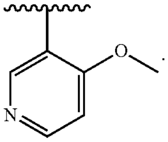

In some embodiments, B is selected from:

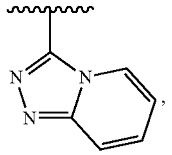

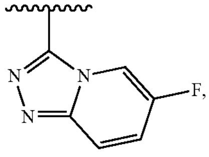

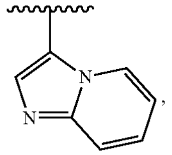

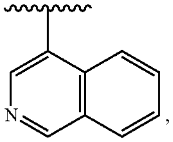

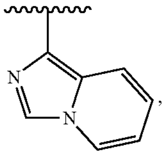 and

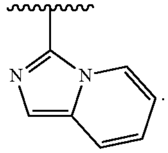

In some embodiments, no more than two of $X^1$, $X^2$, $X^3$ and $X^4$ is N. In some embodiments, one or two of $X^1$, $X^2$, $X^3$, and $X^4$ is N.

In some embodiments, $X^1$ is N, $X^2$ is $CR^{3b}$, $X^3$ is $CR^{3c}$, and $X^4$ is $CR^{3d}$, one of $R^{3b}$, $R^{3c}$, and $R^{3d}$ is selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, and the remaining two of $R^{3b}$, $R^{3c}$ and $R^{3d}$ are hydrogen. In some embodiments, $X^1$ is N, $X^2$ is $CR^{3b}$ $X^3$ is $CR^{3c}$, and $X^4$ is $CR^{3d}$, and $R^{3b}$, $R^{3c}$ and $R^{3d}$ are hydrogen.

In some embodiments, $X^1$ is $CR^{3a}$, $X^2$ is N, $X^3$ is $CR^{3c}$, and $X^4$ is $CR^{3d}$, one of $R^{3a}$, $R^{3c}$, and $R^{3d}$ is selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, and the remaining two of $R^{3a}$, $R^{1c}$ and $R^{1d}$ are hydrogen. In some embodiments, $X^1$ is $CR^{3a}$, $X^2$ is N, $X^3$ is $CR^{3c}$, and $X^4$ is $CR^{3d}$, and $R^{3a}$, $R^{1c}$ and $R^{1d}$ are hydrogen.

In some embodiments, $X^1$ is N, $X^2$ is $CR^{3b}$, $X^3$ is N, and $X^4$ is $CR^{3d}$, one of $R^{3b}$ and $R^{3d}$ is selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, and the other is hydrogen. In some embodiments, $X^1$ is N, $X^2$ is $CR^{3b}$, $X^3$ is N, $X^4$ is $CR^{3d}$, and $R^{3b}$ and $R^{1d}$ are hydrogen.

In some embodiments, $X^1$ is $CR^{3a}$, $X^2$ is $CR^{3b}$, $X^3$ is $CR^{3c}$, and $X^4$ is $CR^{3d}$, and one of $R^{3a}$, $R^{3b}$, $R^{3c}$ and $R^{3d}$ is selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, and the remaining three of $R^{3a}$, $R^{3b}$, $R^{3c}$ and $R^{3d}$ are hydrogen. In some embodiments, $X^1$ is $CR^{3a}$, $X^2$ is $CR^{3b}$, $X^3$ is $CR^{3c}$, and $X^4$ is $CR^{3d}$, and $R^{3a}$, $R^{3b}$, $R^{3c}$ and $R^{3d}$ are hydrogen.

In some embodiments, the group

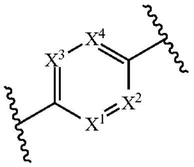

has a formula selected from:

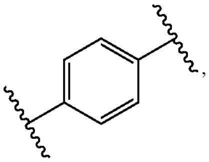,
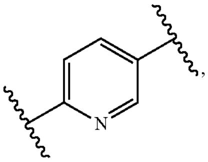,
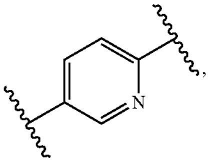,
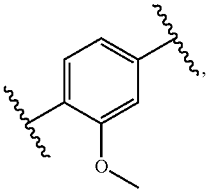,
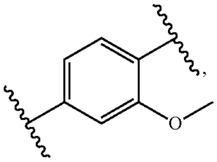,
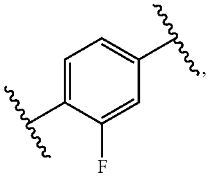,
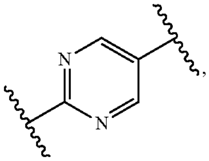,
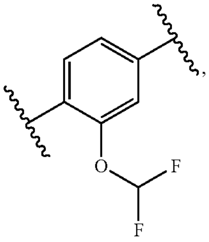, -continued

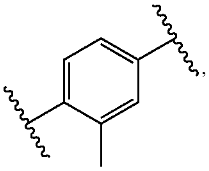,
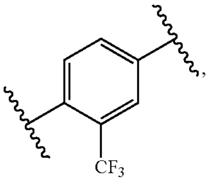,
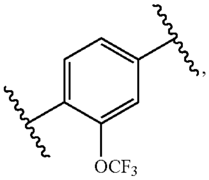,
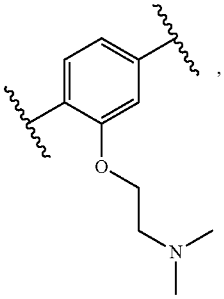,
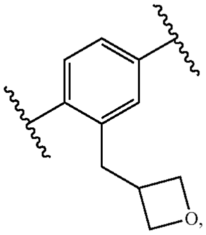
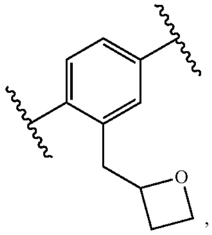,
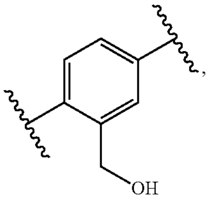,
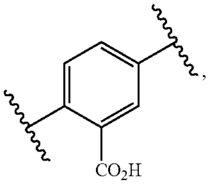,
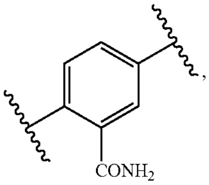, and
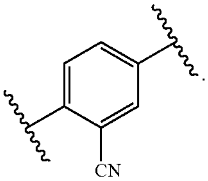.

In some embodiments, the group

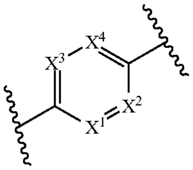

has a formula selected from:

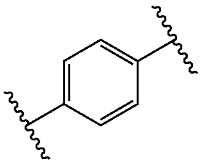 and
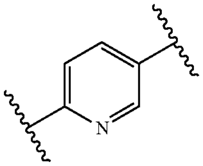

In some embodiments, $R^4$ is selected from: 5-membered monocyclic heteroaryl having 1, 2, 3, or 4 nitrogen atoms, which is unsubstituted or substituted with 1 or 2 substituents independently selected from $C_1$-$C_3$ alkyl; a 4-, 5- or 6-membered monocyclic heterocyclyl having 1, 2, or 3 heteroatoms independently selected from N and O, which is unsubstituted or substituted with 1 or 2 substituents independently selected from oxo and thioxo; cyano; —$CH_2NR^{4a}R^{4b}$; and —$C(O)NR^{4a}R^{4b}$; wherein $R^{4a}$ and $R^{4b}$ are each independently selected from hydrogen and methyl. In some embodiments, $R^4$ is a 5-membered monocyclic heteroaryl selected from pyrazolyl, imidazolyl, triazolyl, and tetrazolyl, each of which is independently unsubstituted or substituted with one substituent selected from $C_1$-$C_3$ alkyl. In some embodiments, $R^4$ is a 5-membered monocyclic heteroaryl selected from pyrazolyl and imidazolyl, each of which is independently unsubstituted or substituted with one substituent selected from $C_1$-$C_3$ alkyl (e.g., methyl). In some embodiments, $R^4$ is a 4-, 5-, or 6-membered heterocyclyl selected from azetidinyl, pyrrolidinyl, piperidinyl, piperazinyl, dihydropyrrolyl, dihydrotriazolyl, dihydrooxadiazolyl, and dihydropyridinyl, each of which is independently unsubstituted or substituted with one substituent selected from oxo and thioxo. In some embodiments, $R^4$ is a 4-, 5- or 6-membered heterocyclyl selected from azetidinyl, pyrrolidinyl, piperidinyl, piperazinyl, dihydropyrrolyl, dihydrotriazolyl, dihydrooxadiazolyl, and dihydropyridinyl, each of which is independently unsubstituted or substituted with one substituent selected from oxo and thioxo. In some embodiments, $R^4$ is a 4-, 5- or 6-membered heterocyclyl selected from azetidinyl, pyrrolidinyl, and piperazinyl, each of which is independently unsubstituted or substituted with one substituent selected from oxo and thioxo. In some embodiments, $R^4$ is selected from cyano, —$CH_2NR^{4a}R^{4b}$, and —$C(O)NR^{4a}R^{4b}$; wherein $R^{4a}$ and $R^{4b}$ are each hydrogen. In some embodiments, $R^4$ is cyano. In some embodiments, $R^4$ is —$CH_2NR^{4a}R^{4b}$ or —$C(O)NR^{4a}R^{4b}$; wherein $R^{4a}$ and $R^{4b}$ are each hydrogen.

In some embodiments, $R^4$ is selected from:

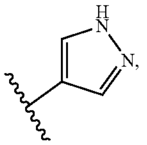 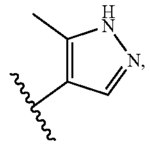 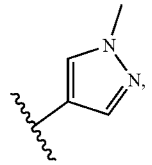

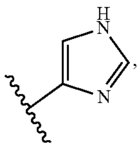 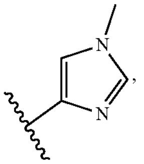 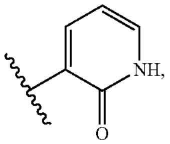

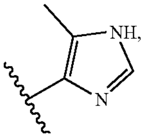 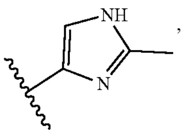 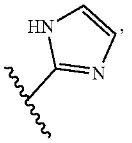

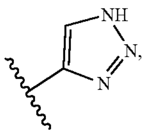 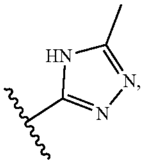 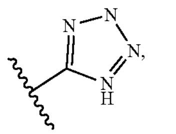

-continued

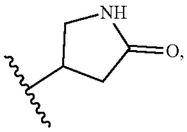 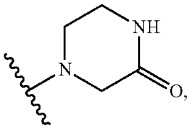 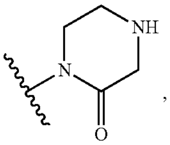

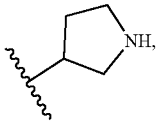 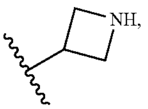 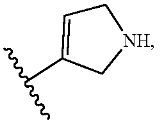

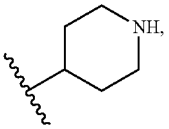 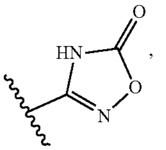 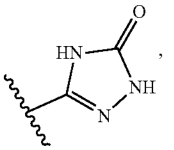

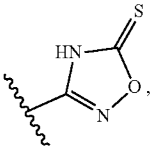  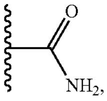

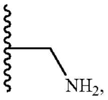 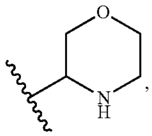

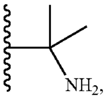 and 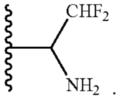 .

In some embodiments, $R^4$ is selected from:

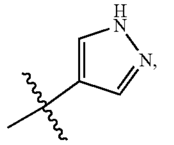 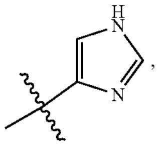

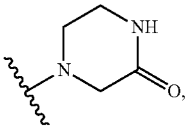

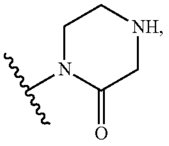

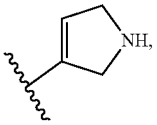 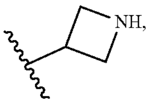

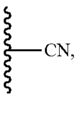 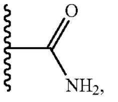 and 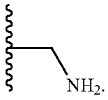

In some embodiments, $R^4$ is selected from:

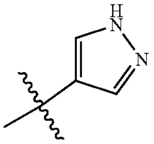

and

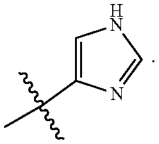 [SMILES: *c1c[nH]cn1]

In some embodiments, $R^4$ is:

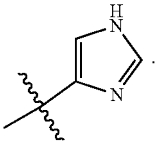

In some embodiments, A is selected from: a 5-membered monocyclic heteroaryl having 1, 2, 3, or 4 nitrogen atoms, which is unsubstituted or substituted with 1 or 2 substituents independently selected from $C_1$-$C_3$ alkyl; and a 4-, 5-, or 6-membered heterocyclyl having 1, 2, or 3 heteroatoms independently selected from N and O, which is unsubstituted or substituted with 1 or 2 substituents independently selected from oxo and thioxo. In some embodiments, A is a 5-membered monocyclic heteroaryl selected from pyrazolyl, imidazolyl, triazolyl, and tetrazolyl, each of which is independently unsubstituted or substituted with one substituent selected from $C_1$-$C_3$ alkyl, or A is a 4-, 5-, or 6-membered heterocyclyl selected from azetidinyl, pyrrolidinyl, piperidinyl, dihydropyrrolyl, dihydrotriazolyl, dihydrooxadiazolyl, and dihydropyridinyl, each of which is independently unsubstituted or substituted with one substituent selected from oxo and thioxo. In some embodiments, A is a 5-membered monocyclic heteroaryl selected from pyrazolyl, imidazolyl, triazolyl, and tetrazolyl, each of which is independently unsubstituted or substituted with one substituent selected from $C_1$-$C_3$ alkyl (e.g., methyl). In some embodiments, A is a 5-membered monocyclic heteroaryl selected from pyrazolyl and imidazolyl, each of which is independently unsubstituted or substituted with one substituent selected from $C_1$-$C_3$ alkyl (e.g., methyl). In some embodiments, A is a 4-, 5-, or 6-membered heterocyclyl selected from azetidinyl, pyrrolidinyl, piperidinyl, dihydropyrrolyl, dihydrotriazolyl, dihydrooxadiazolyl, and dihydropyridinyl, each of which is independently unsubstituted or substituted with one substituent selected from oxo and thioxo. In some embodiments, A is a 4-, 5- or 6-membered heterocyclyl selected from azetidinyl, pyrrolidinyl, and piperazinyl, each of which is independently unsubstituted or substituted with one substituent selected from oxo and thioxo.

In some embodiments, A is selected from:

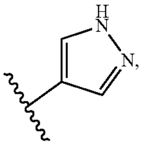
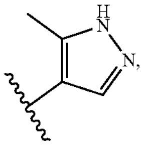
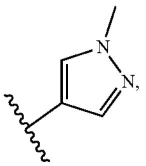
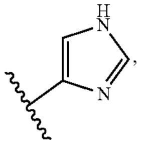
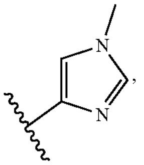
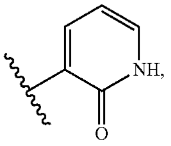

-continued

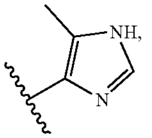
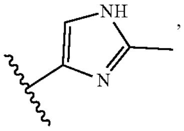
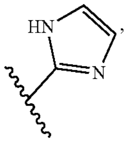
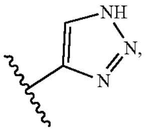
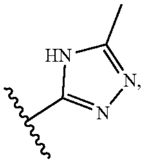
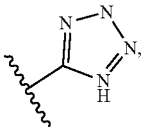
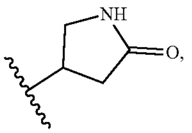
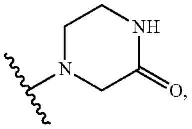
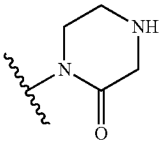
,
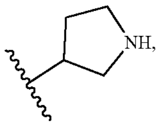
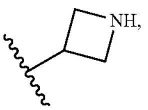
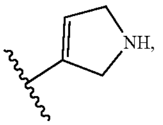
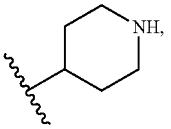
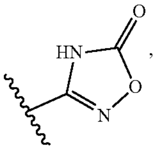
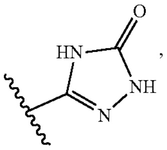

and

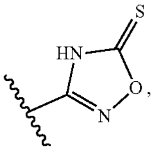

In some embodiments, A is selected from:

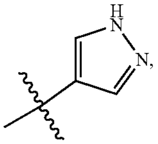
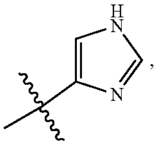
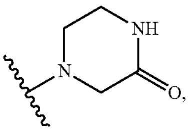
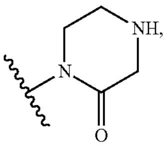
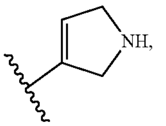

and

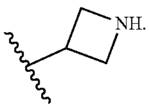

In some embodiments, A is selected from:
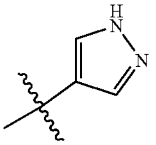
and
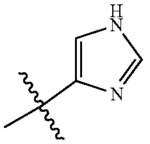
.
In some embodiments, A is
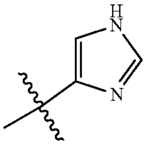
.
In some embodiments, the compound of formula (I) is selected from:
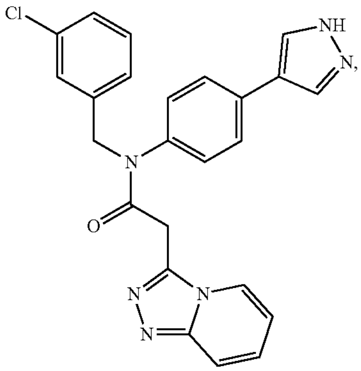
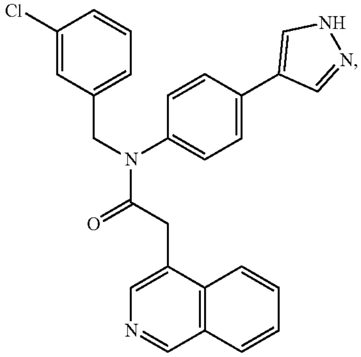
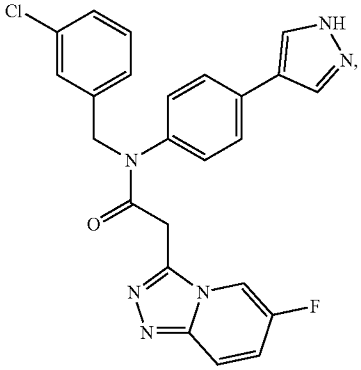
-continued
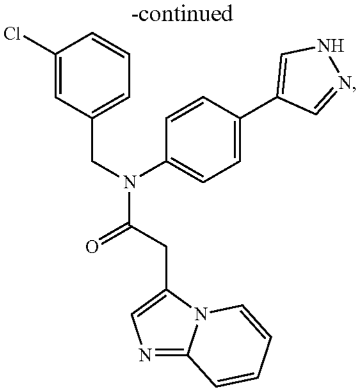
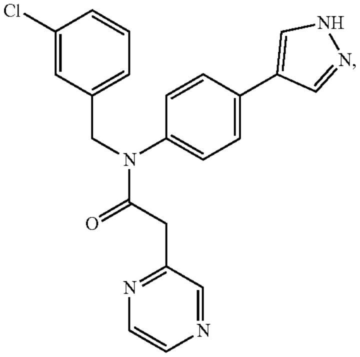
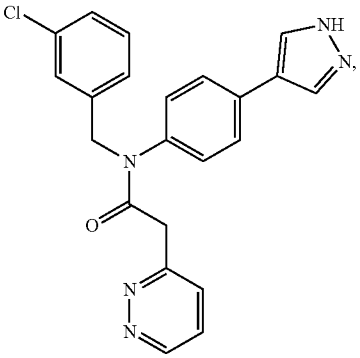
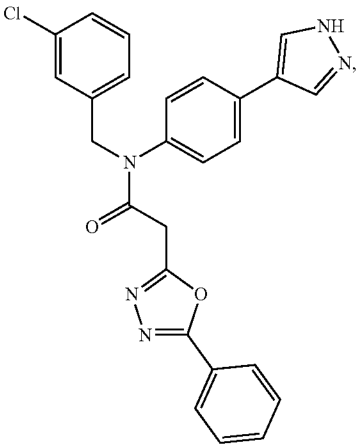

-continued
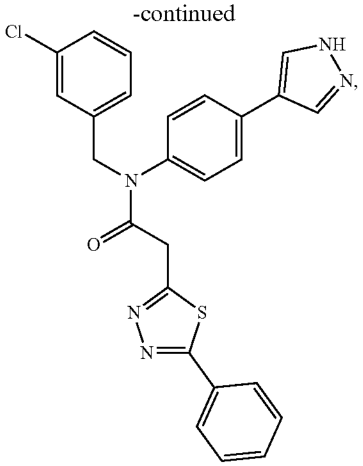
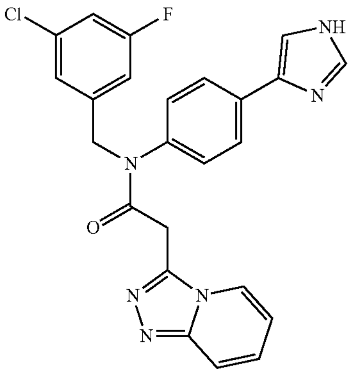
,
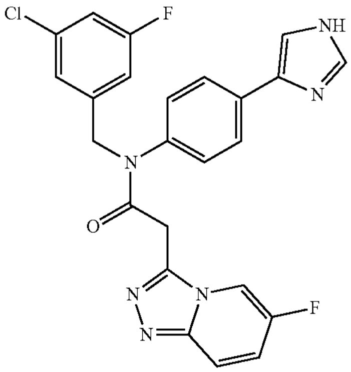
,
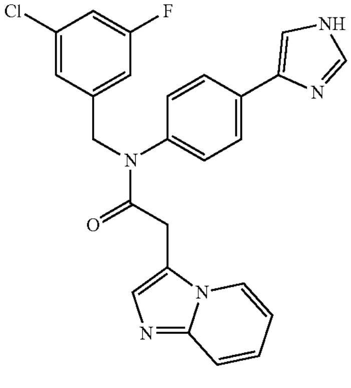
,
-continued
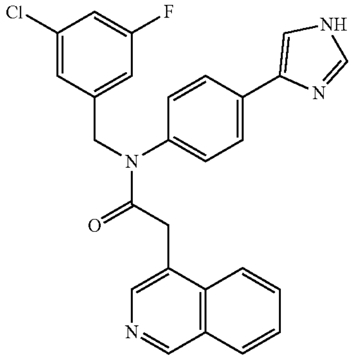
,
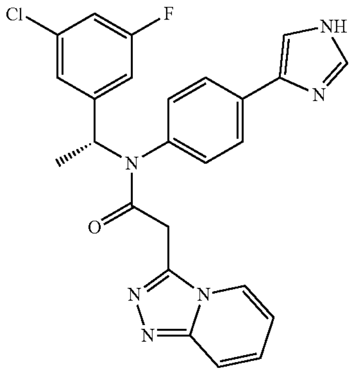
,
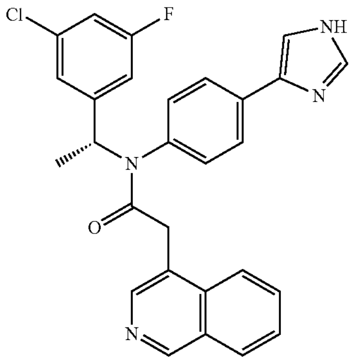
,
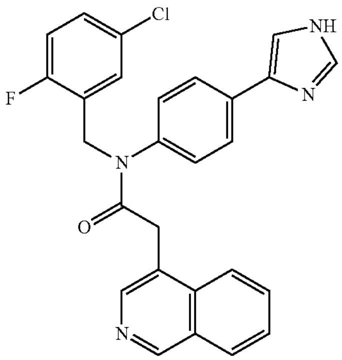
, -continued
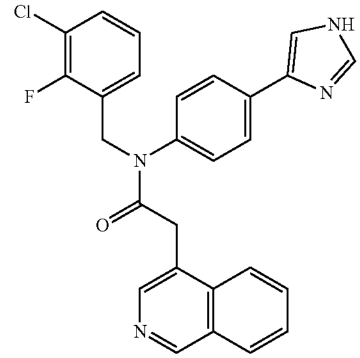
,
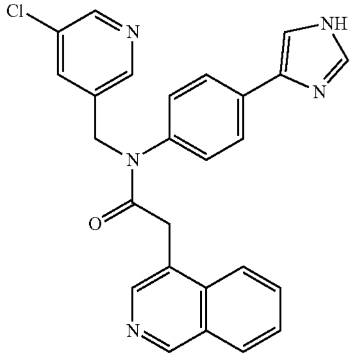
,
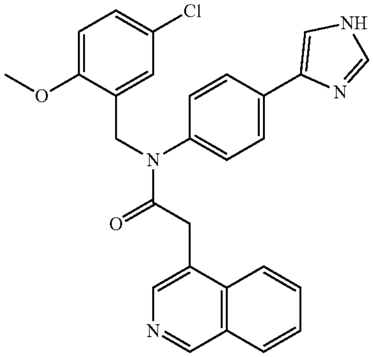
,
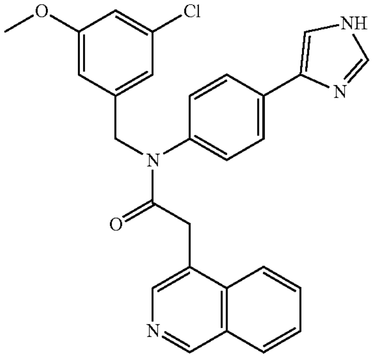
,
-continued
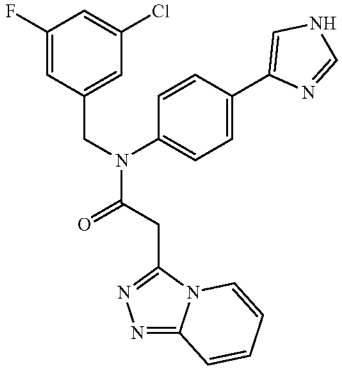
,
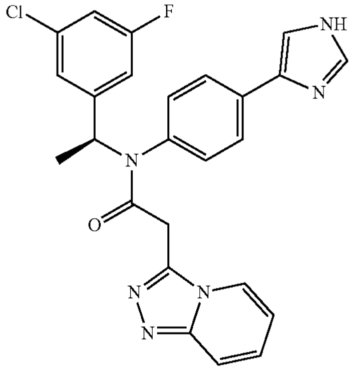
,
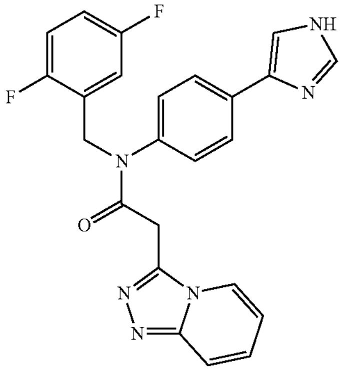
,
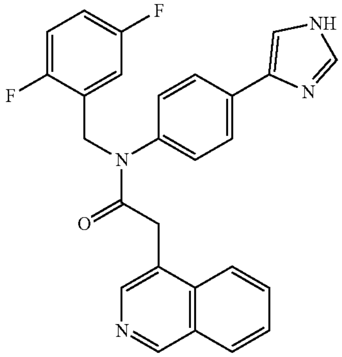
, -continued
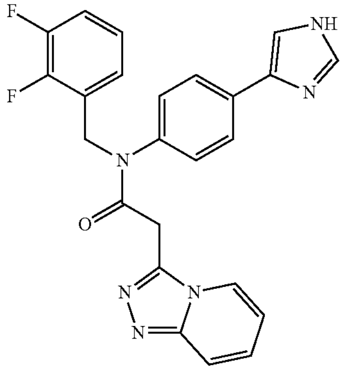
,
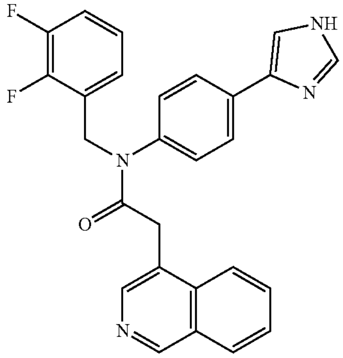
,
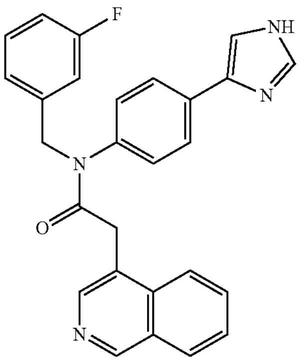
,
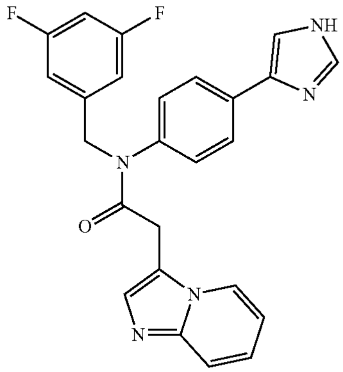
,
-continued
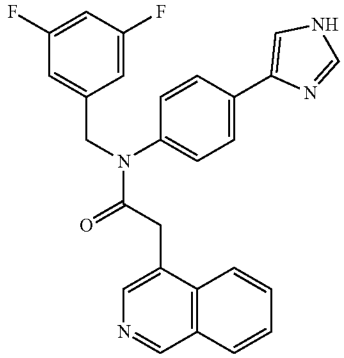
,
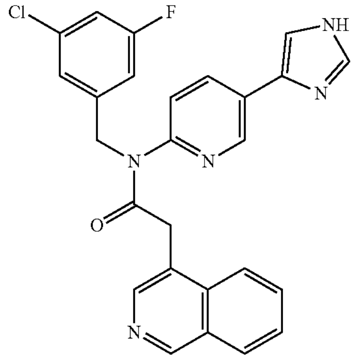
,
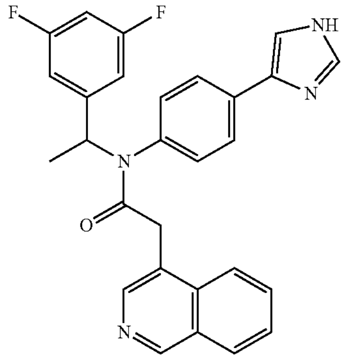
,
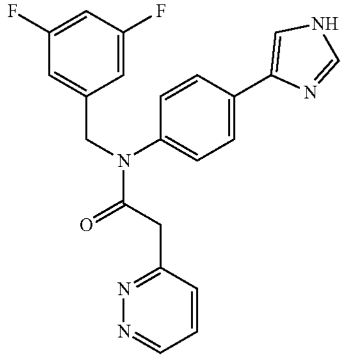
, -continued
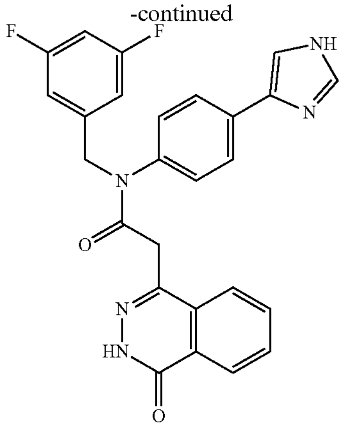
,
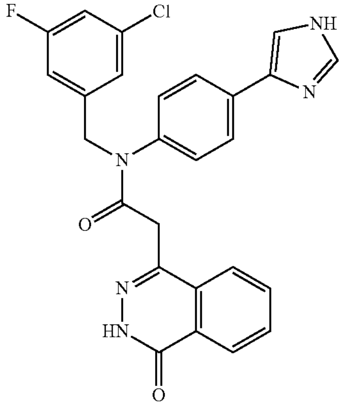
,
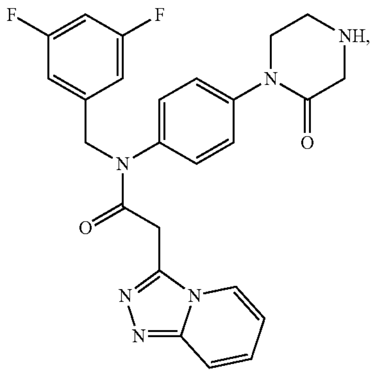
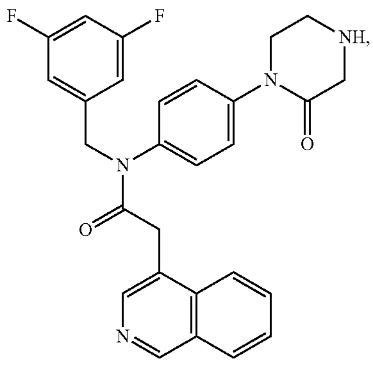
-continued
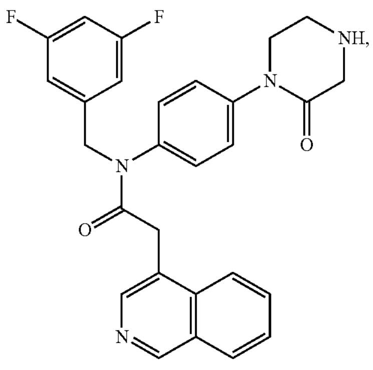
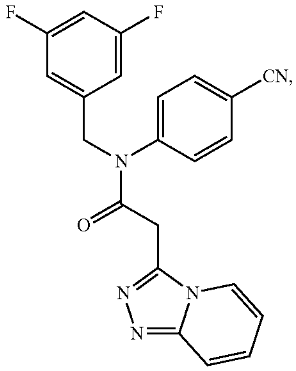
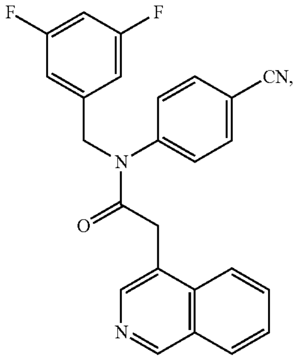
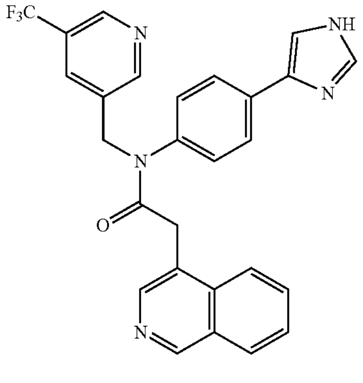
, -continued
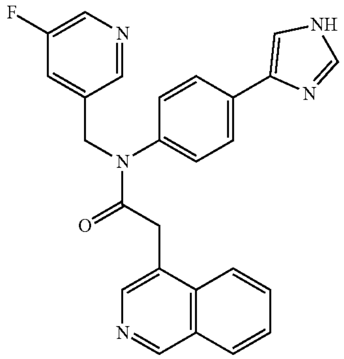
,
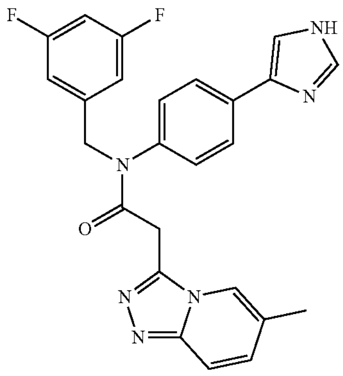
,
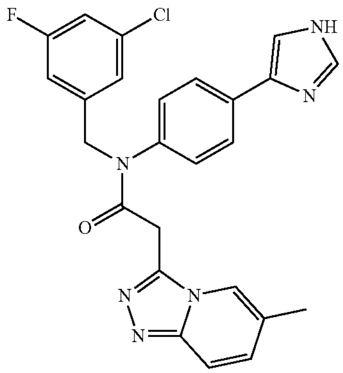
,
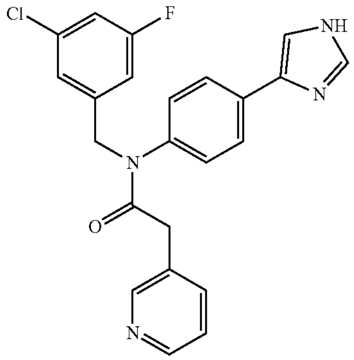
,
-continued
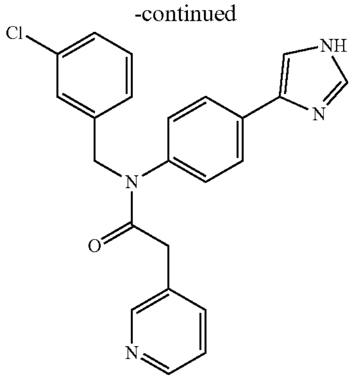
,
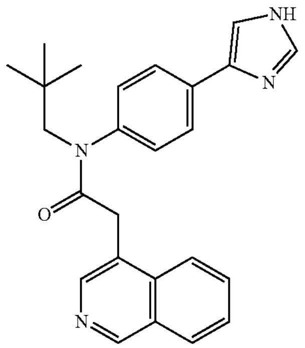
,
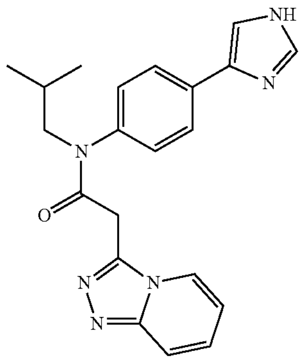
,
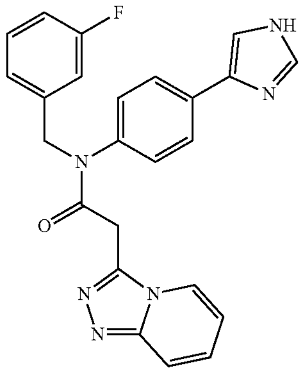
, -continued
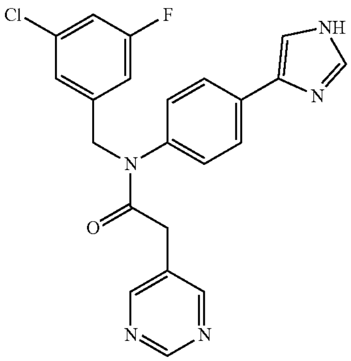
,
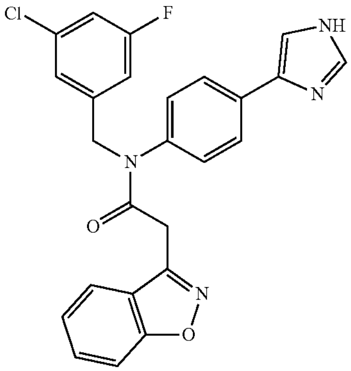
,
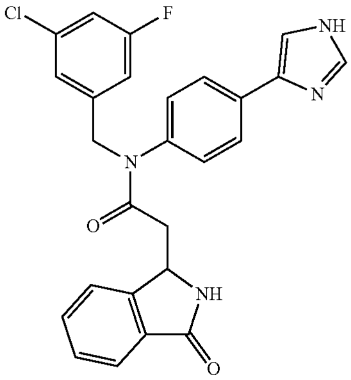
,
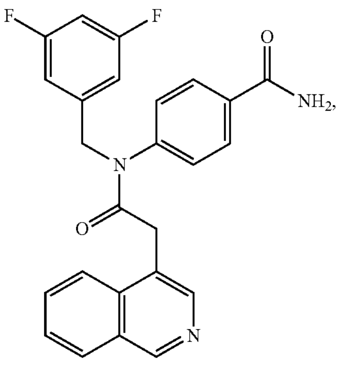
,
-continued
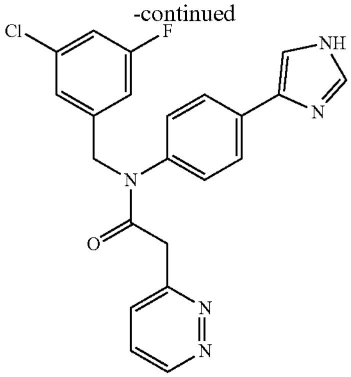
,
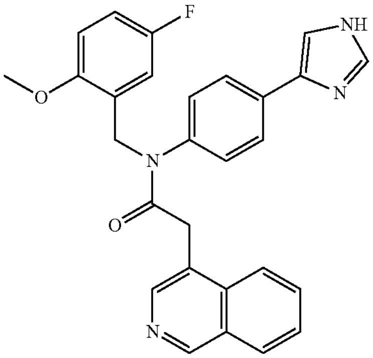
,
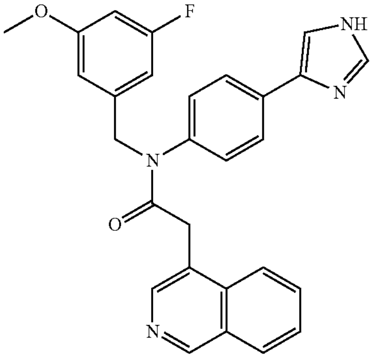
,
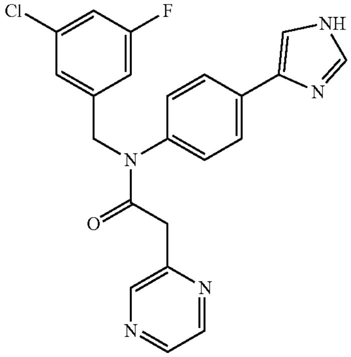
, -continued
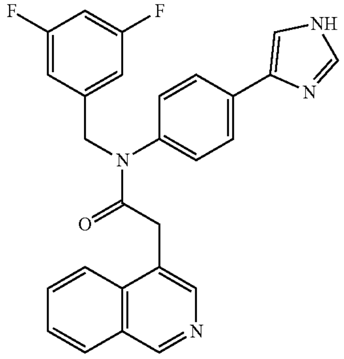
,
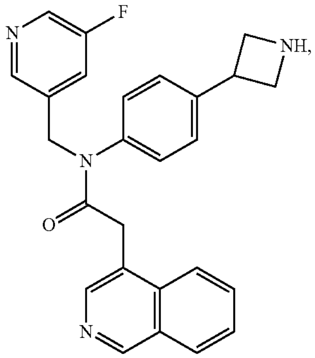
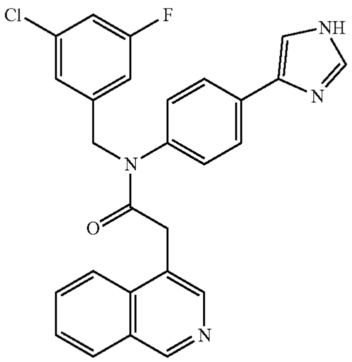
,
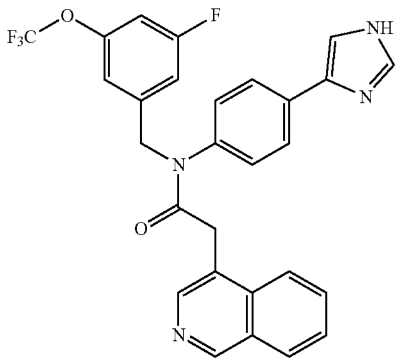
,
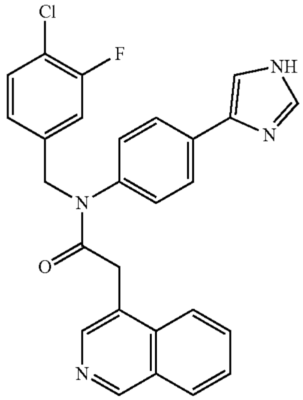
,
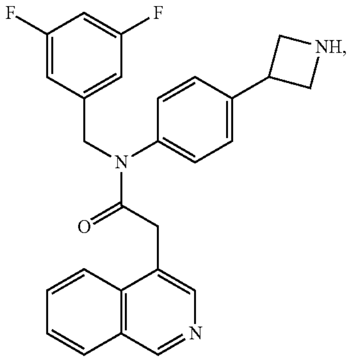
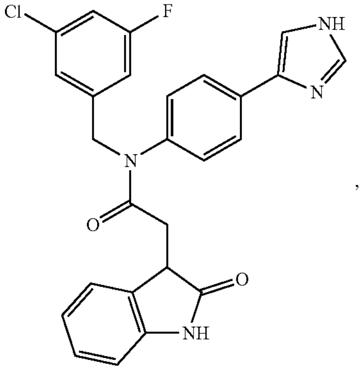
,
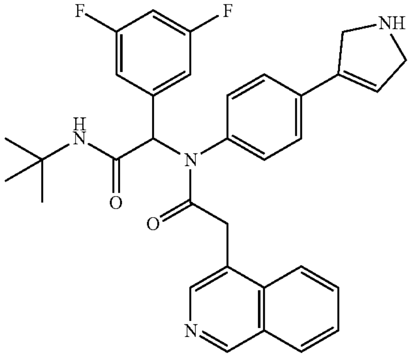
, -continued
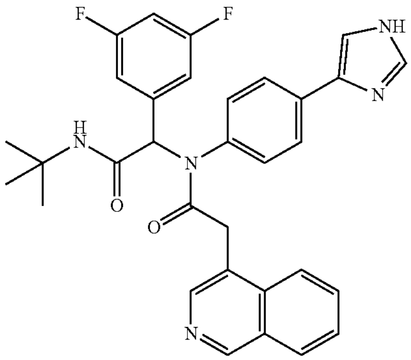
,
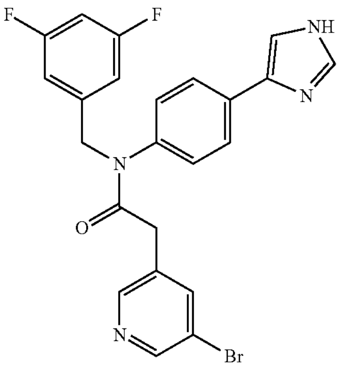
,
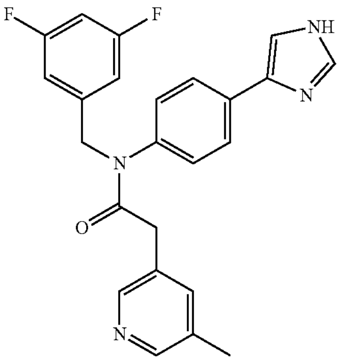
,
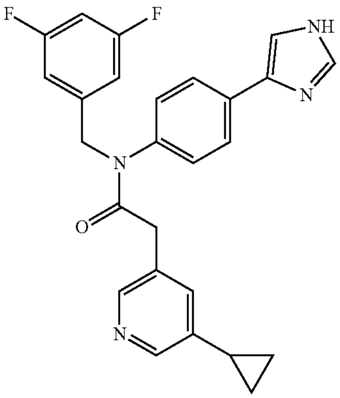
,
-continued
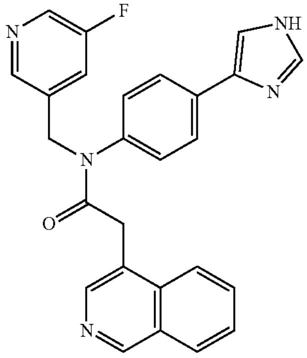
,
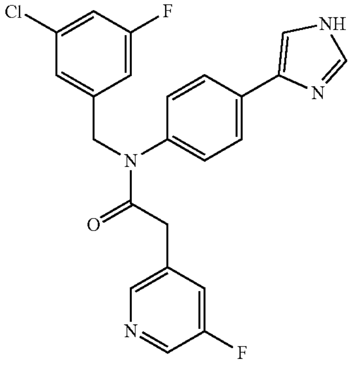
,
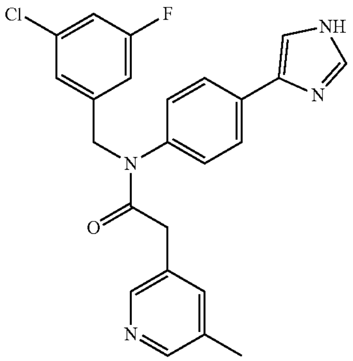
,
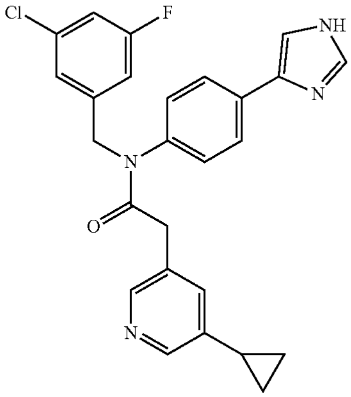
, -continued
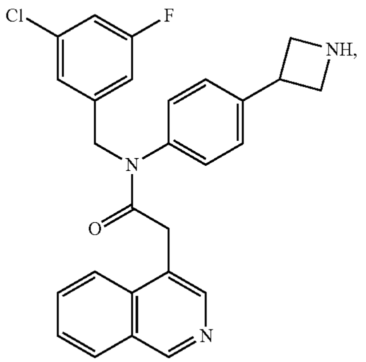
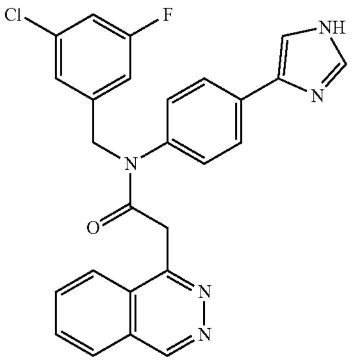
,
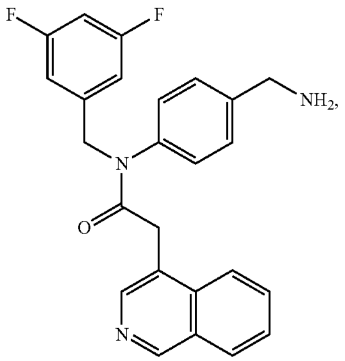
,
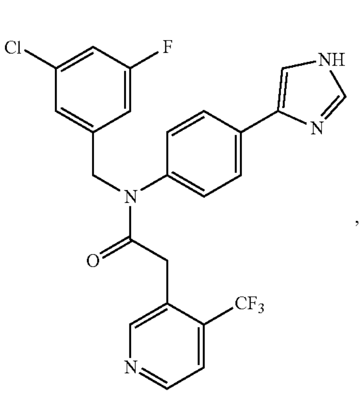
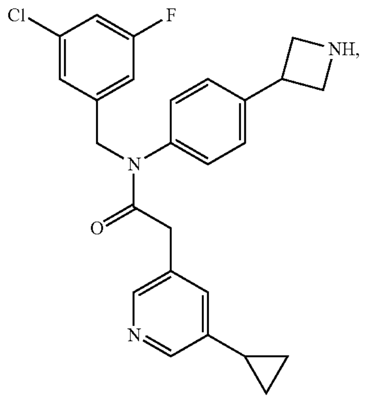
,
-continued
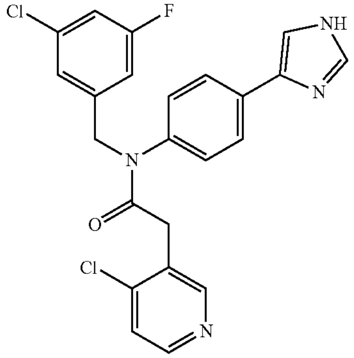
,
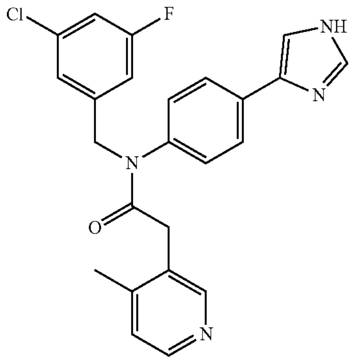
,
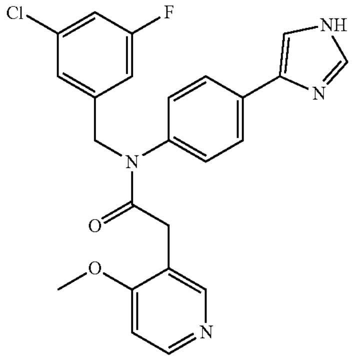
, -continued
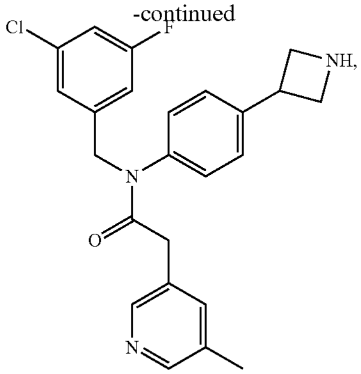
,
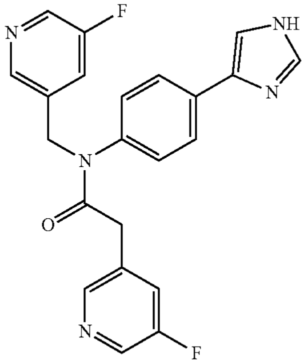
,
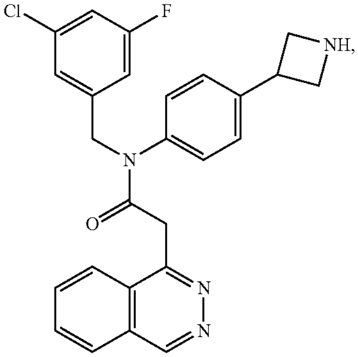
, and
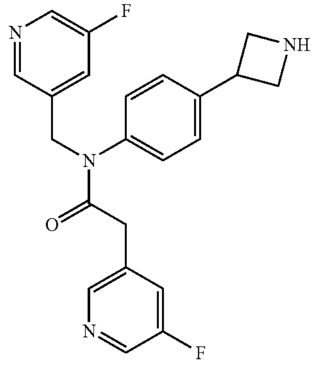
and pharmaceutically acceptable salts thereof.
Additional of formula (I) include:
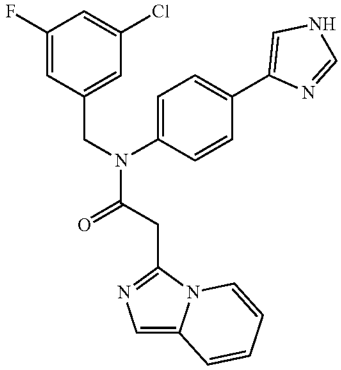
,
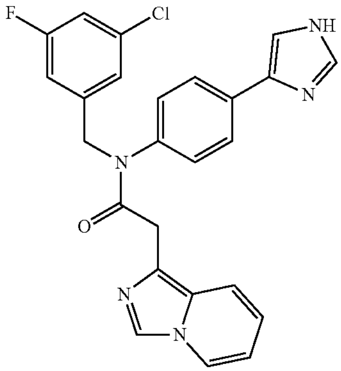
,
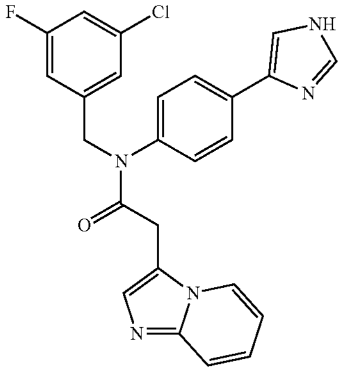
,
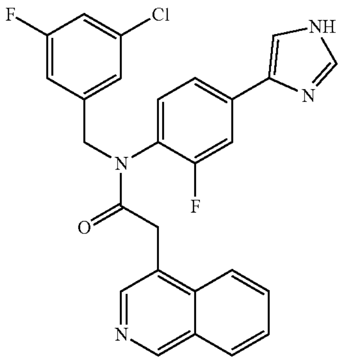
, -continued
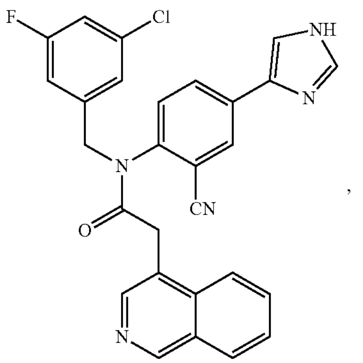
,
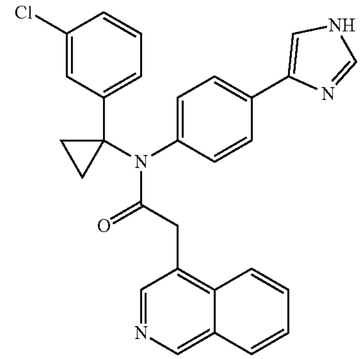
,
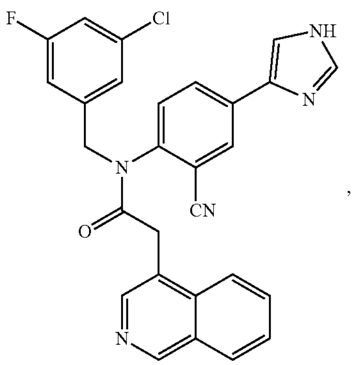
,
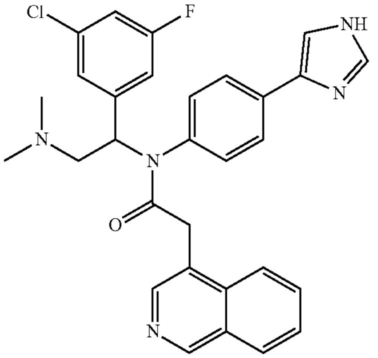
,
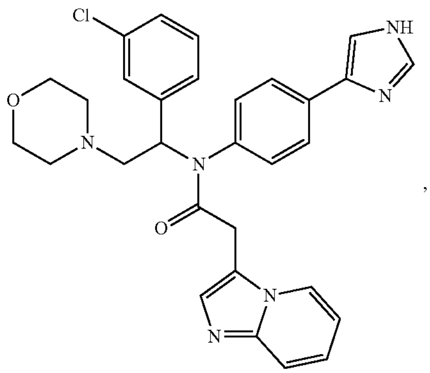
,
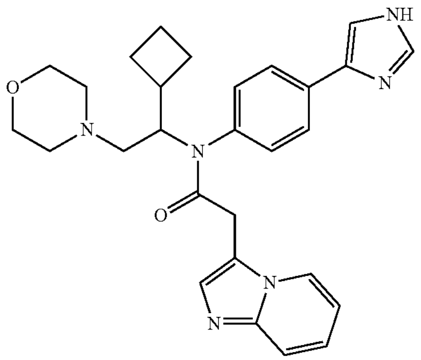
,
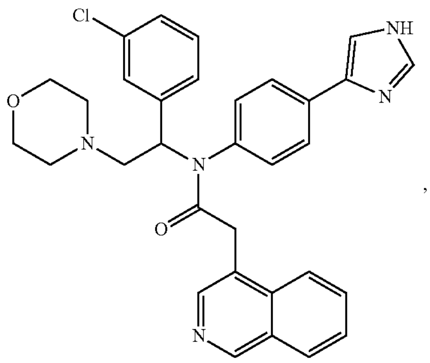
,
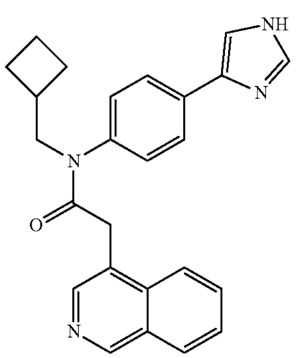
, -continued
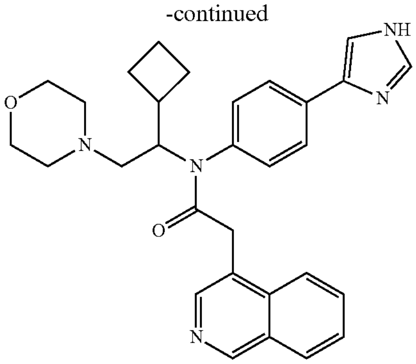
,
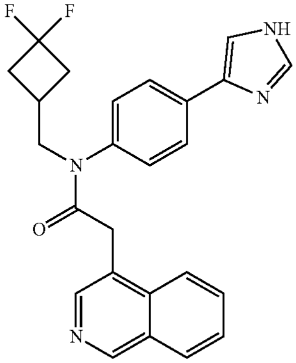
,
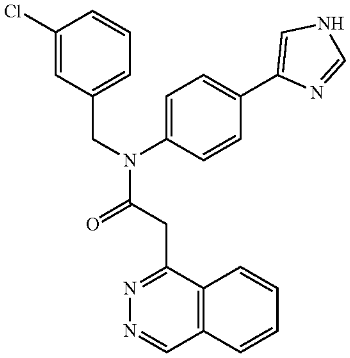
,
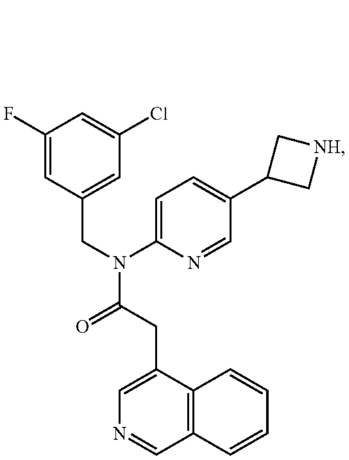
-continued
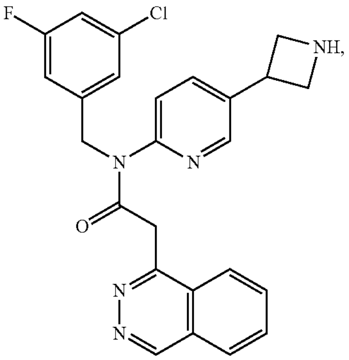
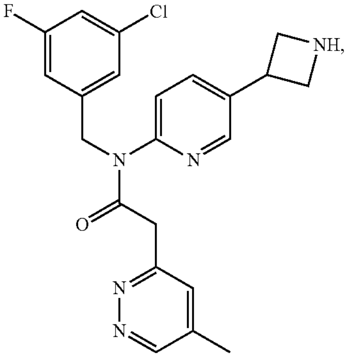
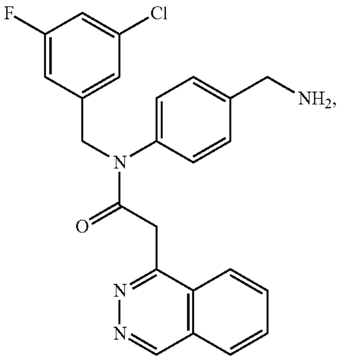
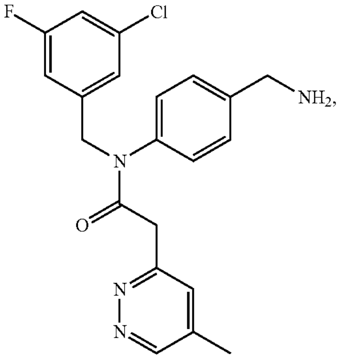

-continued

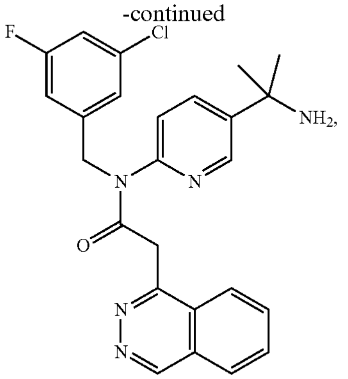

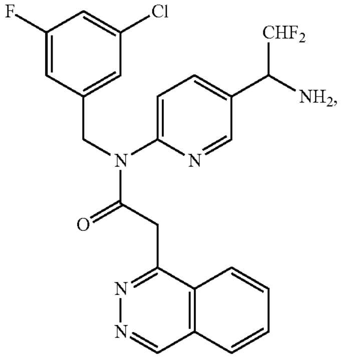

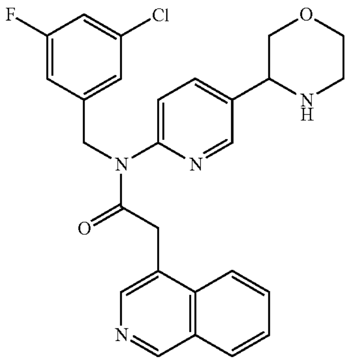

,

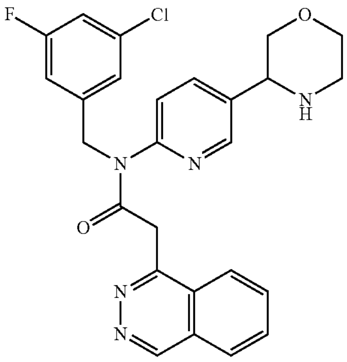

, and

-continued

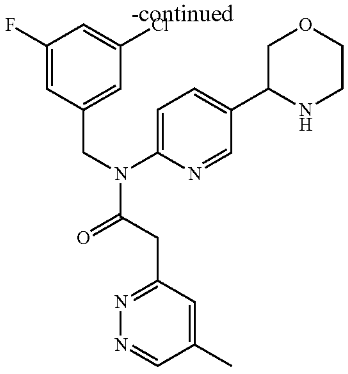

, and pharmaceutically acceptable salts thereof.

The compounds of the present disclosure may have at least one asymmetric center. Additional asymmetric centers may be present depending upon the nature of the various substituent groups. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this disclosure.

The independent syntheses of the enantiomerically or diastereomerically enriched compounds, or their chromatographic separations, may be achieved as known in the art by appropriate modification of the methodology disclosed herein. The absolute stereochemistry of a compound may be determined by using X-ray crystallography to determine the crystal structure of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

The compound (e.g., a compound of formula (I)) may possess tautomeric forms, and tautomers also constitute embodiments of the disclosure.

The present disclosure also includes isotopically-labeled compounds (e.g., an isotopically-labeled compound of formula (I)), which are identical to those recited in formula (I), but for the fact that one or more atoms are replaced by an atom having an atomic mass or mass number different from the atomic mass or mass number usually found in nature. Examples of isotopes suitable for inclusion in the compounds of the disclosure are hydrogen, carbon, nitrogen, oxygen, phosphorus, sulfur, fluorine, and chlorine, such as, but not limited to $^{2}H$, $^{3}H$ $^{13}C$, $^{14}C$ $^{15}N$, $^{18}O$, $^{31}P$, $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) or (II) are $^{11}C$, $^{13}N$, $^{15}O$, and $^{18}F$. Isotopically-labeled compounds of formula (I) or (II) can generally be prepared by conventional techniques known to those skilled in the art or by processes analogous to those described herein using an appropriate isotopically-labeled reagent in place of a non-isotopically-labeled reagent.

Compounds of formula (I) can be synthesized by a variety of methods, including those illustrated in the Examples. One approach is illustrated in Scheme 1, which involves reaction of an appropriate aniline with a suitable aldehyde via reductive amination, followed by coupling with an appropriate acid. The starting aniline compound may be prepared, e.g., via Suzuki-Miyaura cross-coupling.

Scheme 1

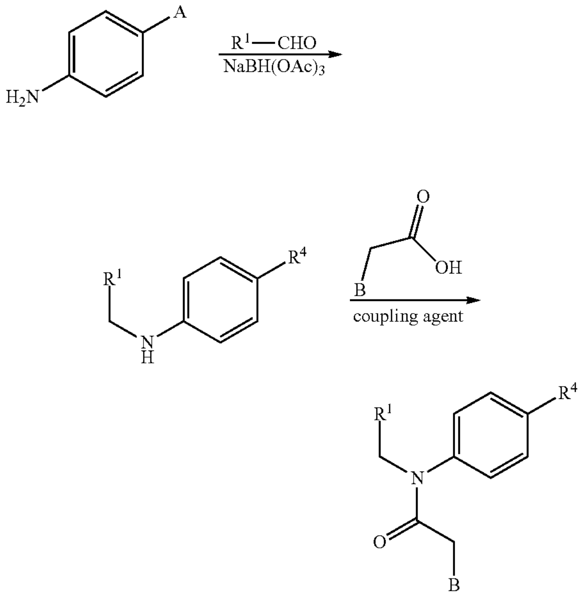

Another approach is illustrated in Scheme 2, which involves reaction of an appropriate aldehyde with a suitable aniline compound via reductive amination, followed by coupling with a suitable acid, and Suzuki-Miyaura cross-coupling with an appropriate boronic acid (or ester).

Scheme 2

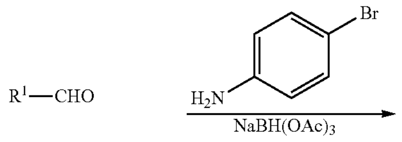

-continued

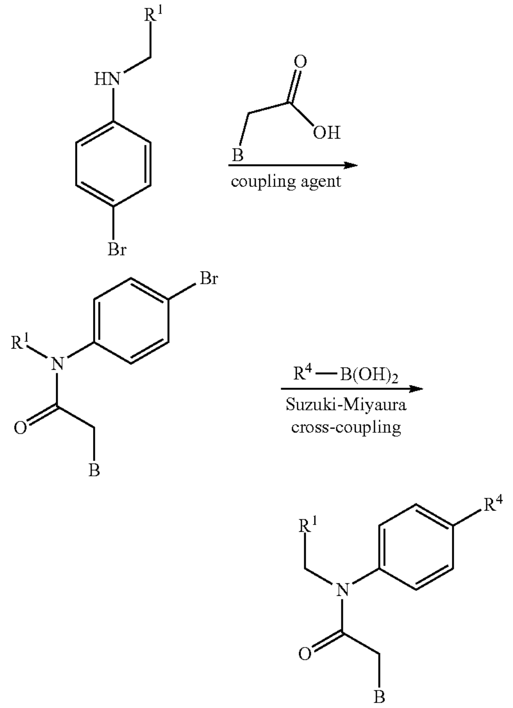

Another approach is illustrated in Scheme 3, which utilizes a reductive amination reaction as before with an appropriate aldehyde and aniline followed by coupling using 3-(tert-butoxy)-3-oxopropanoic acid. The resulting dicarbonyl compound is treated under basic conditions with 1-chlorophthalazine derivatives to afford the ester compound, which upon deprotection under acidic conditions affords the desired product.

Scheme 3

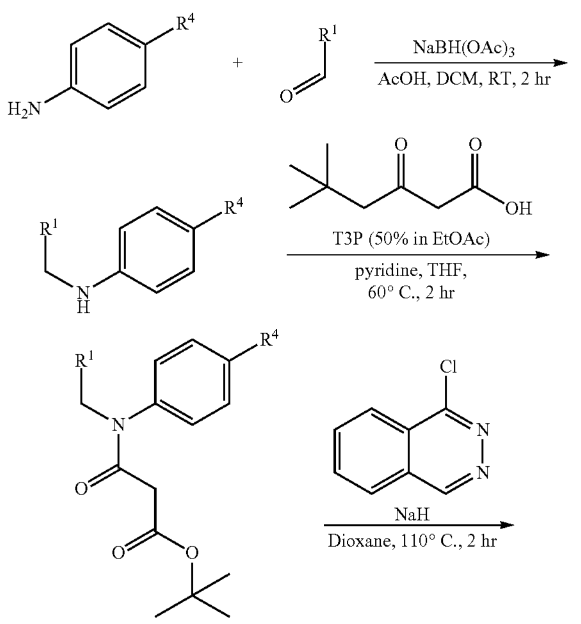

-continued

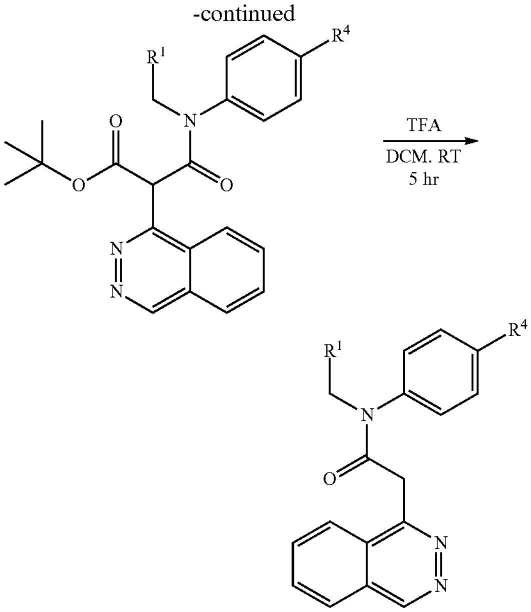

Compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Standard experimentation, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006).

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the procedures described herein using a pure geometric isomer as a starting material, or by resolution of a mixture of the geometric isomers of the compound or intermediates using a standard procedure such as chromatographic separation.

The synthetic schemes and specific examples as described are illustrative and are not to be read as limiting the scope of the disclosure or the claims. Alternatives, modifications, and equivalents of the synthetic methods and specific examples are contemplated.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, or allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl, and the like. In one embodiment, the compound is in the form of a trifluoroacetate salt.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Compounds disclosed herein can exist in unsolvated forms as well as solvated forms, including hydrated forms. In general, the solvated forms are equivalent to unsolvated forms and are encompassed within the scope of the present disclosure. Certain compounds of the disclosure may also exist in multiple crystalline or amorphous forms. In general, all physical forms are equivalent for the uses contemplated by the present disclosure and are intended to be within the scope of the present disclosure.

The present disclosure also provides compounds that are in a prodrug form. Prodrugs of the compounds described herein are those compounds that readily undergo chemical changes under physiological conditions to provide the compounds disclosed herein (e.g., a compound of formula (I)). Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Pharmaceutical Compositions

The disclosed compounds (e.g., compounds of formula (I)) may be incorporated into pharmaceutical compositions suitable for administration to a subject (such as a patient, which may be a human or non-human). The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the disclosure are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease or condition, the prophylactically effective amount will be less than the therapeutically effective amount.

For example, a therapeutically effective amount of a compound of formula (I) may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their pharmaceutically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerin, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)), and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this disclosure.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I), or a pharmaceutically acceptable salt thereof), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this disclosure are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

Methods of Use

The present disclosure provides methods of using the compounds and compositions described herein (e.g., compounds of formula (I) or pharmaceutically acceptable salts thereof). The methods include methods of treating a viral infection, and methods of inhibiting the replication of a virus, and methods of inhibiting a 3-chymotrypsin-like protease (3CLpro) in a sample.

Compounds described herein are potent inhibitors of 3CLpros, including 3CLpros from SARS-CoV and SARS-CoV-2. Accordingly, these compounds can be used in a method of inhibiting 3CLpro in a sample, such as a 3CLpro from SARS-CoV or SARS-CoV-2. Such methods comprise a step of contacting the sample with a compound of formula (I), or a composition comprising a compound of formula (I), in an amount effective to inhibit the 3CLpro in the sample.

Compounds described herein also have antiviral activity against SARS-CoV-2. Such activity can be assessed using several methods, including a cytopathic effect (CPE) inhibition assay (see, e.g., Shin et al. *Chemotherapy* 2016, 61 (3), 159-166), and in a plaque reduction assay (see, e.g., Shin et al. *MBio* 2018, 9 (6), 1-13).

Accordingly, in some embodiments, the disclosure provides a method of treating a viral infection in a subject in need thereof (e.g., a subject suffering from a viral infection), comprising administering to the subject a therapeutically effective amount of a compound described herein (e.g., a compound of formula (I), or a pharmaceutically acceptable salt thereof), or a pharmaceutical composition described herein (e.g., a pharmaceutical composition comprising a compound of formula (I) or a pharmaceutically acceptable salt thereof).

In another aspect, disclosed is a method of inhibiting viral replication in a sample, comprising contacting the sample with a compound described herein (e.g., a compound of formula (I) or a pharmaceutically acceptable salt thereof), or a pharmaceutical composition described herein (e.g., a pharmaceutical composition comprising a compound of formula (I) or a pharmaceutically acceptable salt thereof), in an amount effective to inhibit viral replication. In some embodiments, the virus is a coronavirus. In some embodiments, the step of contacting the sample with the compound comprising administering the compound to a subject suffering from a viral infection.

Other simple and convenient assays to determine if viral replication has been reduced include an ELISA assay for the presence, absence, or reduced presence of anti-viral antibodies in the sample (e.g., the blood of a subject) (Nasoff et al., *Proc. Natl. Acad. Sci.* 88:5462-5466, 1991), or RT-PCR (Yu et al., in Viral Hepatitis and Liver Disease 574-477, Nishioka, Suzuki and Mishiro (Eds.); Springer-Verlag Tokyo, 1994). Such methods are well known to those of ordinary skill in the art. Alternatively, total RNA from transduced and infected "control" cells can be isolated and subjected to analysis by dot blot or northern blot and probed with specific DNA to determine if viral replication is reduced. Alternatively, reduction of viral protein expression can also be used as an indicator of inhibition of viral replication. A greater than 50% reduction in viral replication as compared to control cells typically quantitates a prevention of viral replication.

i. Dosages

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

ii. Combination Therapies

A compound or composition described herein may be used in combination with other known therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound or composition described herein and the at least one additional therapeutic agent can be administered simultaneously, in the same or in separate compositions, or sequentially. For sequential administration, the compound described herein can be administered first, and the additional agent can be administered subsequently, or the order of administration can be reversed.

The compounds of the disclosure can also be used in combination with other drugs. For example, dosing a coronavirus-infected patient with a compound of the disclosure (e.g., a compound of formula (I)) and an interferon, such as interferon alpha, or a pegylated interferon, such as PEG-Intron or Pegasus, may provide a greater clinical benefit than dosing either the interferon, pegylated interferon or the compound alone. Examples of greater clinical benefits could include a larger reduction in symptoms, a faster time to alleviation of symptoms, reduced lung pathology, a larger reduction in the amount of coronavirus in the patient (viral load), and decreased mortality.

Coronaviruses infect cells which express p-glycoprotein, and some of the compounds of the disclosure may be p-glycoprotein substrates. Accordingly, such compounds may be dosed with a p-glycoprotein inhibitor, examples of which are verapamil, vinblastine, ketoconazole, nelfinavir, ritonavir, and cyclosporine. The p-glycoprotein inhibitors act by inhibiting the efflux of the compounds of the disclosure out of the cell. The inhibition of the p-glycoprotein based efflux will prevent reduction of intracellular concentrations of the compounds due to p-glycoprotein efflux. Dosing a coronavirus-infected patient with a compound of the disclosure and a p-glycoprotein inhibitor may lower the amount of SARS coronavirus 3CL protease inhibitor required to achieve an efficacious dose by increasing the intracellular concentration of the compound.

Among other agents that may be used to increase the exposure of a mammal to a compound of the present disclosure are those that can as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. The compounds of the disclosure include compounds that may be CYP3A4 substrates and may be metabolized by CYP3A4. Dosing a coronavirus-infected patient with a compound disclosed herein and a CYP3A4 inhibitor, such as ritonavir, nelfinavir or delavirdine, may reduce the metabolism of the compound by CYP3A4.

Other agents that may be used in combination with the compounds of the disclosure include other antiviral compounds (e.g., remdesivir, ritonavir, lopinavir, favipiravir, merimepodib), a corticosteroid (e.g., dexamethasone), anti-inflammatory drugs, and immune-based therapies (e.g., monoclonal antibodies or combinations thereof, such as bamlanivimab, casirivimab, imdevimab, AZD7442, VIR-7831, BRII-196 and BRII-198), or combinations thereof.

Kits

For use in the methods described herein, kits and articles of manufacture are also provided, which include a compound or pharmaceutical composition described herein (e.g., a compound of formula (I) or a pharmaceutically acceptable salt thereof, or a pharmaceutical composition comprising a compound of formula (I) or a pharmaceutically acceptable salt thereof). In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, in some embodiments the container(s) includes a compound of formula (I, or a pharmaceutically acceptable salt thereof, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

The following examples further illustrate aspects of the disclosure but, of course, should not be construed as in any way limiting its scope.

EXAMPLES

The following abbreviations are used in the Examples: "AcOH" means acetic acid, "DCE" means dichloroethane, "DCM" means dichloromethane, "DIPEA" means N,N-diisopropylethylamine, "DMEM" means Dulbecco's Modified Eagle Medium, "DMF" means N,N-dimethylformamide, "DMSO" means dimethyl sulfoxide, "DMSO-$d_6$" means dimethyl sulfoxide (deuterated), "EtOAc" means ethyl acetate, "h" means hours, "HPLC" means high performance liquid chromatography, "KOAc" means potassium acetate, "LCMS" means liquid chromatography mass spectrometry, "$[M+H]^+$" means the protonated mass of the free base of the compound, "$NaBH(OAc)_3$" means sodium triacetoxyborohydride, "NMR" means nuclear magnetic resonance, "$Pd(dppf)Cl_2.DCM$" means [1,1'-bis(diphenylphosphino)ferrocene]dichloropalladium(II) complex with dichloromethane, "$Pd(PPh_3)_4$" means tetrakis(triphenylphosphine)palladium(0), "r.t." means room temperature, "sat. aq." means saturated aqueous, "T3P" means propanephosphonic acid anhydride, "THF" means tetrahydrofuran, "$t_R$" means retention time, and "TRIS" means tris(hydroxymethyl)aminomethane.

General Chemical Experimentals

All chemical reagents and reaction solvents were purchased from commercial suppliers and used as received. Normal phase chromatography was performed on a Teledyne ISCO COMBIFLASH® NextGen300 flash chromatography system using Teledyne REDISEP® normal phase silica cartridges, with average particle size 35-70 micron. Preparative reversed-phase HPLC was performed using a Teledyne ACCQ-Prep HP150 equipped with Phenomenex KINETEX® C18 chromatography columns, using gradients of MeCN in $H_2O$ with 0.1% TFA additive. Compounds that are obtained as a TFA salt after purification were afforded as free base, by dissolving the salt in EtOAc and washing with sat. aq. $K_2CO_3$, or by elution through a Biotage ISOLUTE® SCX-II silica-based cartridge, loading and washing with MeOH and eluting with 2 N $NH_3$ in MeOH. Proton nuclear magnetic resonance (1H NMR) spectra were recorded 400 MHz on a Bruker spectrometer. For $^1H$ NMR spectra, chemical shifts are reported in parts per million (ppm) and are reported relative to residual non-deuterated solvent signals. Coupling constants are reported in hertz (Hz). The following abbreviations (or a combination, thereof) are used to describe splitting patterns: s, singlet; d, doublet; t, triplet; q, quartet; pent, pentet; m, multiplet; br, broad. Analytical thin layer chromatography (TLC) was performed on Kieselgel 60 F254 glass plates precoated with a 0.25 mm thickness of silica gel. TLC plates were visualized with UV light and iodine.

All compounds were of 95% purity or higher, unless otherwise noted, as measured by analytical reversed-phase HPLC. Mass spectra were obtained on an Agilent 1290 series 6230 TOF. Detection methods are diode array (DAD) at 210, 254 nm and positive/negative electrospray ionization (ESI), mass range 100-1200 m/z. All methods use an Agilent INFINITYLAB® POROSHELL® 120 EC-C18 chromatography column, dimensions 4.6×50 mm, 2.7 μm, fitted with POROSHELL® 120 EC-C18, 2.1 mm, 1.9 μm guard. Mobile phase A was 0.1% TFA in $H_2O$, mobile phase B was 0.1% TFA in MeCN. Method A: The mobile phase B was 5% for 0.2 min, then a gradient of 5-95% B over 2.0 min, then hold 0.45 min (0.4 mL/min flow rate), using positive ESI. Method B: The gradient was 40-95% B for 2.5 min, then hold 0.5 min (0.4 mL/min flow rate), using positive ESI. All reported LC-MS retention times and purities utilized method A unless stated otherwise.

General Assay and Characterization Experimentals

SARS-CoV-2 $3CL^{pro}$ Protein Expression & Purification

The SARS-CoV-2 $3CL^{pro}$ enzyme was cloned using previously published methods (Jin et al. *Nature* 2020, 582 (7811), 289-293; Xue et al. *J. Mol. Biol.* 2007, 366 (3), 965-975). Briefly, the gene encoding the protein was codon optimized for *E. coli*, synthesized, and inserted into a pGEX-6P-1 plasmid between the BamHI and XhoI cut sites (note that additional residues "AVLQ" and "GPHHHHHH-stop" were added to the N and C termini, respectively, of the protein as previously described). The resulting expression construct yielded an unscarred, native enzyme following protein purification.

The enzyme was recombinantly expressed using New England Biolabs T7 Express lysY/Iq cells transformed with $3CL^{pro}$ expression plasmids. The enzyme was expressed and purified using identical methods derived from the previously published work. Inoculated cultures of Luria Broth media supplemented with ampicillin were grown at 37° C. with shaking to a density of 0.6-0.8 $OD_{600nm}$. The incubator/shaker temperature was then reduced to 16° C. and the cultures were induced with 0.5 mM isopropyl β-D-1-thio-galactopyranoside (IPTG). Following overnight induction, cells were harvested via centrifugation at 3900 RPM (Eppendorf 5810R, S 4-104 rotor) for 25 minutes and resuspended in 20 mM TRIS, 300 mM NaCl pH 8.0 buffer (Buffer A). Resuspended cells were lysed via sonication, centrifuged at 10,500 RPM (Eppendorf 5810R, FA45-6-30 rotor) for 30 minutes, and the clarified lysate loaded onto a 5 mL Ni-charged Nuvia IMAC column equilibrated with Buffer A. The column was washed with 10 column volumes (CV) of Buffer A and eluted with a 7 CV gradient of 0-100% Buffer B (Buffer A+500 mM imidazole). Fractions containing pure $3CL^{pro}$ were pooled, diluted in half with Buffer A, and dialyzed overnight at 4° C. with PreScission Protease against a 50 mM TRIS, 150 mM NaCl, 1 mM DTT, pH 7.5 buffer. Cleaved protein was passed through a 5 mL Ni-charged Nuvia IMAC column equilibrated with a 50 mM TRIS, 150 mM NaCl pH 7.5 buffer. Collected flow through was concentrated to 5 mL using an Amicon Ultra 10 k centrifugal filter and diluted to 25 mL with 50 mM TRIS pH 7.5. Diluted protein was passed through a 5 mL HiTrap Q FF anion exchange column equilibrated with 50 mM TRIS, 25 mM NaCl buffer pH 7.5 (Buffer C). The Q FF column was washed with 10 CV of Buffer C and bound proteins eluted with a 5 CV 0-100% gradient of Buffer D (Buffer C+1 M NaCl). Pure $3CL^{pro}$ was found to be in the non-bound and wash fractions from this chromatographic step. Final purity was assessed via Coomassie stained SDS-PAGE; the pure protein was pooled, concentrated, aliquoted and frozen at −80° C. for biochemical assays.

Virus Propagation and Titration

The following reagent has been deposited by the Centers for Disease Control and Prevention and obtained through BEI Resources, NIAID, NIH: SARS-Related Coronavirus 2, Isolate USA-WA1/2020, NR-52281. The virus was propagated in Vero E6 expressing ACE2 receptor (provided by Dr. Younho Choi, Cleveland Clinic Lerner Research Institute) in a DMEM media supplemented with 1× penicillin-streptomycin (Gibco) and 0.5 μg/ml N-p-tosyl-L-phenylalanine chloromethyl ketone (TPCK)-treated trypsin (Worthington Biochemical) at 37° C. in a humidified incubator with 5% $CO_2$. Propagated virus was aliquoted and stored at −80° C. until further use.

The virus titer was determined by plaque assay as previously described with a slight modification (Shin et al. *MBio* 2018, 9 (6), 1-13). Briefly, confluent monolayer Vero E6 ACE2 cells cultured in a 6-well plate will be infected with 10-fold serial diluted virus inoculum incubated on a rocker for 45 min in 37° C. for virus adsorption. After the removal of virus solution, cells will be overlaid with DMEM containing 1% low melting agarose and incubated in a humidified incubator at 37° C. and 5% $CO_2$ for 4 days. To visualize the plaques, the cells will be fixed with 4% formaldehyde and stained with 0.2% crystal violet solution containing 20% ethanol.

Example 1: Preparation of Intermediate Compounds

Intermediate A: N-[(3-chlorophenyl)methyl]-4-(1-tetrahydropyran-2-ylpyrazol-4-yl)aniline

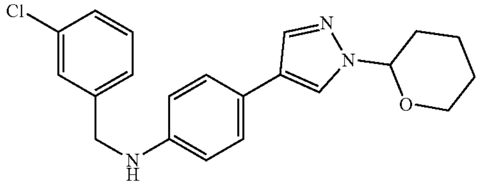 [SMILES: Clc1cccc(CNc2ccc(-c3cnn(C4CCCCO4)c3)cc2)c1]

4-bromo-N-[(3-chlorophenyl)methyl]aniline: To a solution of 3-chlorobenzaldehyde (1.45 mL, 12.8 mmol) and 4-bromoaniline (2.00 g, 11.6 mmol) in DCM (40 mL) and AcOH (2 mL), was added $NaBH(OAc)_3$ (3.7 g, 17.4 mmol) and the mixture stirred for 18 h at r.t. Sat. aq. $NaHCO_3$ (50 mL) was added and DCM layer separated. The aqueous layer was extracted with DCM (3×40 mL) and concentrated, purified by flash chromatography to afford 4-bromo-N-[(3-chlorophenyl)methyl]aniline (2.8 g, 9.3 mmol, 80%). LCMS (non-polar method) $t_R$=2.13 min, m/z=298.02 $[M+H]^+$.

N-[(3-chlorophenyl)methyl]-4-(1-tetrahydropyran-2-ylpyrazol-4-yl)aniline: 4-bromo-N-[(3-chlorophenyl)methyl]aniline (1.0 g, 3.4 mmol), 1-(Tetrahydro-2H-pyran-2-yl)-4-(4,4,5,5-tetramethyl-1,3,2-dioxaborolan-2-yl)-1H-pyrazole (1.4 g, 5.1 mmol) and $K_2CO_3$ (1.2 g, 8.4 mmol) were taken in 1,4-Dioxane (15 mL) and Water (1.5 mL) and purged with argon for 15 min. $Pd(dppf)Cl_2$.DCM (258 mg, 0.32 mmol) was added and the reaction heated in a sealed tube at 80° C. for 4.5 h. The reaction was allowed to cool to ambient temperature, diluted with EtOAc, filtered with celite, purified by flash chromatography to afford N-[(3-chlorophenyl)methyl]-4-(1-tetrahydropyran-2-ylpyrazol-4-yl)aniline (600 mg, 1.6 mmol, 48%). LCMS (non-polar method) $t_R$=1.28 min, m/z=368.13 $[M+H]^+$.

General Procedure a for Amide Coupling and Deprotection

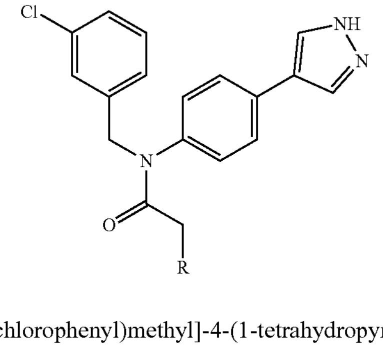

N-[(3-chlorophenyl)methyl]-4-(1-tetrahydropyran-2-ylpyrazol-4-yl)aniline (37 mg, 0.10 mmol) and acid (0.10 mmol) were taken in THE (1 mL). Diisopropylethylamine (0.05 mL, 0.30 mmol) and T3P (50% in EtOAc) (0.18 mL, 0.30 mmol) were added and the mixture heated to 60° C. for 1 h. The mixture was concentrated and the residue was dissolved in 4 M HCl in 1,4-dioxane (1 mL) and stirred at 60° C. for 1 h. After this time, the reaction mixture was concentrated and purified by HPLC to afford desired product.

Intermediate B: N-(3-chloro-5-fluorobenzyl)-4-(1-trityl-1H-imidazol-4-yl)aniline

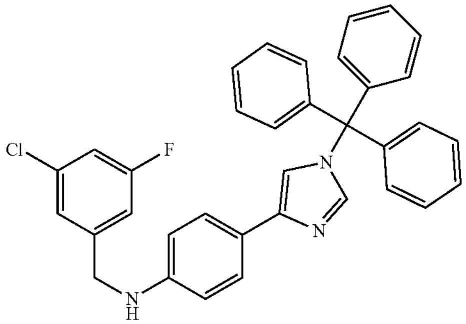 [SMILES: Fc1cc(Cl)cc(CNc2ccc(-c3cn(C(c4ccccc4)(c4ccccc4)c4ccccc4)cn3)cc2)c1]

4-bromo-N-(3-chloro-5-fluorobenzyl)aniline: To a solution of 3-Chloro-5-fluorobenzaldehyde (1.5 mL, 12.8 mmol) and 4-bromoaniline (2.00 g, 11.6 mmol) in DCM (40 mL) and AcOH (2 mL), was added $NaBH(OAc)_3$ (3.7 g, 17.4 mmol) and the mixture stirred for 18 h at r.t. Sat. aq. $NaHCO_3$ (50 mL) was added and DCM layer separated. The aqueous layer was extracted with DCM (3×40 mL) and concentrated, purified by flash chromatography to afford 4-bromo-N-[(3-chloro-5-fluoro-phenyl)methyl]aniline (3.5 g, 11.1 mmol, 96%). LCMS (non-polar method) $t_R$=2.23 min, m/z=315.97 [M+H]$^+$.

N-(3-chloro-5-fluorobenzyl)-4-(4,4,5,5-tetramethyl-1,3,2-dioxaborolan-2-yl)aniline: 4-bromo-N-(3-chloro-5-fluorobenzyl)aniline (2.0 g, 6.36 mmol), bis(pinacolato)diboron (1.93 g, 7.63 mmol) and KOAc (1.87 g, 19.07 mmol) were combined in 1,4-Dioxane (15 mL) and the mixture was stirred and purged with Ar. $Pd(dppf)Cl_2$.DCM (258 mg, 0.32 mmol) was added and the reaction heated in a sealed tube at 100° C. for 7 h. The reaction was allowed to cool to ambient temperature, diluted with EtOAc, filtered with celite, purified by flash chromatography to afford N-[(3-chloro-5-fluoro-phenyl)methyl]-4-(4,4,5,5-tetramethyl-1,3,2-dioxaborolan-2-yl)aniline (1.74 g, 4.81 mmol, 76%). LCMS (non-polar method) $t_R$=2.40 min, m/z=362.13 [M+H]$^+$.

N-(3-chloro-5-fluorobenzyl)-4-(1-trityl-1H-imidazol-4-yl)aniline: N-(3-chloro-5-fluorobenzyl)-4-(4,4,5,5-tetramethyl-1,3,2-dioxaborolan-2-yl)aniline (596 mg, 1.65 mmol), 4-Iodo-1-trityl-1H-imidazole (480 mg, 1.10 mmol) and Potassium phosphate tribasic (700 mg, 3.30 mmol) were taken in DMF (5 mL) and Water (1 mL) and purged with argon for 15 min. To the reaction mixture $Pd(PPh_3)_4$ (127 mg, 0.11 mmol) was added and heated to 90° C. for 4.5 h. Reaction mixture was diluted with EtOAc, filtered through celite and purified by flash chromatography to afford N-(3-chloro-5-fluorobenzyl)-4-(1-trityl-1H-imidazol-4-yl)aniline (500 mg, 0.92 mmol, 84%). $^1$H NMR (400 MHz, Chloroform-d) δ 7.58 (d, J=8.2 Hz, 2H), 7.39-7.33 (m, 10H), 7.20-7.11 (m, 8H), 7.00-6.92 (m, 3H), 6.58 (d, J=8.6 Hz, 2H), 4.34 (s, 2H). LCMS (non-polar method) $t_R$=1.95 min, m/z=302.08 [M−Trt+H]$^+$.

General Procedure B for Amide Coupling and Deprotection

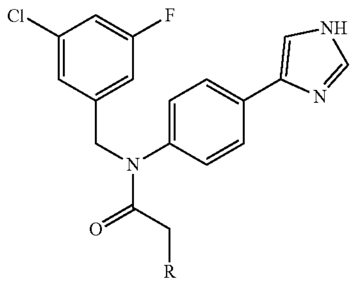

N-(3-chloro-5-fluorobenzyl)-4-(1-trityl-1H-imidazol-4-yl)aniline (37 mg, 0.10 mmol) and acid (0.10 mmol) were taken in THE (1 mL). Diisopropylethylamine (0.05 mL, 0.30 mmol) and T3P (50% in DMF) (0.18 mL, 0.30 mmol) were added and the mixture heated to 60° C. for 1 h. The mixture was concentrated and the residue was dissolved in Methanol (1 mL). To the reaction mixture AcOH (0.11 mL, 2 mmol) was added and it was then stirred at 60° C. for 1 h. After this time, the reaction mixture was concentrated and purified by HPLC to afford desired product. In the case of aminopyridine coupling partners (e.g., Compounds 20 and 29 below) amide bond formation can be accomplished using either $POCl_3$ in DCM:pyridine (4:1) at 0° C. for 1.5 h or alternatively Ghosez's reagent (1-chlor-N,N,2-trimethyl-1-propen-1-amin, 3.0 equiv) in the presence of DIPEA (5 equiv) in DCE for 16 h.

Example 2: Preparation of Compounds

N-[(3-chlorophenyl)methyl]-N-[4-(1H-pyrazol-4-yl)phenyl]-2-([1,2,4]triazolo[4,3-a]pyridin-3-yl)acetamide (Compound 1)

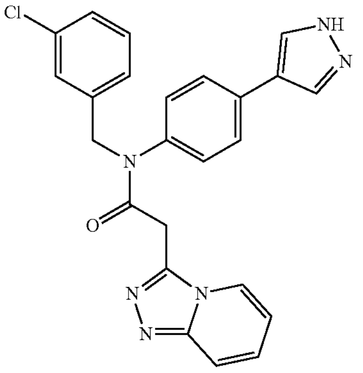 [SMILES: O=C(Cc1nnc2ccccn12)N(Cc1cccc(Cl)c1)c1ccc(-c2cn[nH]c2)cc1]

Prepared by general procedure A to afford N-[(3-chlorophenyl)methyl]-N-[4-(1H-pyrazol-4-yl)phenyl]-2-([1,2,4]triazolo[4,3-a]pyridin-3-yl)acetamide (9 mg, 0.02 mmol, 20%). $^1$H NMR (400 MHz, DMSO-d6) δ 12.97 (s, 1H), 8.41 (d, J=7.0 Hz, 1H), 8.16 (s, 1H), 7.99 (s, 1H), 7.71 (d, J=9.4 Hz, 1H), 7.66 (d, J=8.1 Hz, 2H), 7.39-7.27 (m, 6H), 7.22 (d, J=7.1 Hz, 1H), 6.96 (t, J=6.7 Hz, 1H), 4.90 (s, 2H), 4.17 (s, 2H). LCMS $t_R$=1.69 min, m/z=443.1394 [M+H]$^+$.

N-[(3-chlorophenyl)methyl]-2-(4-isoquinolyl)-N-[4-(1H-pyrazol-4-yl)phenyl]acetamide (Compound 2)

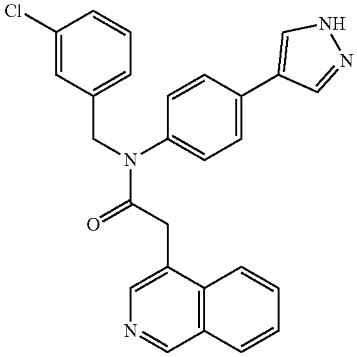 [SMILES: O=C(Cc1cncc2ccccc12)N(Cc1cccc(Cl)c1)c1ccc(-c2cn[nH]c2)cc1]

Prepared by general procedure A to afford N-[(3-chlorophenyl)methyl]-2-(4-isoquinolyl)-N-[4-(1H-pyrazol-4-yl)phenyl]acetamide (9 mg, 0.02 mmol, 20%). $^{1}$H NMR (400 MHz, DMSO-d6) δ 12.96 (s, 1H), 9.22 (s, 1H), 8.29-7.78 (m, 6H), 7.69 (dd, J=13.9, 7.7 Hz, 3H), 7.37-7.26 (m, 5H), 7.19 (d, J=6.6 Hz, 1H), 4.89 (s, 2H), 3.95 (s, 2H). LCMS $t_R$=1.75 min, m/z=453.1478 [M+H]$^+$.

N-[(3-chlorophenyl)methyl]-2-(6-fluoro-[1,2,4]triazolo[4,3-a]pyridin-3-yl)-N-[4-(1H-pyrazol-4-yl)phenyl]acetamide (Compound 3)

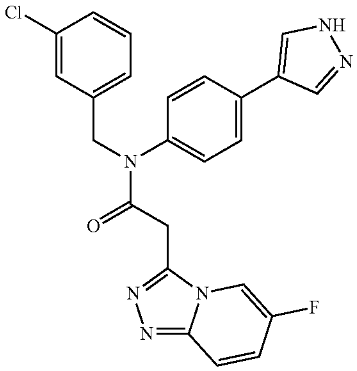 [SMILES: O=C(Cc1nnc2ccc(F)cn12)N(Cc1cccc(Cl)c1)c1ccc(-c2cn[nH]c2)cc1]

Prepared by general procedure A to afford N-[(3-chlorophenyl)methyl]-2-(6-fluoro-[1,2,4]triazolo[4,3-a]pyridin-3-yl)-N-[4-(1H-pyrazol-4-yl)phenyl]acetamide (13 mg, 0.03 mmol, 28%). $^{1}$H NMR (400 MHz, DMSO-d6) δ 12.96 (s, 1H), 8.33 (d, J=7.0 Hz, 1H), 8.20 (s, 1H), 7.93 (s, 1H), 7.66 (d, J=8.0 Hz, 2H), 7.55 (d, J=9.1 Hz, 1H), 7.35-7.22 (m, 7H), 7.20 (d, J=6.9 Hz, 1H), 6.95 (t, J=6.9 Hz, 1H), 4.89 (s, 2H), 3.93 (s, 2H). LCMS $t_R$=1.80 min, m/z=461.1291 [M+H]$^+$.

N-[(3-chlorophenyl)methyl]-2-imidazo[1,2-a]pyridin-3-yl-N-[4-(1H-pyrazol-4-yl)phenyl]acetamide (Compound 4)

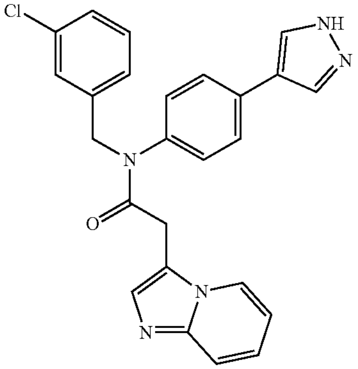 [SMILES: O=C(Cc1cnc2ccccn12)N(Cc1cccc(Cl)c1)c1ccc(-c2cn[nH]c2)cc1]

Prepared by general procedure A to afford N-[(3-chlorophenyl)methyl]-2-imidazo[1,2-a]pyridin-3-yl-N-[4-(1H-pyrazol-4-yl)phenyl]acetamide (13 mg, 0.03 mmol, 29%). $^{1}$H NMR (400 MHz, DMSO-d6) δ 12.96 (s, 1H), 8.33 (d, J=7.0 Hz, 1H), 8.20 (s, 1H), 7.93 (s, 1H), 7.66 (d, J=8.0 Hz, 2H), 7.55 (d, J=9.1 Hz, 1H), 7.35-7.22 (m, 7H), 7.20 (d, J=6.9 Hz, 1H), 6.95 (t, J=6.9 Hz, 1H), 4.89 (s, 2H), 3.93 (s, 2H). LCMS $t_R$=1.70 min, m/z=442.1442 [M+H]$^+$.

N-[(3-chlorophenyl)methyl]-2-pyrazin-2-yl-N-[4-(1H-pyrazol-4-yl)phenyl]acetamide (Compound 5)

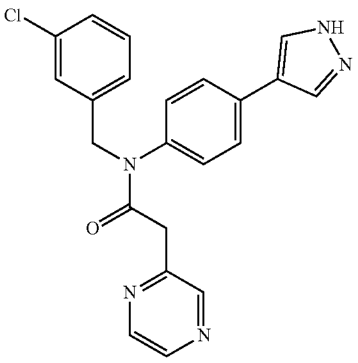 [SMILES: O=C(Cc1cnccn1)N(Cc1cccc(Cl)c1)c1ccc(-c2cn[nH]c2)cc1]

Prepared by general procedure A to afford N-[(3-chlorophenyl)methyl]-2-pyrazin-2-yl-N-[4-(1H-pyrazol-4-yl)phenyl]acetamide (4 mg, 0.01 mmol, 10%). $^{1}$H NMR (400 MHz, DMSO-d6) δ 12.95 (s, 1H), 8.55 (s, 1H), 8.51-8.43 (m, 2H), 8.18 (s, 1H), 7.93 (s, 1H), 7.61 (d, J=8.1 Hz, 2H), 7.36-7.27 (m, 3H), 7.20 (dd, J=6.9, 4.5 Hz, 3H), 4.90 (s, 2H), 3.79 (s, 2H). LCMS $t_R$=1.81 min, m/z=404.1291 [M+H]$^+$.

N-[(3-chlorophenyl)methyl]-N-[4-(1H-pyrazol-4-yl)phenyl]-2-pyridazin-3-yl-acetamide (Compound 6)

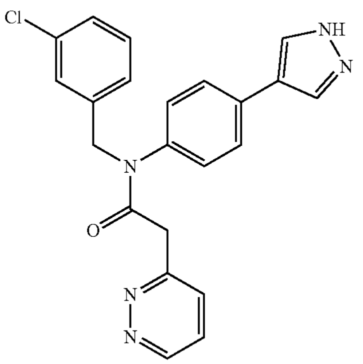 [SMILES: O=C(Cc1cccnn1)N(Cc1cccc(Cl)c1)c1ccc(-c2cn[nH]c2)cc1]

Prepared by general procedure A to afford N-[(3-chlorophenyl)methyl]-N-[4-(1H-pyrazol-4-yl)phenyl]-2-pyridazin-3-yl-acetamide (3 mg, 0.01 mmol, 7%). $^1$H NMR (400 MHz, DMSO-d6) δ 9.12-9.07 (m, 1H), 8.08 (s, 2H), 7.64 (d, J=8.0 Hz, 2H), 7.61 (d, J=7.2 Hz, 2H), 7.33 (d, J=8.4 Hz, 2H), 7.24 (dd, J=16.2, 7.4 Hz, 3H), 7.10 (s, 2H), 4.92 (s, 2H), 3.90 (s, 2H). LCMS $t_R$=1.73 min, m/z=404.1276 $[M+H]^+$.

N-[(3-chlorophenyl)methyl]-2-(5-phenyl-1,3,4-oxadiazol-2-yl)-N-[4-(1H-pyrazol-4-yl)phenyl]acetamide (Compound 7)

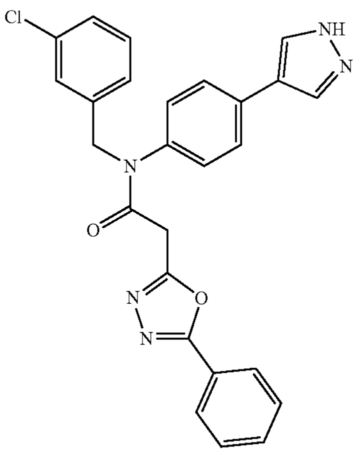

Prepared by general procedure A to afford N-[(3-chlorophenyl)methyl]-2-(5-phenyl-1,3,4-oxadiazol-2-yl)-N-[4-(1H-pyrazol-4-yl)phenyl]acetamide (7 mg, 0.01 mmol, 15%). $^1$H NMR (400 MHz, DMSO-d6) δ 12.95 (s, 1H), 8.17 (s, 1H), 7.99 (s, 1H), 7.94 (d, J=7.3 Hz, 2H), 7.61 (dt, J=19.2, 7.8 Hz, 5H), 7.38-7.28 (m, 5H), 7.22 (d, J=7.0 Hz, 1H), 4.93 (s, 2H), 4.04 (s, 2H). LCMS $t_R$=2.08 min, m/z=470.1385 $[M+H]^+$.

N-[(3-chlorophenyl)methyl]-2-(5-phenyl-1,3,4-thiadiazol-2-yl)-N-[4-(1H-pyrazol-4-yl)phenyl]acetamide (Compound 8)

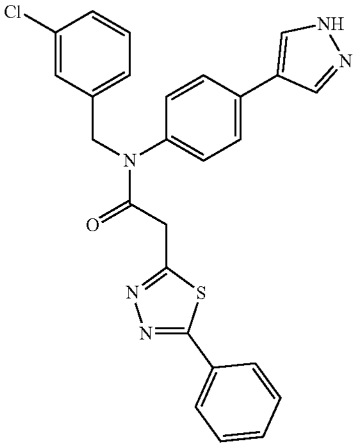 [SMILES: O=C(Cc1nnc(-c2ccccc2)s1)N(Cc1cccc(Cl)c1)c1ccc(-c2cn[nH]c2)cc1]

N-[(3-chlorophenyl)methyl]-2-(5-phenyl-1,3,4-thiadiazol-2-yl)-N-[4-(1H-pyrazol-4-yl)phenyl]acetamide: Prepared by general procedure A to afford N-[(3-chlorophenyl)methyl]-2-(5-phenyl-1,3,4-thiadiazol-2-yl)-N-[4-(1H-pyrazol-4-yl)phenyl]acetamide (5 mg, 0.01 mmol, 10%). $^1$H NMR (400 MHz, DMSO-d6) δ 12.98 (s, 1H), 8.23 (s, 1H), 7.97 (dd, J=6.8, 2.9 Hz, 3H), 7.68 (d, J=8.1 Hz, 2H), 7.59-7.53 (m, 3H), 7.37-7.27 (m, 5H), 7.22 (d, J=6.9 Hz, 1H), 4.95 (s, 2H), 4.16 (s, 2H). LCMS $t_R$=2.22 min, m/z=486.1174 $[M+H]^+$.

N-[(3-chloro-5-fluoro-phenyl)methyl]-N-[4-(1H-imidazol-4-yl)phenyl]-2-([1,2,4]triazolo[4,3-a]pyridin-3-yl)acetamide (Compound 9)

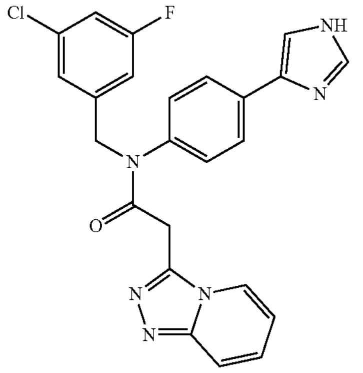 [SMILES: O=C(Cc1nnc2ccccn12)N(Cc1cc(F)cc(Cl)c1)c1ccc(-c2c[nH]cn2)cc1]

Prepared by general procedure B to afford N-[(3-chloro-5-fluoro-phenyl)methyl]-N-[4-(1H-imidazol-4-yl)phenyl]-2-([1,2,4]triazolo[4,3-a]pyridin-3-yl)acetamide (19 mg, 0.04 mmol, 41%). $^1$H NMR (400 MHz, Methanol-d4) δ 8.32 (d, J=7.0 Hz, 1H), 7.78 (d, J=9.4 Hz, 3H), 7.69 (d, J=9.3 Hz, 1H), 7.52 (s, 1H), 7.43 (dd, J=9.4, 6.5 Hz, 1H), 7.28 (d, J=8.4 Hz, 2H), 7.13 (s, 2H), 7.01 (d, J=8.1 Hz, 2H), 4.95 (s, 2H), 4.24 (s, 2H). Exchangeable imidazole proton not observed. LCMS $t_R$=1.55 min, m/z=461.1269 $[M+H]^+$.

N-[(3-chloro-5-fluoro-phenyl)methyl]-2-(6-fluoro-[1,2,4]triazolo[4,3-a]pyridin-3-yl)-N-[4-(1H-imidazol-4-yl)phenyl]acetamide (Compound 10)

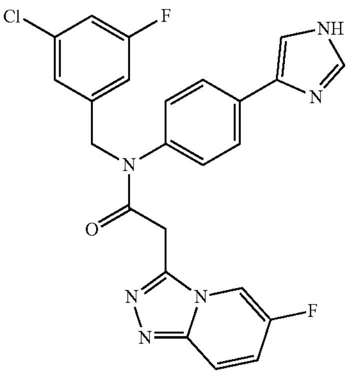 [SMILES: O=C(Cc1nnc2ccc(F)cn12)N(Cc1cc(F)cc(Cl)c1)c1ccc(-c2c[nH]cn2)cc1]

Prepared by general procedure B to afford N-[(3-chloro-5-fluoro-phenyl)methyl]-2-(6-fluoro-[1,2,4]triazolo[4,3-a]pyridin-3-yl)-N-[4-(1H-imidazol-4-yl)phenyl]acetamide (19 mg, 0.04 mmol, 40%). $^1$H NMR (400 MHz, Methanol-d4) δ 8.49 (s, 1H), 7.85 (s, 1H), 7.76 (dd, J=18.5, 6.6 Hz, 3H), 7.54 (s, 1H), 7.44 (t, J=9.4 Hz, 1H), 7.31-7.25 (m, 2H), 7.11 (d, J=11.6 Hz, 2H), 7.01 (d, J=9.2 Hz, 1H), 4.95 (s, 2H), 4.21 (s, 2H). Exchangeable imidazole proton not observed. LCMS $t_R$=1.65 min, m/z=479.1193 $[M+H]^+$.

N-[(3-chloro-5-fluoro-phenyl)methyl]-2-imidazo[1,2-a]pyridin-3-yl-N-[4-(1H-imidazol-4-yl)phenyl]acetamide (Compound 11)

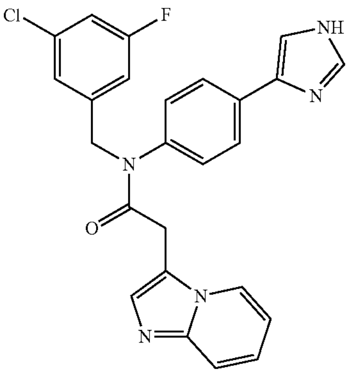 [SMILES: O=C(Cc1cnc2ccccn12)N(Cc1cc(F)cc(Cl)c1)c1ccc(-c2c[nH]cn2)cc1]

Prepared by general procedure B to afford N-[(3-chloro-5-fluoro-phenyl)methyl]-2-imidazo[1,2-a]pyridin-3-yl-N-[4-(1H-imidazol-4-yl)phenyl]acetamide (27 mg, 0.06 mmol, 59%). $^1$H NMR (400 MHz, Methanol-d4) δ 8.47 (d, J=6.9 Hz, 1H), 7.92 (s, 1H), 7.82 (d, J=8.0 Hz, 2H), 7.74 (d, J=9.1 Hz, 1H), 7.67 (t, J=7.9 Hz, 1H), 7.59 (s, 1H), 7.54 (s, 1H), 7.27 (dd, J=19.2, 7.3 Hz, 3H), 7.12 (d, J=5.5 Hz, 2H), 6.98 (d, J=9.2 Hz, 1H), 4.94 (s, 2H), 4.07 (s, 2H). Exchangeable imidazole proton not observed. LCMS $t_R$=1.53 min, m/z=460.1338 $[M+H]^+$.

N-[(3-chloro-5-fluoro-phenyl)methyl]-N-[4-(1H-imidazol-4-yl)phenyl]-2-(4-isoquinolyl)acetamide (Compound 12)

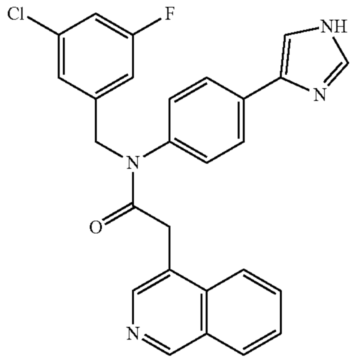 [SMILES: O=C(Cc1cncc2ccccc12)N(Cc1cc(F)cc(Cl)c1)c1ccc(-c2c[nH]cn2)cc1]

Prepared by general procedure B to afford N-[(3-chloro-5-fluoro-phenyl)methyl]-N-[4-(1H-imidazol-4-yl)phenyl]-2-(4-isoquinolyl)acetamide (22 mg, 0.05 mmol, 47%). $^1$H NMR (400 MHz, Methanol-d4) δ 9.15 (s, 1H), 8.32 (s, 1H), 8.14 (d, J=8.2 Hz, 1H), 8.04 (s, 1H), 7.95 (d, J=8.6 Hz, 1H), 7.86 (t, J=7.7 Hz, 1H), 7.81-7.68 (m, 4H), 7.27 (d, J=8.1 Hz, 2H), 7.10 (d, J=9.6 Hz, 2H), 6.99-6.92 (m, 1H), 4.94 (s, 2H), 4.08 (s, 2H). Exchangeable imidazole proton not observed. LCMS $t_R$=1.57 min, m/z=471.1385 $[M+H]^+$.

N-(4-(azetidin-3-yl)phenyl)-N-(3-chloro-5-fluorobenzyl)-2-(phthalazin-1-yl)acetamide (Compound 82)

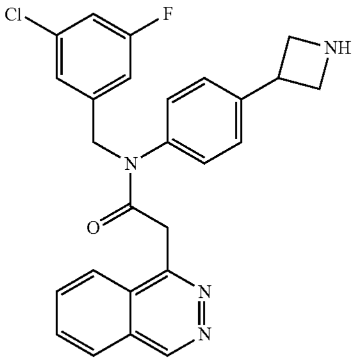 [SMILES: O=C(Cc1nncc2ccccc12)N(Cc1cc(F)cc(Cl)c1)c1ccc(C2CNC2)cc1]

Step 1. tert-butyl 3-[4-[(3-chloro-5-fluoro-phenyl)methylamino]phenyl]azetidine-1-carboxylate. A mixture of 3-Chloro-5-fluorobenzaldehyde (140.5 mg, 0.886 mmol) and tert-butyl 3-(4-aminophenyl)azetidine-1-carboxylate (200.0 mg, 0.805 mmol) in DCM (2 mL) and AcOH (0.1 mL) was stirred for 30 min at rt before the addition of $NaBH(OAc)_3$ (265.1 mg, 1.208 mmol). The mixture was stirred for an additional 2 h at rt. Saturated aqueous $NH_4Cl$ (5 mL) was added, and the crude residue extracted with DCM, concentrated, and purified by ISCO automated flash chromatography to afford a yellow solid (250 mg, 0.640 mmol, 79%): LCMS (Nonpolar Method) $t_R$=2.22 min, m/z 391.1572 $[M+H]^+$; $^1$H NMR (400 MHz, MeOD) δ 7.21 (s, 1H), 7.10-6.98 (m, 4H), 6.58 (d, J=8.4 Hz, 2H), 4.33 (s, 2H), 4.25 (t, J=8.6 Hz, 2H), 3.84 (t, J=7.4 Hz, 2H), 3.71-3.61 (m, 1H), 1.45 (s, 9H).

Step 2. tert-Butyl 3-[4-[(3-tert-butoxy-3-oxo-propanoyl)-[(3-chloro-5-fluoro-phenyl)methyl]amino]phenyl]azetidine-1-carboxylate. To a stirred solution of aniline from step 1 above (300.0 mg, 0.768 mmol) and 3-tert-butoxy-3-oxopropanoic acid (147.5 mg, 0.921 mmol) in THE (2.5 mL) was added T3P (50% in EtOAc, 1.4 mL, 2.303 mmol), followed by pyridine (185.5 μL, 2.303 mmol). The reaction was stirred at 60° C. for 2 h, diluted with water (5 mL), and extracted with EtOAc. The combined organic layers were washed with brine, concentrated, and purified by flash chromatography to afford a yellow oil (341.0 mg, 0.640 mmol, 83%): LCMS (Nonpolar Method) $t_R$=2.40 min, m/z 421.0957 $[M+H]^+$; $^1H$ NMR (400 MHz, MeOD) δ 7.40 (d, J=7.9 Hz, 2H), 7.22-7.06 (m, 4H), 7.01 (d, J=9.3 Hz, 1H), 4.92 (s, 2H), 4.34 (t, J=8.5 Hz, 2H), 3.92 (t, J=7.1 Hz, 2H), 3.85 (q, J=7.6 Hz, 1H), 3.20 (s, 2H), 1.46 (s, 9H), 1.41 (s, 9H).

Step 3. tert-Butyl 3-[4-[(3-tert-butoxy-3-oxo-2-phthalazin-1-yl-propanoyl)-[(3-chloro-5-fluoro-phenyl)methyl]amino]phenyl]azetidine-1-carboxylate. To a vial containing NaH (30.6 mg, 1.276 mmol) was added tert-Butyl 3-[4-[(3-tert-butoxy-3-oxo-propanoyl)-[(3-chloro-5-fluoro-phenyl)methyl]amino]phenyl]azetidine-1-carboxylate (340.0 mg, 0.638 mmol) in dioxane (1.5 mL) at 0° C. The reaction was stirred at rt for 1 h before the addition of 1-chlorophthalazine (105.0 mg, 0.638 mmol) in dioxane (1 mL). The reaction was stirred at 80° C. for an additional 16 h, diluted with water (5 mL), and extracted with EtOAc. The combined organic layers were washed with brine, concentrated, and purified by flash chromatography to afford an orange solid (112 mg, 0.169 mmol, 27%): LCMS (General Method) $t_R$=2.04 min, m/z 661.2611 $[M+H]^+$;

Step 4. N-[4-(azetidin-3-yl)phenyl]-N-[(3-chloro-5-fluoro-phenyl)methyl]-2-phthalazin-1-yl-acetamide. To a solution of tert-Butyl 3-[4-[(3-tert-butoxy-3-oxo-2-phthalazin-1-yl-propanoyl)-[(3-chloro-5-fluoro-phenyl)methyl]amino]phenyl]azetidine-1-carboxylate (112 mg, 0.169 mmol) in DCM (1 mL) was added TFA (2.9 mL, 38.272 mmol), and the mixture was stirred for 5 h at rt. The reaction mixture was concentrated and purified by preparative RP-HPLC to afford a yellow solid (35 mg, 0.076 mmol, 12%): $^1H$ NMR (400 MHz, MeOD) δ 9.75 (s, 1H), 8.32 (dd, J=20.2, 7.5 Hz, 2H), 8.20 (qd, J=7.6, 3.6 Hz, 2H), 7.46 (d, J=8.0 Hz, 2H), 7.37 (d, J=8.0 Hz, 2H), 7.11 (d, J=8.6 Hz, 2H), 6.99 (d, J=9.2 Hz, 1H), 4.96 (s, 2H), 4.41-4.17 (m, 5H); Purity≥95% by LCMS (Nonpolar Method) $t_R$=1.62 min, m/z 461.1530 $[M+H]^+$; HRMS calcd for $C_{26}H_{22}ClFN_4O$ $[M+H]^+$ 461.1544.

Additional Compounds

The additional compounds shown in Table 1 were prepared using the general procedures disclosed above, using appropriate starting materials.

TABLE 1

Additional Compounds

| Compound No. | Structure | LCMS-HRMS TOF |
|---|---|---|
| 13 | 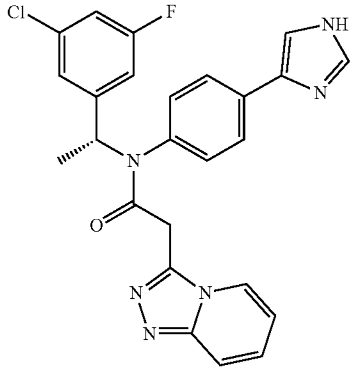 [SMILES: C[C@H](c1cc(F)cc(Cl)c1)N(C(=O)Cc1nnc2ccccn12)c1ccc(-c2c[nH]cn2)cc1] | >95% LC-MS (210, 254 nm); $t_R$ = 1.60 min, m/z = 475.1462 $[M + H]^+$ |
| 14 | 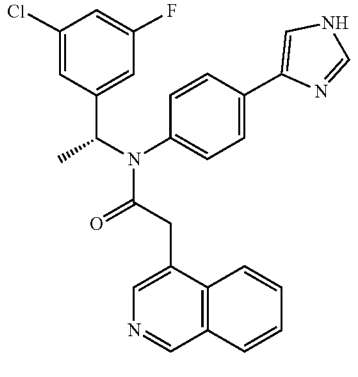 [SMILES: C[C@H](c1cc(F)cc(Cl)c1)N(C(=O)Cc1cncc2ccccc12)c1ccc(-c2c[nH]cn2)cc1] | >95% LC-MS (210, 254 nm); $t_R$ = 1.61 min, m/z = 485.1552 $[M + H]^+$ |

TABLE 1-continued
| Additional Compounds | | |
|---|---|---|
| Compound No. | Structure | LCMS-HRMS TOF |
| 15 | 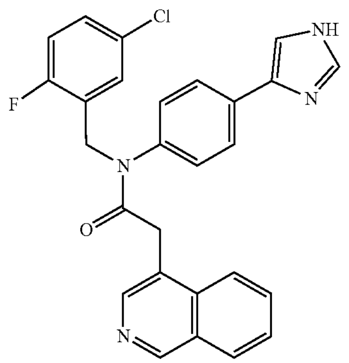 | >95% LC-MS (210, 254 nm); $t_R$ = 1.54 min, m/z = 471.1348 $[M + H]^+$ |
| 16 | 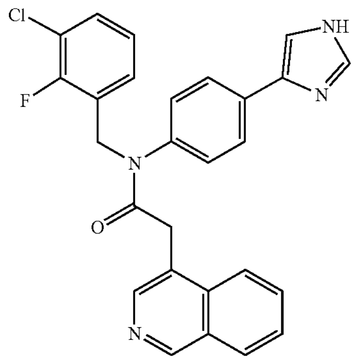 [SMILES: O=C(Cc1cncc2ccccc12)N(Cc1cccc(Cl)c1F)c1ccc(-c2c[nH]cn2)cc1] | >95% LC-MS (210, 254 nm); $t_R$ = 1.54 min, m/z = 471.1354 $[M + H]^+$ |
| 17 | 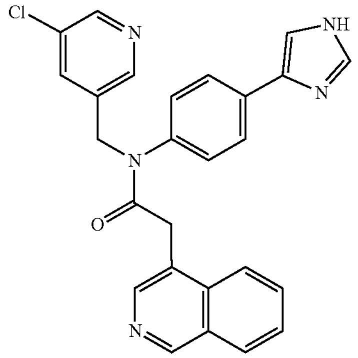 [SMILES: O=C(Cc1cncc2ccccc12)N(Cc1cncc(Cl)c1)c1ccc(-c2c[nH]cn2)cc1] | >95% LC-MS (210, 254 nm); $t_R$ = 1.35 min, m/z = 454.1404 $[M + H]^+$ |
| 18 | 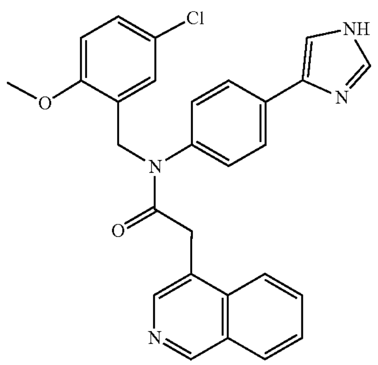 | >95% LC-MS (210, 254 nm); $t_R$ = 1.57 min, m/z = 483.1556 $[M + H]^+$ |

TABLE 1-continued
| Additional Compounds | | |
|---|---|---|
| Compound No. | Structure | LCMS-HRMS TOF |
| 19 | 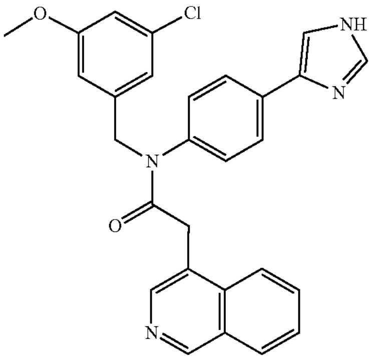 [SMILES: COc1cc(Cl)cc(CN(C(=O)Cc2cncc3ccccc23)c2ccc(-c3c[nH]cn3)cc2)c1] | >95% LC-MS (210, 254 nm); $t_R$ = 1.57 min, m/z = 483.1555 $[M + H]^+$ |
| 20 | 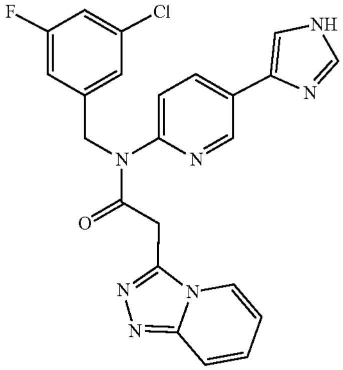 [SMILES: O=C(Cc1nnc2ccccn12)N(Cc1cc(F)cc(Cl)c1)c1ccc(-c2c[nH]cn2)cn1] | >95% LC-MS (210, 254 nm); $t_R$ = 1.53 min, m/z = 462.11 $[M + H]^+$ |
| 21 | 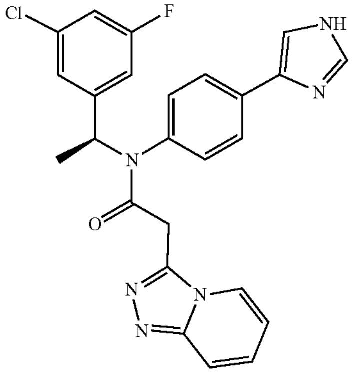 [SMILES: C[C@@H](c1cc(F)cc(Cl)c1)N(C(=O)Cc1nnc2ccccn12)c1ccc(-c2c[nH]cn2)cc1] | >95% LC-MS (210, 254 nm); $t_R$ = 1.62 min, m/z = 475.15 $[M + H]^+$ |
| 22 | 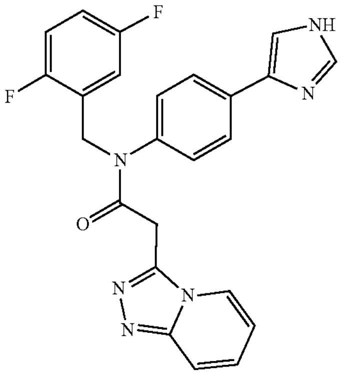 [SMILES: O=C(Cc1nnc2ccccn12)N(Cc1cc(F)ccc1F)c1ccc(-c2c[nH]cn2)cc1] | >95% LC-MS (210, 254 nm); $t_R$ = 1.375 min, m/z = 445.1596 $[M + H]^+$ |

TABLE 1-continued
| Additional Compounds | | |
|---|---|---|
| Compound No. | Structure | LCMS-HRMS TOF |
| 23 | 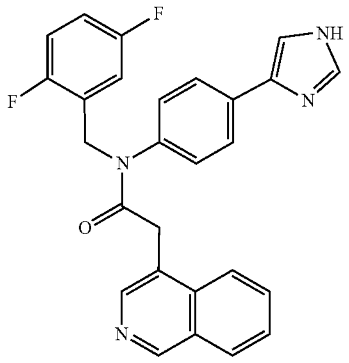 [SMILES: O=C(Cc1cncc2ccccc12)N(Cc1cc(F)ccc1F)c1ccc(-c2c[nH]cn2)cc1] | >95% LC-MS (210, 254 nm); $t_R$ = 1.383 min, m/z = 455.1691 $[M + H]^+$ |
| 24 | 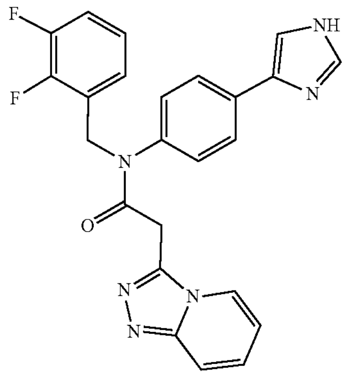 [SMILES: O=C(Cc1nnc2ccccn12)N(Cc1cccc(F)c1F)c1ccc(-c2c[nH]cn2)cc1] | >95% LC-MS (210, 254 nm); $t_R$ = 1.46 min, m/z = 445.0683 $[M + H]^+$ |
| 25 | 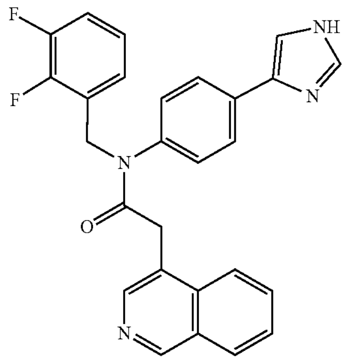 [SMILES: O=C(Cc1cncc2ccccc12)N(Cc1cccc(F)c1F)c1ccc(-c2c[nH]cn2)cc1] | >95% LC-MS (210, 254 nm); $t_R$ = 1.62 min, m/z = 455.0768 $[M + H]^+$ |
| 26 | 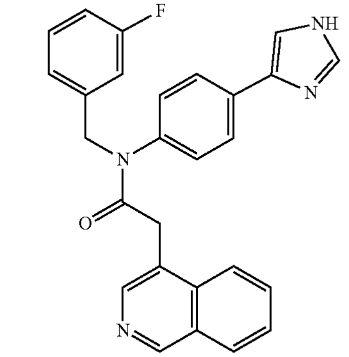 [SMILES: O=C(Cc1cncc2ccccc12)N(Cc1cccc(F)c1)c1ccc(-c2c[nH]cn2)cc1] | >95% LC-MS (210, 254 nm); $t_R$ = 1.479 min, m/z = 437.1764 $[M + H]^+$ |

TABLE 1-continued
| Additional Compounds | | |
|---|---|---|
| Compound No. | Structure | LCMS-HRMS TOF |
| 27 | 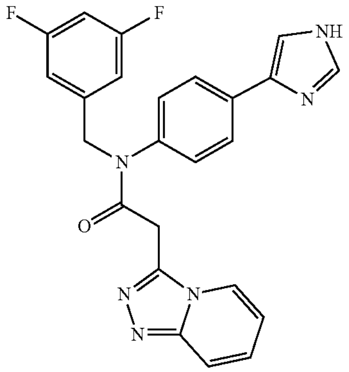 [SMILES: O=C(Cc1nnc2ccccn12)N(Cc1cc(F)cc(F)c1)c1ccc(-c2c[nH]cn2)cc1] | >95% LC-MS (210, 254 nm); $t_R$ = 1.561 min, m/z = 445.1590 $[M + H]^+$ |
| 28 | 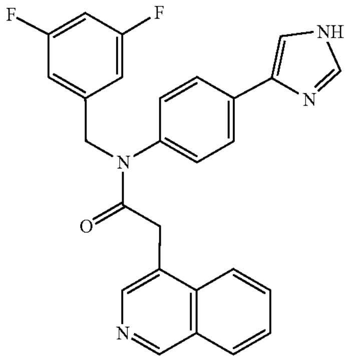 [SMILES: O=C(Cc1cncc2ccccc12)N(Cc1cc(F)cc(F)c1)c1ccc(-c2c[nH]cn2)cc1] | >95% LC-MS (210, 254 nm); $t_R$ = 1.57 min, m/z = 455.169 $[M + H]^+$ |
| 29 | 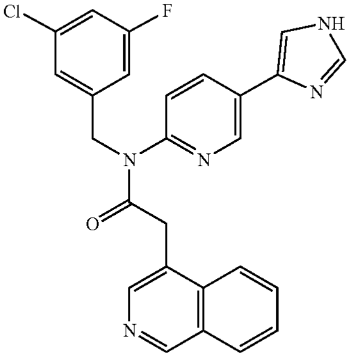 [SMILES: O=C(Cc1cncc2ccccc12)N(Cc1cc(F)cc(Cl)c1)c1ccc(-c2c[nH]cn2)cn1] | >95% LC-MS (210, 254 nm); $t_R$ = 1.54 min, m/z = 472.13 $[M + H]^+$ |
| 30 | 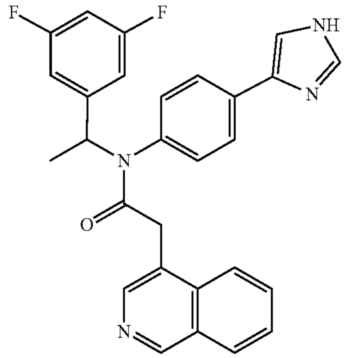 [SMILES: CC(c1cc(F)cc(F)c1)N(C(=O)Cc1cncc2ccccc12)c1ccc(-c2c[nH]cn2)cc1] | >95% LC-MS (210, 254 nm); $t_R$ = 1.54 min, m/z = 469.28 $[M + H]^+$ |

TABLE 1-continued
| Compound No. | Structure | LCMS-HRMS TOF |
|---|---|---|
| 31 | 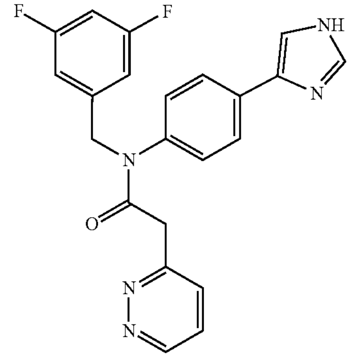 [SMILES: O=C(Cc1cccnn1)N(Cc1cc(F)cc(F)c1)c1ccc(-c2c[nH]cn2)cc1] | >95% LC-MS (210, 254 nm); $t_R$ = 1.50 min, m/z = 406.1489 $[M + H]^+$ |
| 32 | 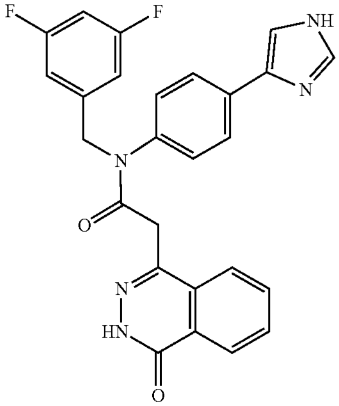 [SMILES: O=C(Cc1n[nH]c(=O)c2ccccc12)N(Cc1cc(F)cc(F)c1)c1ccc(-c2c[nH]cn2)cc1] | >95% LC-MS (210, 254 nm); $t_R$ = 1.61 min, m/z = 472.1563 $[M + H]^+$ |
| 33 | 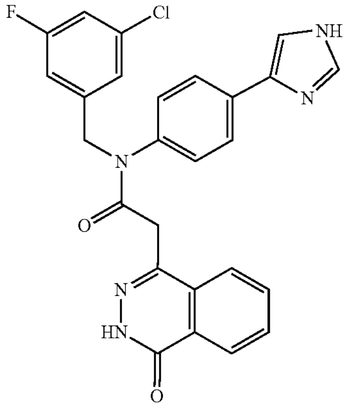 [SMILES: O=C(Cc1n[nH]c(=O)c2ccccc12)N(Cc1cc(F)cc(Cl)c1)c1ccc(-c2c[nH]cn2)cc1] | >95% LC-MS (210, 254 nm); $t_R$ = 1.68 min, m/z = 488.1265 $[M + H]^+$ |
| 34 | 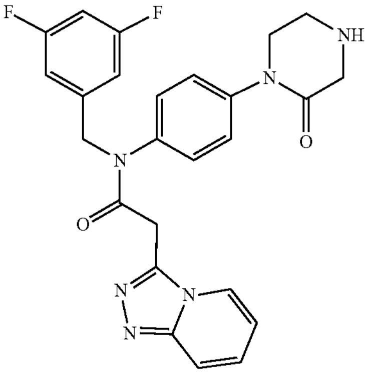 | >95% LC-MS (210, 254 nm); $t_R$ = 1.42 min, m/z = 477.15 $[M + H]^+$ |

TABLE 1-continued
| Additional Compounds | | |
|---|---|---|
| Compound No. | Structure | LCMS-HRMS TOF |
| 35 | 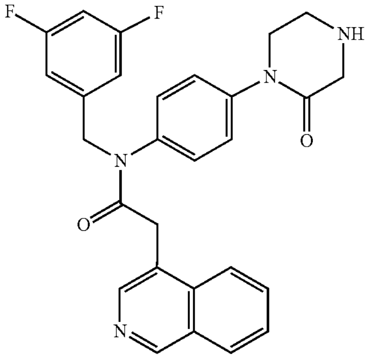 [SMILES: O=C1CNCCN1c1ccc(N(Cc2cc(F)cc(F)c2)C(=O)Cc2cncc3ccccc23)cc1] | >95% LC-MS (210, 254 nm); $t_R$ = 1.45 min, m/z = 487.15 $[M + H]^+$ |
| 36 | 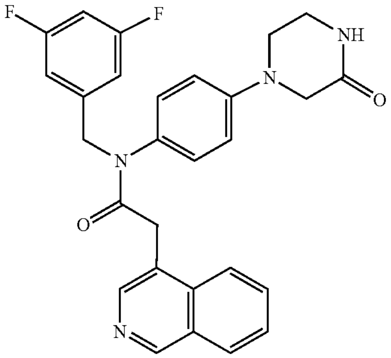 [SMILES: O=C1CN(c2ccc(N(Cc3cc(F)cc(F)c3)C(=O)Cc3cncc4ccccc34)cc2)CCN1] | >95% LC-MS (210, 254 nm); $t_R$ = 1.67 min, m/z = 487.19 $[M + H]^+$ |
| 37 | 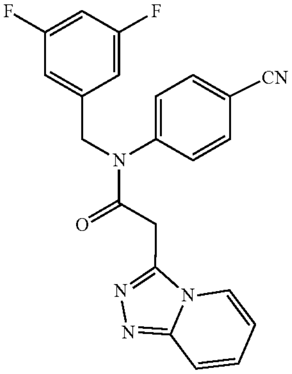 | >95% LC-MS (210, 254 nm); $t_R$ = 1.78 min, m/z = 404.10 $[M + H]^+$ |
| 38 | 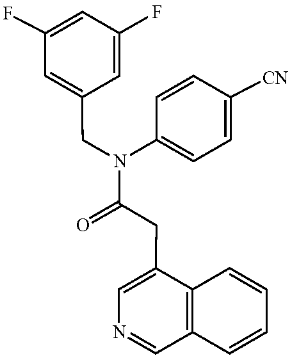 [SMILES: N#Cc1ccc(N(Cc2cc(F)cc(F)c2)C(=O)Cc2cncc3ccccc23)cc1] | >95% LC-MS (210, 254 nm); $t_R$ = 1.82 min, m/z = 414.11 $[M + H]^+$ |

TABLE 1-continued
| Additional Compounds | | |
|---|---|---|
| Compound No. | Structure | LCMS-HRMS TOF |
| 39 | 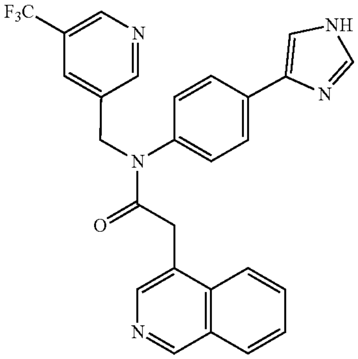 [SMILES: O=C(Cc1cncc2ccccc12)N(Cc1cncc(C(F)(F)F)c1)c1ccc(-c2c[nH]cn2)cc1] | >95% LC-MS (210, 254 nm); $t_R$ = 1.50 min, m/z = 488.0273 $[M + H]^+$ |
| 40 | 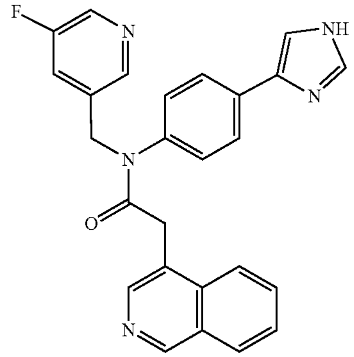 [SMILES: O=C(Cc1cncc2ccccc12)N(Cc1cncc(F)c1)c1ccc(-c2c[nH]cn2)cc1] | >95% LC-MS (210, 254 nm); $t_R$ = 1.32 min, m/z = 438.0340 $[M + H]^+$ |
| 41 | 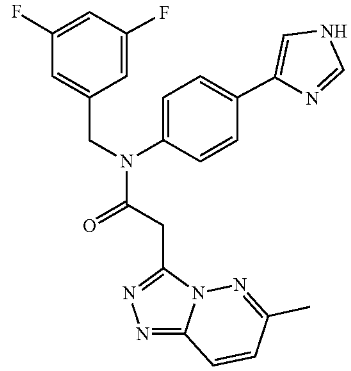 [SMILES: Cc1ccc2nnc(CC(=O)N(Cc3cc(F)cc(F)c3)c3ccc(-c4c[nH]cn4)cc3)n2n1] | >95% LC-MS (210, 254 nm); $t_R$ = 1.55 min, m/z = 460.0257 $[M + H]^+$ |
| 42 | 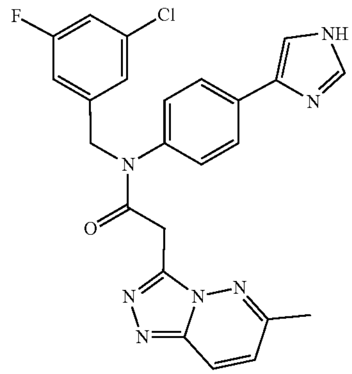 [SMILES: Cc1ccc2nnc(CC(=O)N(Cc3cc(F)cc(Cl)c3)c3ccc(-c4c[nH]cn4)cc3)n2n1] | >95% LC-MS (210, 254 nm); $t_R$ = 1.65 min, m/z = 475.9903 $[M + H]^+$ |

TABLE 1-continued
| Additional Compounds | | |
|---|---|---|
| Compound No. | Structure | LCMS-HRMS TOF |
| 43 | 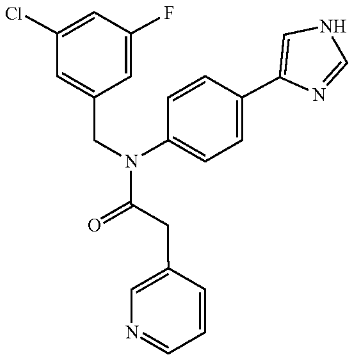 [SMILES: O=C(Cc1cccnc1)N(Cc1cc(F)cc(Cl)c1)c1ccc(-c2c[nH]cn2)cc1] | >95% LC-MS (210, 254 nm); $t_R$ = 1.45 min, m/z = 421.1218 $[M + H]^+$ |
| 44 | 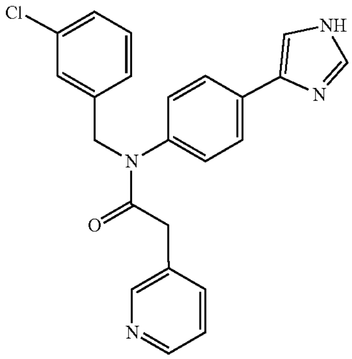 [SMILES: O=C(Cc1cccnc1)N(Cc1cccc(Cl)c1)c1ccc(-c2c[nH]cn2)cc1] | >95% LC-MS (210, 254 nm); $t_R$ = 1.42 min, m/z = 403.1298 $[M + H]^+$ |
| 45 | 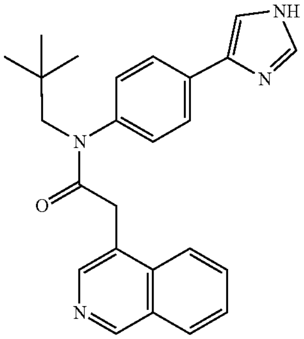 [SMILES: CC(C)(C)CN(C(=O)Cc1cncc2ccccc12)c1ccc(-c2c[nH]cn2)cc1] | >95% LC-MS (210, 254 nm); $t_R$ = 1.54 min, m/z = 399.219 $[M + H]^+$ |
| 46 | 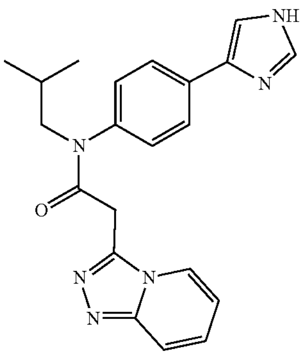 [SMILES: CC(C)CN(C(=O)Cc1nnc2ccccn12)c1ccc(-c2c[nH]cn2)cc1] | >95% LC-MS (210, 254 nm); $t_R$ = 1.52 min, m/z = 375.13 $[M + H]^+$ |

TABLE 1-continued
| Additional Compounds | | |
|---|---|---|
| Compound No. | Structure | LCMS-HRMS TOF |
| 47 | 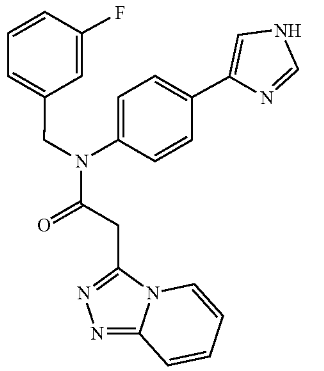 [SMILES: O=C(Cc1nnc2ccccn12)N(Cc1cccc(F)c1)c1ccc(-c2c[nH]cn2)cc1] | >95% LC-MS (210, 254 nm); $t_R$ = 1.52 min, m/z = 427.155 $[M + H]^+$ |
| 48 | 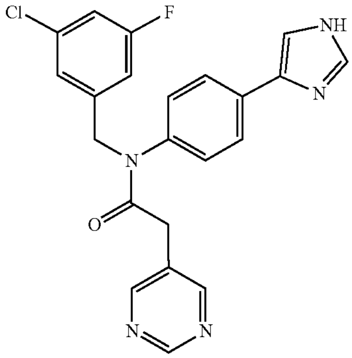 [SMILES: O=C(Cc1cncnc1)N(Cc1cc(F)cc(Cl)c1)c1ccc(-c2c[nH]cn2)cc1] | >95% LC-MS (210, 254 nm); $t_R$ = 1.58 min, m/z = 422.1178 $[M + H]^+$ |
| 49 | 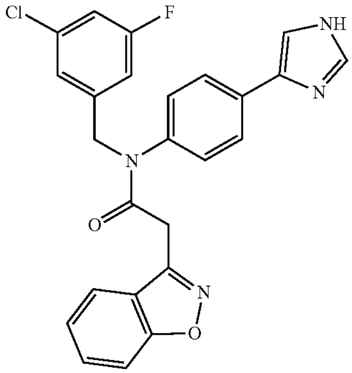 [SMILES: O=C(Cc1noc2ccccc12)N(Cc1cc(F)cc(Cl)c1)c1ccc(-c2c[nH]cn2)cc1] | >95% LC-MS (210, 254 nm); $t_R$ = 1.84 min, m/z = 461.12 $[M + H]^+$ |
| 50 | 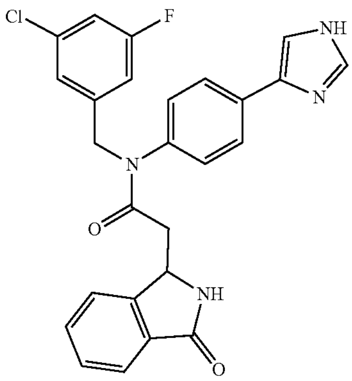 [SMILES: O=C1NC(CC(=O)N(Cc2cc(F)cc(Cl)c2)c2ccc(-c3c[nH]cn3)cc2)c2ccccc21] | >95% LC-MS (210, 254 nm); $t_R$ = 1.69 min, m/z = 475.13 $[M + H]^+$ |

TABLE 1-continued
| Additional Compounds | | |
|---|---|---|
| Compound No. | Structure | LCMS-HRMS TOF |
| 51 | 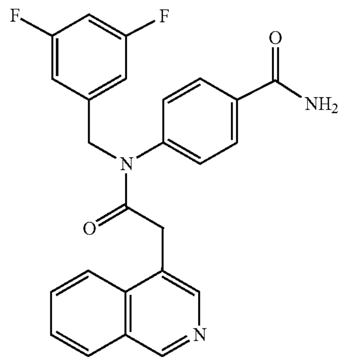 [SMILES: NC(=O)c1ccc(N(Cc2cc(F)cc(F)c2)C(=O)Cc2cncc3ccccc23)cc1] | >95% LC-MS (210, 254 nm); $t_R$ = 1.58 min, m/z = 432.1568 $[M + H]^+$ |
| 52 | 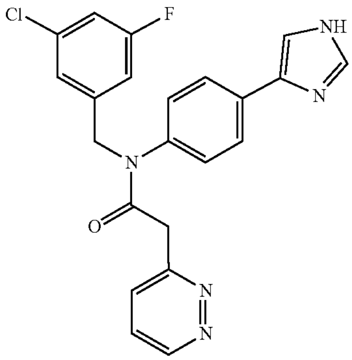 [SMILES: O=C(Cc1cccnn1)N(Cc1cc(F)cc(Cl)c1)c1ccc(-c2c[nH]cn2)cc1] | >95% LC-MS (210, 254 nm); $t_R$ = 1.54 min, m/z = 422.12 $[M + H]^+$ |
| 53 | 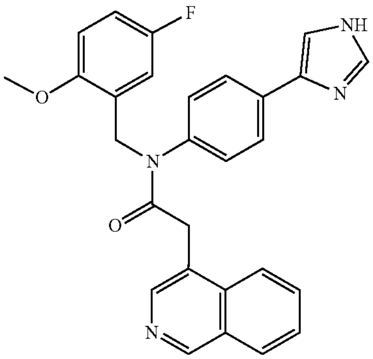 [SMILES: COc1ccc(F)cc1CN(C(=O)Cc1cncc2ccccc12)c1ccc(-c2c[nH]cn2)cc1] | >95% LC-MS (210, 254 nm); $t_R$ = 1.47 min, m/z = 467.1869 $[M + H]^+$ |
| 54 | 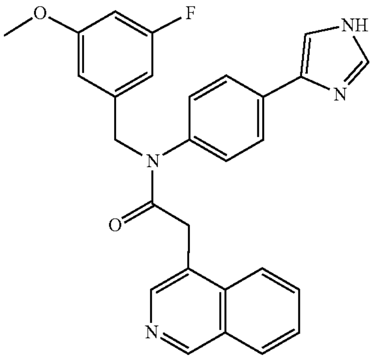 [SMILES: COc1cc(F)cc(CN(C(=O)Cc2cncc3ccccc23)c2ccc(-c3c[nH]cn3)cc2)c1] | >95% LC-MS (210, 254 nm); $t_R$ = 1.49 min, m/z = 467.1871 $[M + H]^+$ |

TABLE 1-continued
| Additional Compounds | | |
|---|---|---|
| Compound No. | Structure | LCMS-HRMS TOF |
| 55 | 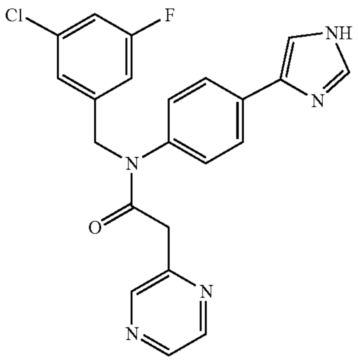 [SMILES: O=C(Cc1cnccn1)N(Cc1cc(F)cc(Cl)c1)c1ccc(-c2c[nH]cn2)cc1] | >95% LC-MS (210, 254 nm); $t_R$ = 1.63 min, m/z = 422.1206 $[M + H]^+$ |
| 56 | 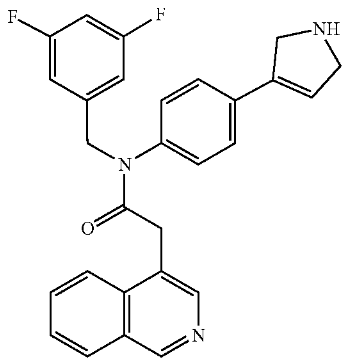 [SMILES: O=C(Cc1cncc2ccccc12)N(Cc1cc(F)cc(F)c1)c1ccc(C2=CCNC2)cc1] | >95% LC-MS (210, 254 nm); $t_R$ = 1.48 min, m/z = 456.19 $[M + H]^+$ |
| 57 | 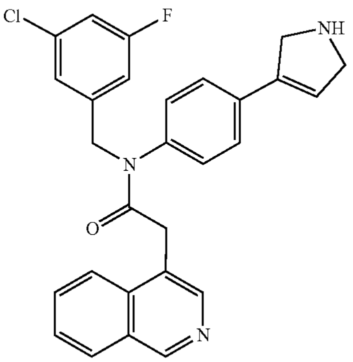 [SMILES: O=C(Cc1cncc2ccccc12)N(Cc1cc(F)cc(Cl)c1)c1ccc(C2=CCNC2)cc1] | >95% LC-MS (210, 254 nm); $t_R$ = 1.54 min, m/z = 472.16 $[M + H]^+$ |
| 58 | 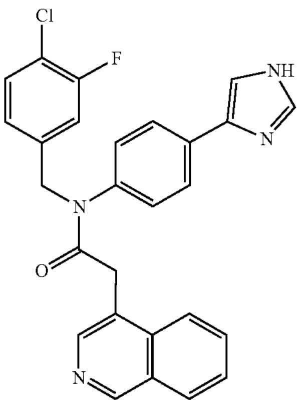 [SMILES: O=C(Cc1cncc2ccccc12)N(Cc1ccc(Cl)c(F)c1)c1ccc(-c2c[nH]cn2)cc1] | >95% LC-MS (210, 254 nm); $t_R$ = 1.55 min, m/z = 471.1351 $[M + H]^+$ |

TABLE 1-continued
| Compound No. | Structure | LCMS-HRMS TOF |
|---|---|---|
| Additional Compounds | | |
| 59 | 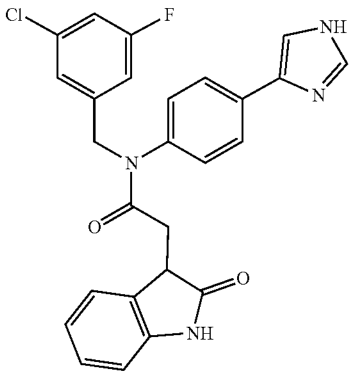 [SMILES: O=C1Nc2ccccc2C1CC(=O)N(Cc1cc(F)cc(Cl)c1)c1ccc(-c2c[nH]cn2)cc1] | >95% LC-MS (210, 254 nm); $t_R$ = 1.73 min, m/z = 475.1317 $[M + H]^+$ |
| 60 | 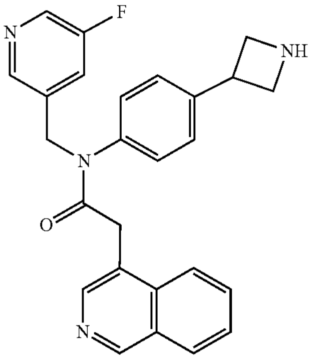 [SMILES: O=C(Cc1cncc2ccccc12)N(Cc1cncc(F)c1)c1ccc(C2CNC2)cc1] | >95% LC-MS (210, 254 nm); $t_R$ = 1.30 min, m/z = 427.1937 $[M + H]^+$ |
| 61 | 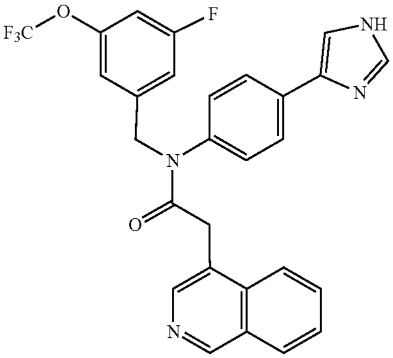 [SMILES: O=C(Cc1cncc2ccccc12)N(Cc1cc(F)cc(OC(F)(F)F)c1)c1ccc(-c2c[nH]cn2)cc1] | >95% LC-MS (210, 254 nm); $t_R$ = 1.68 min, m/z = 521.16 $[M + H]^+$ |
| 62 | 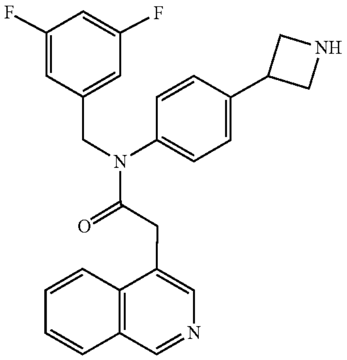 [SMILES: O=C(Cc1cncc2ccccc12)N(Cc1cc(F)cc(F)c1)c1ccc(C2CNC2)cc1] | >95% LC-MS (210, 254 nm); $t_R$ = 1.49 min, m/z = 444.19 $[M + H]^+$ |

TABLE 1-continued
| Additional Compounds | | |
|---|---|---|
| Compound No. | Structure | LCMS-HRMS TOF |
| 63 | 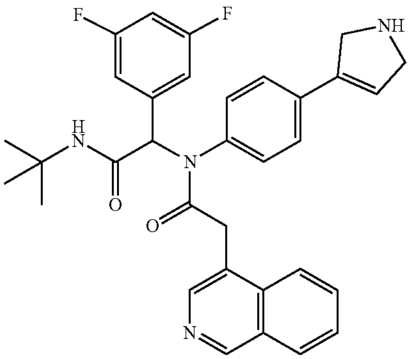 [SMILES: CC(C)(C)NC(=O)C(c1cc(F)cc(F)c1)N(C(=O)Cc1cncc2ccccc12)c1ccc(C2=CCNC2)cc1] | >95% LC-MS (210, 254 nm); $t_R$ = 1.63 min, m/z = 555.26 $[M + H]^+$ |
| 64 | 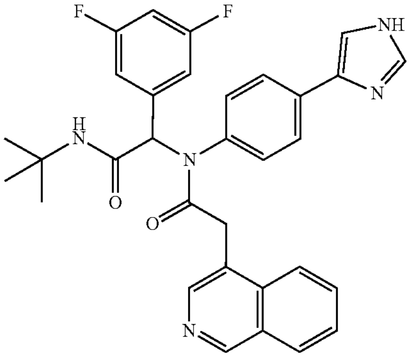 [SMILES: CC(C)(C)NC(=O)C(c1cc(F)cc(F)c1)N(C(=O)Cc1cncc2ccccc12)c1ccc(-c2c[nH]cn2)cc1] | >95% LC-MS (210, 254 nm); $t_R$ = 1.62 min, m/z = 554.2355 $[M + H]^+$ |
| 65 | 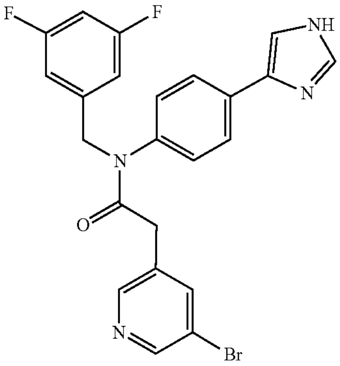 [SMILES: O=C(Cc1cncc(Br)c1)N(Cc1cc(F)cc(F)c1)c1ccc(-c2c[nH]cn2)cc1] | >95% LC-MS (210, 254 nm); $t_R$ = 1.76 min, m/z = 483.06 $[M + H]^+$ |
| 66 | 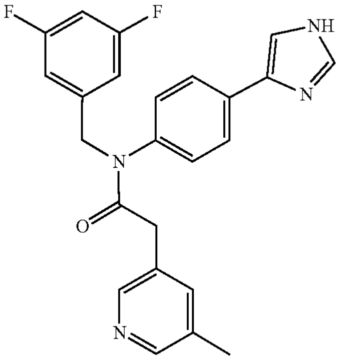 [SMILES: Cc1cncc(CC(=O)N(Cc2cc(F)cc(F)c2)c2ccc(-c3c[nH]cn3)cc2)c1] | >95% LC-MS (210, 254 nm); $t_R$ = 1.51 min, m/z = 419.17 $[M + H]^+$ |

TABLE 1-continued
| Compound No. | Structure | LCMS-HRMS TOF |
|---|---|---|
| | Additional Compounds | |
| 67 | 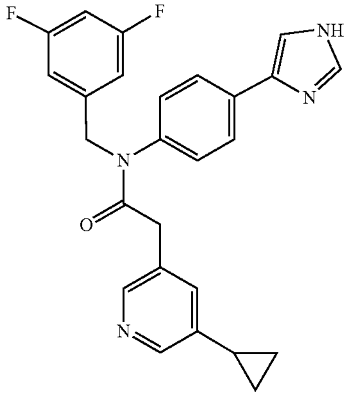 [SMILES: O=C(Cc1cncc(C2CC2)c1)N(Cc1cc(F)cc(F)c1)c1ccc(-c2c[nH]cn2)cc1] | >95% LC-MS (210, 254 nm); $t_R$ = 1.57 min, m/z = 445.18 $[M + H]^+$ |
| 68 | 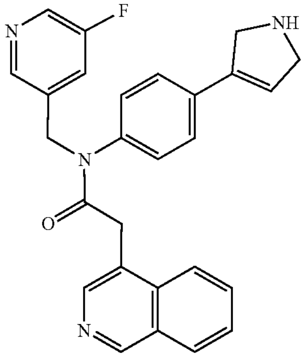 [SMILES: O=C(Cc1cncc2ccccc12)N(Cc1cncc(F)c1)c1ccc(C2=CCNC2)cc1] | >95% LC-MS (210, 254 nm); $t_R$ = 1.30 min, m/z = 439.1885 $[M + H]^+$ |
| 69 | 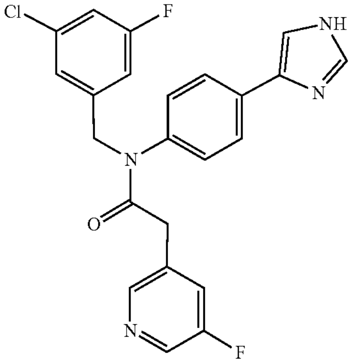 [SMILES: O=C(Cc1cncc(F)c1)N(Cc1cc(F)cc(Cl)c1)c1ccc(-c2c[nH]cn2)cc1] | >95% LC-MS (210, 254 nm); $t_R$ = 1.72 min, m/z = 439.11 $[M + H]^+$ |
| 70 | 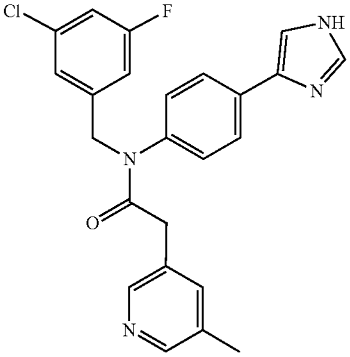 [SMILES: Cc1cncc(CC(=O)N(Cc2cc(F)cc(Cl)c2)c2ccc(-c3c[nH]cn3)cc2)c1] | >95% LC-MS (210, 254 nm); $t_R$ = 1.55 min, m/z = 435.13 $[M + H]^+$ |

TABLE 1-continued
| Additional Compounds | | |
|---|---|---|
| Compound No. | Structure | LCMS-HRMS TOF |
| 71 | 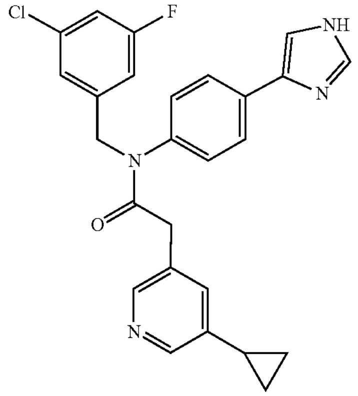 [SMILES: O=C(Cc1cncc(C2CC2)c1)N(Cc1cc(F)cc(Cl)c1)c1ccc(-c2c[nH]cn2)cc1] | >95% LC-MS (210, 254 nm); $t_R$ = 1.63 min, m/z = 461.15 $[M + H]^+$ |
| 72 | 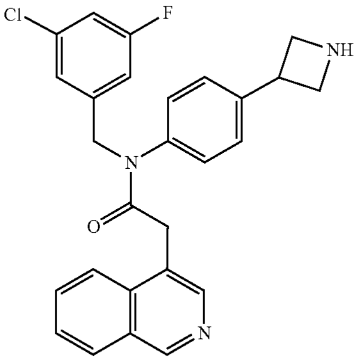 [SMILES: O=C(Cc1cncc2ccccc12)N(Cc1cc(F)cc(Cl)c1)c1ccc(C2CNC2)cc1] | >95% LC-MS (210, 254 nm); $t_R$ = 1.57 min, m/z = 459.97 $[M + H]^+$ |
| 73 | 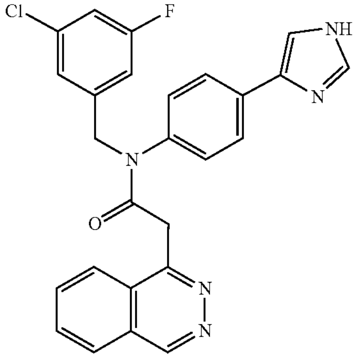 [SMILES: O=C(Cc1nncc2ccccc12)N(Cc1cc(F)cc(Cl)c1)c1ccc(-c2c[nH]cn2)cc1] | See Example 82 procedure >95% LC-MS (210, 254 nm); $t_R$ = 1.62 min, m/z = 472.13 $[M + H]^+$ |
| 74 | 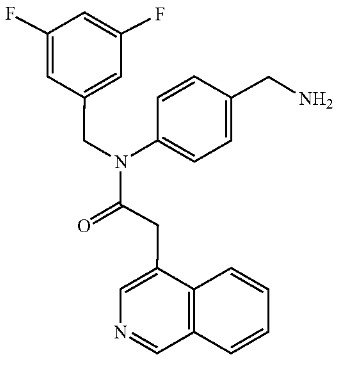 [SMILES: NCc1ccc(N(Cc2cc(F)cc(F)c2)C(=O)Cc2cncc3ccccc23)cc1] | >95% LC-MS (210, 254 nm); $t_R$ = 1.47 min, m/z = 418.1726 $[M + H]^+$ |

TABLE 1-continued
Additional Compounds
| Compound No. | Structure | LCMS-HRMS TOF |
| --- | --- | --- |
| 75 | 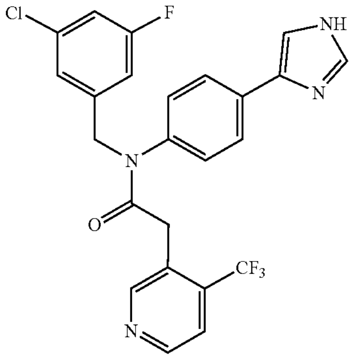 [SMILES: O=C(Cc1cnccc1C(F)(F)F)N(Cc1cc(F)cc(Cl)c1)c1ccc(-c2c[nH]cn2)cc1] | >95% LC-MS (210, 254 nm); $t_R$ = 1.82 min, m/z = 489.11 $[M + H]^+$ |
| 76 | 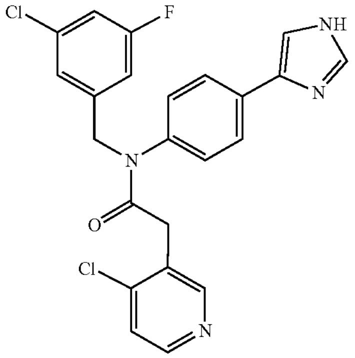 [SMILES: O=C(Cc1cnccc1Cl)N(Cc1cc(F)cc(Cl)c1)c1ccc(-c2c[nH]cn2)cc1] | >95% LC-MS (210, 254 nm); $t_R$ = 1.63 min, m/z = 455.08 $[M + H]^+$ |
| 77 | 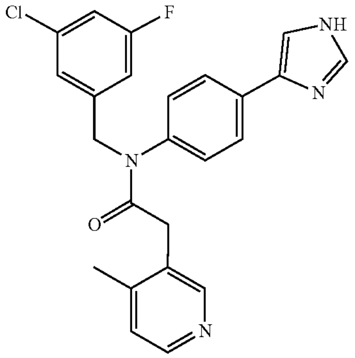 | >95% LC-MS (210, 254 nm); $t_R$ = 1.55 min, m/z = 435.14 $[M + H]^+$ |
| 78 | 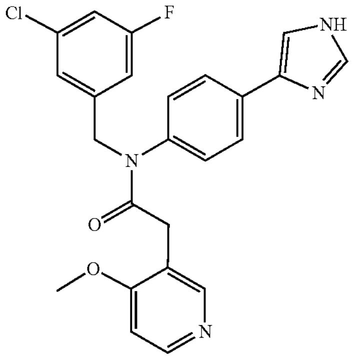 [SMILES: COc1ccncc1CC(=O)N(Cc1cc(F)cc(Cl)c1)c1ccc(-c2c[nH]cn2)cc1] | >95% LC-MS (210, 254 nm); $t_R$ = 1.52 min, m/z = 451.14 $[M + H]^+$ |

TABLE 1-continued
| Additional Compounds | | |
|---|---|---|
| Compound No. | Structure | LCMS-HRMS TOF |
| 79 | 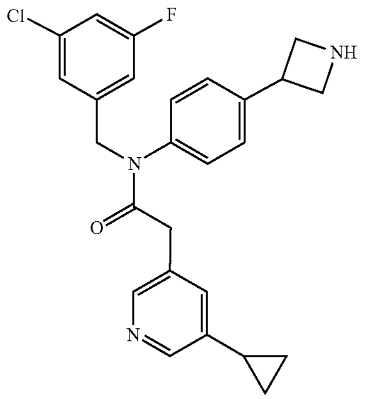 [SMILES: O=C(Cc1cncc(C2CC2)c1)N(Cc1cc(F)cc(Cl)c1)c1ccc(C2CNC2)cc1] | >95% LC-MS (210, 254 nm); $t_R$ = 1.60 min, m/z = 450.17 $[M + H]^+$ |
| 80 | 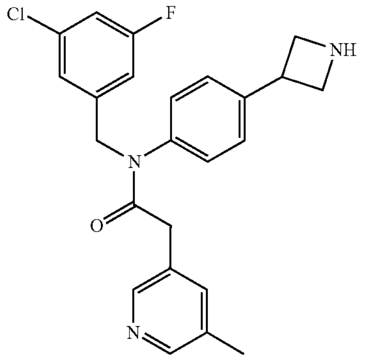 [SMILES: Cc1cncc(CC(=O)N(Cc2cc(F)cc(Cl)c2)c2ccc(C3CNC3)cc2)c1] | >95% LC-MS (210, 254 nm); $t_R$ = 1.52 min, m/z = 424.16 $[M + H]^+$ |
| 81 | 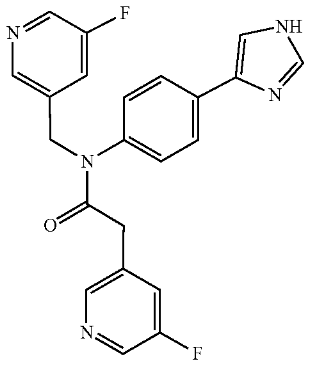 [SMILES: O=C(Cc1cncc(F)c1)N(Cc1cncc(F)c1)c1ccc(-c2c[nH]cn2)cc1] | >95% LC-MS (210, 254 nm); $t_R$ = 1.37 min, m/z = 406.14 $[M + H]^+$ |
| 82 | 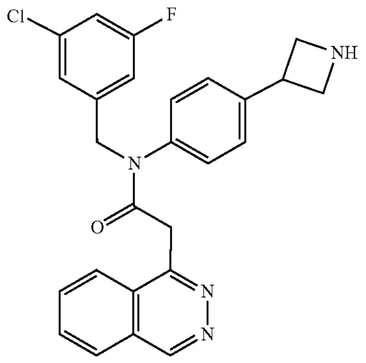 [SMILES: O=C(Cc1nncc2ccccc12)N(Cc1cc(F)cc(Cl)c1)c1ccc(C2CNC2)cc1] | >95% LC-MS (210, 254 nm); $t_R$ = 1.62 min, m/z = 461.15 $[M + H]^+$ |

TABLE 1-continued

| Additional Compounds | | |
|---|---|---|
| Compound No. | Structure | LCMS-HRMS TOF |
| 83 | 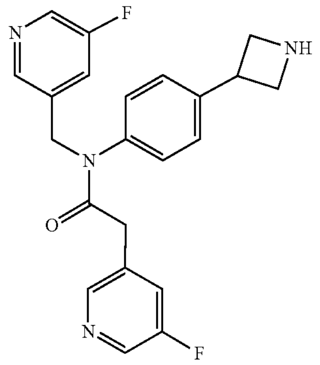 [SMILES: O=C(Cc1cncc(F)c1)N(Cc1cncc(F)c1)c1ccc(C2CNC2)cc1] | >95% LC-MS (210, 254 nm); $t_R$ = 1.38 min, m/z = 395.1692 $[M + H]^+$ |

Example 3: $IC_{50}$ Data

SARS-CoV-1/2 $3CL^{pro}$ Biochemical Assay. Protease activity and subsequent 10-point $IC_{50}$ curves were spectroscopically determined using a scaled down, endpoint assay adapted from a previously described peptide-based Forster Resonance Energy Transfer (FRET) assay (Jacobs et al. *J. Med. Chem.* 2013, 56 (2), 534-546; Tomar et al. *J. Biol. Chem.* 2015, 290 (32), 19403-19422). Compounds (as 10 mM DMSO stock) were serial diluted 4-fold using 100% DMSO in a LabCyte 384-well LDV plate and acoustically transferred using a LabCyte ECHO 550 into Corning 384-well black NBS plates. Standard 10-point $IC_{50}$ 384-well plate layout is as follows: 100 μM of 2-(1H-benzo[d][1,2,3]triazol-1-yl)-N-(4-(pyridin-3-yl)phenyl)-N-(thiophen-3-ylmethyl)acetamide was stamped into columns 1 and 24 (low control), DMSO was stamped into columns 2 and 23 (high control), and serial diluted compounds were stamped from high (100 μM) to low (0.38 nM) concentrations in columns 3-12 (replicate 1) and 13-22 (replicate 2). Protocol for running the assay is as follows: assay wells stamped with 0.25 μL of compound or DMSO were filled via a ThermoFisher Multidrop Combi liquid dispenser with 14.5 μL of 150 nM or 200 nM (concentration for 25 μL final reaction volume) of SARS-CoV-1 or SARS-CoV-2 $3CLPro^M$, respectively, in assay buffer (50 mM HEPES, 0.1 mg/ml BSA, 0.01% v/v TRITON X100, 2 mM DTT, pH 7.5). Assay plates were then centrifuged at 1,000 RPM (Eppendorf 5810R, S-4-104 rotor) for 1 minute, covered, and incubated at room temperature for 15 minutes. Reactions were initiated using the Multidrop Combi liquid dispenser to titrate 10 μL of 2 μM (concentration for 25 μL final reaction volume) of fluorophore-quencher peptide substrate (from AnaSpec, Inc. Catalog No. AS-65599) solubilized in assay buffer into each well. Assay plates were again centrifuged at 1,000 RPM for 1 minute, covered, and incubated at room temperature for 30 minutes. Biochemical assays were quenched through the addition of 5 μL of 500 mM acetic acid via Multidrop Combi liquid dispenser. Assay plates were then centrifuged at 1,000 RPM for 1 minute and resulting fluoresce intensity measured on a BioTek Cytation 5 multimode plate reader ($\lambda_{ex}$=485 nm, $\lambda_{em}$=528 nm).

Data analyses: Raw fluorescence values were normalized ($RF_{norm}$) by dividing each value by the average of DMSO control wells which represents the maximal fluorescence signal ($RF_{norm}$=$RF_{sample}$/Ave $RF_{DMSO\ control}$). Dose response curve fitting was performed using Dotmatics Studies (software version 5.4.2), which computes $IC_{50}$ values utilizing a four-parameter logistical fit. Reported values are average $IC_{50}$ from at least 3 independent experiments. Data are shown in Table 2. Data are also shown for a comparative compound ML300 (N-(4-(2-(1H-benzo[d][1,2,3]triazol-1-yl)-N-(thiophen-3-ylmethyl)acetamido)phenyl)cyclopropanecarboxamide; Turlington et al. *Bioorganic Med. Chem. Lett.* 2013, 23 (22), 6172-6177).

TABLE 2

| $IC_{50}$ Values | |
|---|---|
| Compound ID | SARS-CoV-2 $IC_{50}$ (nM) |
| 1 | 365 |
| 2 | 30 |
| 3 | 3365 |
| 4 | 1146 |
| 5 | 5217 |
| 6 | 5000 |
| 7 | Inactive |
| 8 | Inactive |
| 9 | 71 |
| 10 | 77 |
| 11 | 65 |
| 12 | 15 |
| 13 | 587 |
| 14 | 76 |
| 15 | 308 |
| 16 | 370 |
| 17 | 101 |
| 18 | 191 |
| 19 | 100 |
| 20 | ND |
| 21 | ND |
| 22 | 786 |
| 23 | 159 |
| 24 | 1297 |
| 25 | 184 |
| 26 | 351 |
| 27 | 209 |
| 28 | 53 |
| 29 | 40 |
| 30 | 114 |
| 31 | 506 |
| 32 | ND |
| 33 | ND |
| 34 | ND |
| 35 | 481 |

TABLE 2-continued

| IC$_{50}$ Values | |
|---|---|
| Compound ID | SARS-CoV-2 IC$_{50}$ (nM) |
| 36 | 370 |
| 37 | ND |
| 38 | 1249 |
| 39 | 82 |
| 40 | 53 |
| 41 | 604 |
| 42 | 250 |
| 43 | 188 |
| 44 | 414 |
| 45 | 356 |
| 46 | 8099 |
| 47 | 621 |
| 48 | 542 |
| 49 | 839 |
| 50 | 30840 |
| 51 | 100 |
| 52 | 389 |
| 53 | 179 |
| 54 | 90 |
| 55 | 2038 |
| 56 | 139 |
| 57 | 81 |
| 58 | 1087 |
| 59 | 6235 |
| 60 | 193 |
| 61 | 113 |
| 62 | 69 |
| 63 | 1027 |
| 64 | 231 |
| 65 | 187 |
| 66 | 103 |
| 67 | 161 |
| 68 | 608 |
| 69 | 220 |
| 70 | 84 |
| 71 | 115 |
| 72 | 56 |
| 73 | 61 |
| 74 | 76 |
| 75 | 1001 |
| 76 | 311 |
| 77 | 136 |
| 78 | 222 |
| 79 | 112 |
| 80 | 110 |
| 81 | 1309 |
| 82 | 70 |
| 83 | 5225 |

Example 4: Virus Inhibition Assays

Initial antiviral screening will be done by using CPE inhibition assay (Shin et al. *Chemotherapy* 2016, 61 (3), 159-166). Briefly, Vero E6 ACE2 cells will be cultured in a 96-well flat-bottom plates at a density of $2\times10^4$ cells per well. Following infection of the cells with a 100 TCID$_{50}$ of SARS-CoV-2, the plates will be incubated on a rocker in 37° C. for 45 min for virus adsorption. The cells will then be washed with DMEM and the medium containing the test compounds in the desired concentration will be added. Both the uninfected cells and infected cells treated with 10 μM of Remdesivir will be used as controls. The antiviral efficacy of test compounds will be determined by the uptake and subsequent extraction of neutral red dye. After infection (68 h), cells will be incubated with 0.034% neutral red dye for 3 h at 37° C. Free dye will be washed from the wells and the uptake dye was quantified using a microplate reader with absorbance at 540 nm. Absorbance values will be expressed as percentages of uninfected control cells, and EC$_{50}$ values of the test compounds will be determined using Prism software (GraphPad).

Compound 12 was tested in a plaque reduction assay as described above (protocol slightly modified from Shin 2018). The EC$_{50}$ was 1.14 μM.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and “at least one” and similar referents in the context of describing the invention (especially in the context of the following claims) are to be construed to cover both the singular and the plural, unless otherwise indicated herein or clearly contradicted by context. The use of the term “at least one” followed by a list of one or more items (for example, “at least one of A and B”) is to be construed to mean one item selected from the listed items (A or B) or any combination of two or more of the listed items (A and B), unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

(I)

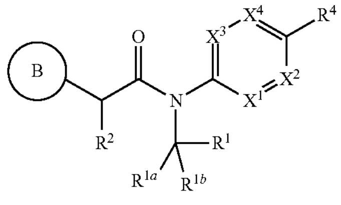

or a pharmaceutically acceptable salt thereof, wherein:

$R^1$ is selected from: (i) aryl, which is substituted with 1 or 2 substituents independently selected from halo, $C_1$-$C_3$ alkyl, $C_1$-$C_3$ alkoxy, $C_1$-$C_3$ hydroxyalkyl, $C_1$-$C_3$ haloalkyl, $C_1$-$C_3$ haloalkoxy, and cyano; and (ii) a monocyclic 6-membered heteroaryl having 1 or 2 nitrogen atoms, which is substituted with 1 or 2 substituents independently selected from halo, $C_1$-$C_3$ alkyl, $C_1$-$C_3$ alkoxy, $C_1$-$C_3$ hydroxyalkyl, $C_1$-$C_3$ haloalkyl, $C_1$-$C_3$ haloalkoxy, and cyano;

$R^{1a}$ and $R^{1b}$ are each independently selected from hydrogen and $C_1$-$C_3$ alkyl;

B is a monocyclic heteroaryl, bicyclic heteroaryl, or a bicyclic heterocyclyl, wherein B is linked to the remainder of the molecule via a carbon atom, and wherein the monocyclic heteroaryl, bicyclic heteroaryl, and bicyclic heterocyclyl are independently unsubstituted or substituted with 1, 2, or 3 substituents independently selected from $C_1$-$C_3$ alkyl, $C_1$-$C_3$ alkoxy, $C_1$-$C_3$ hydroxyalkyl, halo, $C_1$-$C_3$ haloalkyl, $C_1$-$C_3$ haloalkoxy, $C_3$-$C_6$ cycloalkyl, aryl, arylalkyl, amino, hydroxy, cyano, oxo, and thioxo;

$R^2$ is hydrogen or $C_1$-$C_3$ alkyl;

$X^1$ is $CR^{3a}$ or N, $X^2$ is $CR^{3b}$ or N, $X^3$ is $CR^{3c}$ or N, and $X^4$ is $CR^{3d}$ or N;

$R^{3a}$, $R^{3b}$, $R^{3c}$, and $R^{3d}$ are each independently selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, wherein $R^{3e}$, $R^{3f}$, $R^{3g}$, and $R^{3h}$ are each independently selected from hydrogen and $C_1$-$C_3$ alkyl, wherein n3 is 0, 1, or 2, and wherein $G^3$ is selected from $C_3$-$C_6$ cycloalkyl and a 4- to 6-membered monocyclic heterocycle;

$R^4$ is selected from: a 5-membered monocyclic heteroaryl having 1, 2, 3, or 4 heteroatoms independently selected from N, O, and S; a 5- or 6-membered heterocyclyl having 1, 2, or 3 heteroatoms independently selected from N, O, and S; cyano; —$CR^{4c}R^{4d}$—$NR^{4a}R^{4b}$; and —$C(O)NR^{4a}R^{4b}$; wherein the heteroaryl and heterocyclyl are independently unsubstituted or substituted with 1, 2, or 3 substituents independently selected from $C_1$-$C_3$ alkyl, $C_1$-$C_3$ alkoxy, $C_1$-$C_3$ hydroxyalkyl, halo, $C_1$-$C_3$ haloalkyl, $C_1$-$C_3$ haloalkoxy, $C_3$-$C_6$ cycloalkyl, aryl, arylalkyl, amino, hydroxy, cyano, oxo, and thioxo;

$R^{4a}$ and $R^{4b}$ are each independently selected from hydrogen and $C_1$-$C_3$ alkyl; and $R^{4c}$ and $R^{4d}$ are each independently selected from hydrogen, $C_1$-$C_3$ alkyl, $C_1$-$C_3$ haloalkyl, and $C_3$-$C_6$ cycloalkyl, or $R^{4c}$ and $R^{4d}$, together with the carbon atom to which they are attached, are taken together to form a 3- to 6-membered ring.

2. The compound of claim 1, or a pharmaceutically acceptable salt thereof, wherein $R^1$ is phenyl or pyridyl, each of which is substituted with 1 or 2 substituents independently selected from halo, $C_1$-$C_3$ alkyl, $C_1$-$C_3$ haloalkyl, $C_1$-$C_3$ haloalkoxy, and $C_1$-$C_3$ alkoxy.

3. The compound of claim 1, or a pharmaceutically acceptable salt thereof, wherein $R^1$ is selected from:

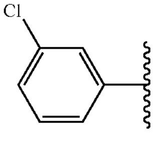,
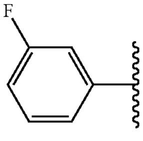,
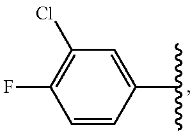,

-continued

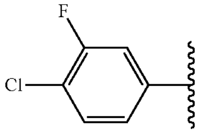,
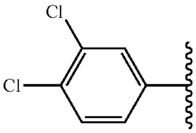,
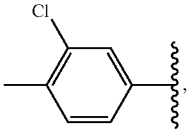,
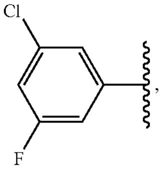,
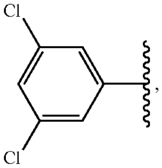,
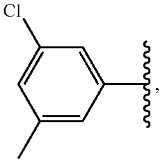,
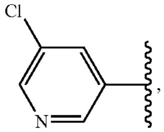,
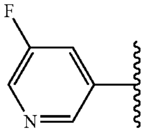,
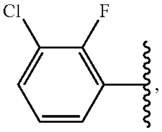,
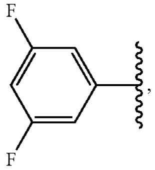,
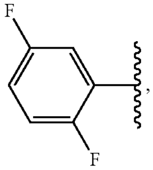,
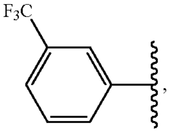,
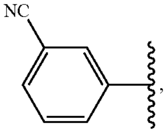,
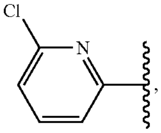,
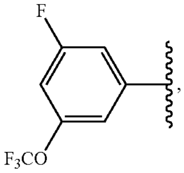,
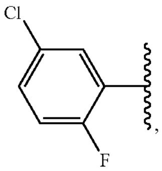,
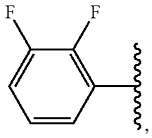,
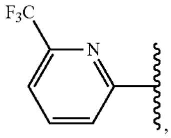,
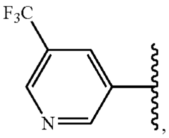,
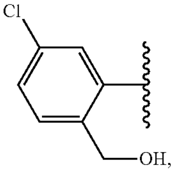,
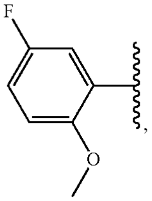,
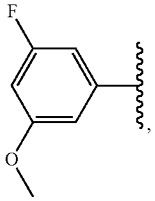,
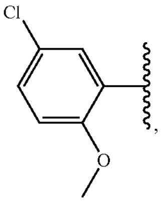
and
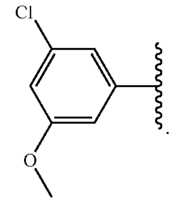.

4. The compound of claim 1, or a pharmaceutically acceptable salt thereof, wherein $R^{1a}$ is hydrogen and $R^{1b}$ is hydrogen.

5. The compound of claim 1, or a pharmaceutically acceptable salt thereof, wherein B is selected from: a five-membered heteroaryl having 1, 2, 3, or 4 heteroatoms independently selected from N, O, and S; a six-membered heteroaryl having 1, 2, 3, or 4 nitrogen atoms; an 8-10 membered bicyclic heteroaryl having 1, 2, 3, or 4 heteroatoms independently selected from N, O, and S; and an 8-10 membered bicyclic heterocyclyl having 1, 2, 3, or 4 heteroatoms independently selected from N, O, and S.

6. The compound of claim 1, or a pharmaceutically acceptable salt thereof, wherein B is selected from pyridyl, pyridazinyl, pyrimidinyl, pyrazinyl, pyrrolyl, pyrazolyl, imidazolyl, triazolyl, tetrazolyl, oxazolyl, thiazolyl, oxadiazolyl, thiadiazolyl, quinolinyl, isoquinolinyl, phthalazinyl, imidazopyridinyl, benzoisoxazolyl, benzoisothiazolyl, triazolopyridinyl, and isoindolinyl, wherein B is unsubstituted or substituted with 1 or 2 substituents independently selected from methyl, fluoro, chloro, bromo, trifluoromethyl, methoxy, cyclopropyl, oxo, and phenyl.

7. The compound of claim 1, or a pharmaceutically acceptable salt thereof, wherein B is selected from:

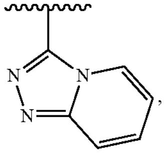, 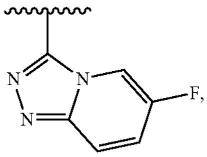, 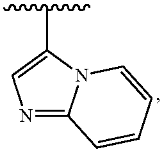,

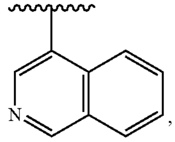, 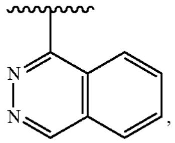, 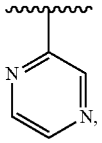

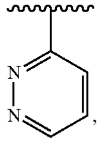, 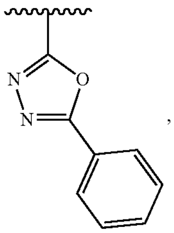, 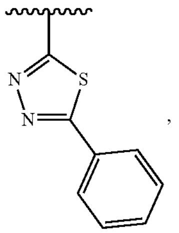,

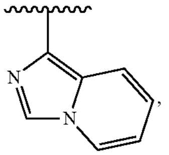, 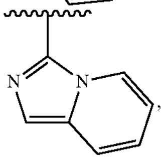, 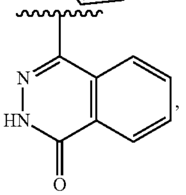,

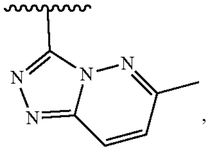, 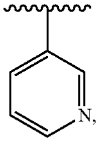 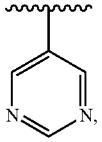

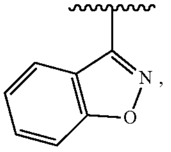, 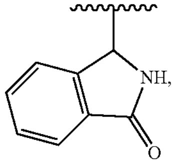 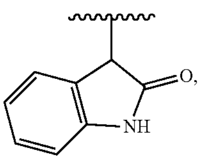

-continued

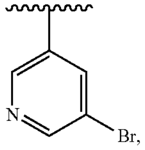 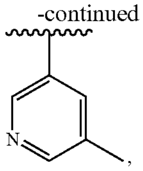, 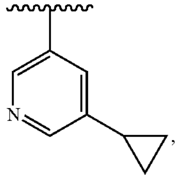,

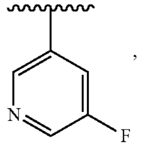, 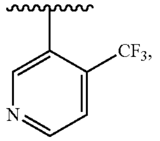 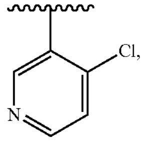

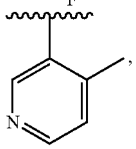, and 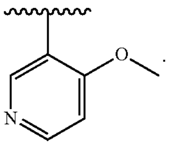.

8. The compound of claim 1, or a pharmaceutically acceptable salt thereof, wherein $R^2$ is hydrogen.

9. The compound of claim 1, or a pharmaceutically acceptable salt thereof, wherein $X^1$ is $CR^{3a}$, $X^2$ is $CR^{3b}$, $X^3$ is $CR^{3c}$, and $X^4$ is $CR^{3d}$ and one of $R^{3a}$, $R^{3b}$, $R^{3c}$, and $R^{3d}$ is selected from hydrogen, $C_1$-$C_3$ alkyl, $C_1$-$C_3$ alkoxy, halo, $C_1$-$C_3$ haloalkyl, $C_1$-$C_3$ haloalkoxy, $C_1$-$C_3$ hydroxyalkyl, cyano, —$OR^{3e}$, —$COOR^{3f}$, —$CON(R^{3g})(R^{3h})$, and —$(CH_2)_{n3}$-$G^3$, and the remaining three of $R^{3a}$, $R^{3b}$, $R^{3c}$, and $R^{3d}$ are hydrogen.

10. The compound of claim 1, or a pharmaceutically acceptable salt thereof, wherein $R^4$ is selected from: a 5-membered monocyclic heteroaryl having 1, 2, 3, or 4 nitrogen atoms, which is unsubstituted or substituted with 1 or 2 substituents independently selected from $C_1$-$C_3$ alkyl; a 5- or 6-membered heterocyclyl having 1, 2, or 3 heteroatoms independently selected from N and O, which is unsubstituted or substituted with 1 or 2 substituents independently selected from oxo and thioxo; cyano; —$CR^{4c}R^{4d}$—$NR^{4a}R^{4b}$; and —$C(O)NR^{4a}R^{4b}$; wherein $R^{4a}$ and $R^{4b}$ are each independently selected from hydrogen and methyl, and $R^{4c}$ and $R^{4d}$ are each independently selected from hydrogen, methyl, and halomethyl.

11. The compound of claim 1, or a pharmaceutically acceptable salt thereof, wherein $R^4$ is a 5-membered monocyclic heteroaryl selected from pyrazolyl, imidazolyl, triazolyl, and tetrazolyl, each of which is independently unsubstituted or substituted with one substituent selected from $C_1$-$C_3$ alkyl.

12. The compound of claim 1, or a pharmaceutically acceptable salt thereof, wherein $R^4$ is a 5- or 6-membered heterocyclyl selected from pyrrolidinyl, piperidinyl, dihydropyrrolyl, dihydrotriazolyl, dihydrooxadiazolyl, and dihydropyridinyl, each of which is independently unsubstituted or substituted with one substituent selected from oxo and thioxo.

13. The compound of claim 1, or a pharmaceutically acceptable salt thereof, wherein $R^4$ is selected from:

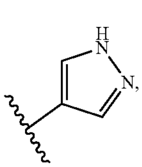 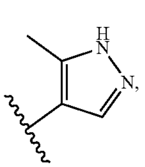 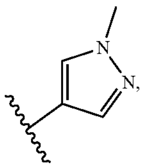

-continued
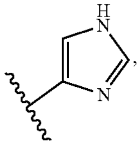 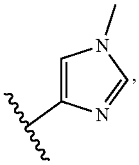 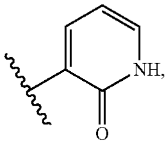
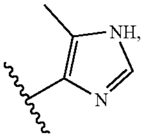 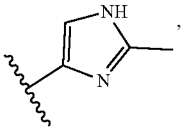 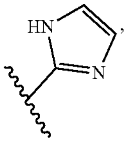
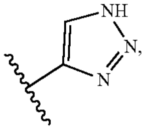 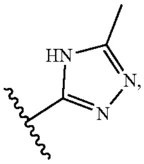 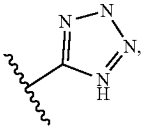
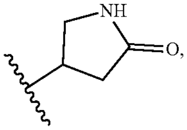 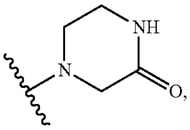 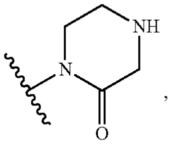
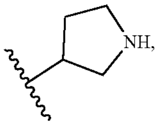 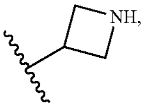 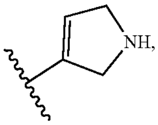
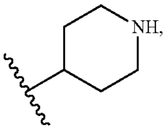 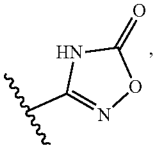 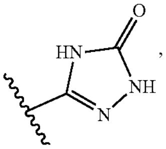
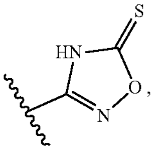 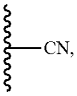 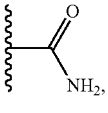
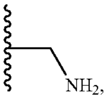 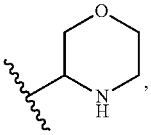
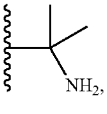 and 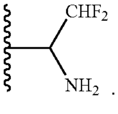.
14. A compound selected from:
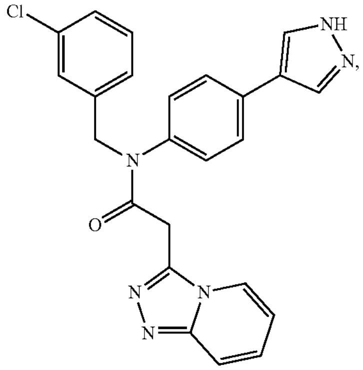
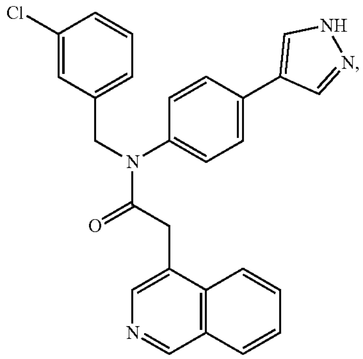
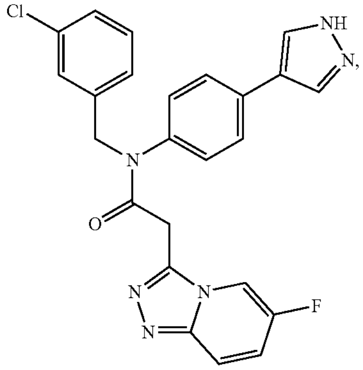
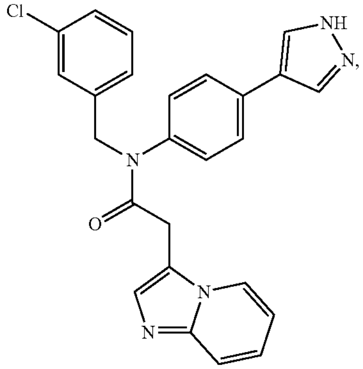

-continued
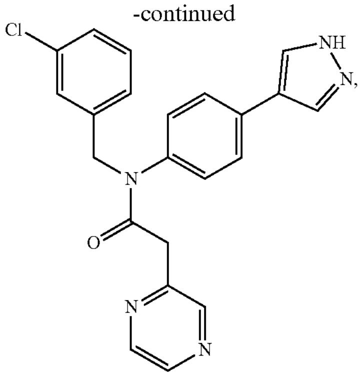
,
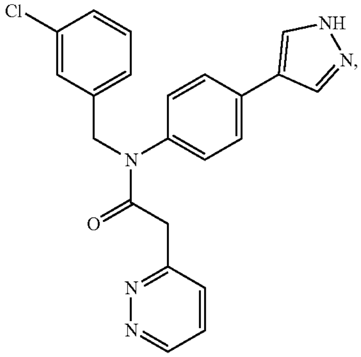
,
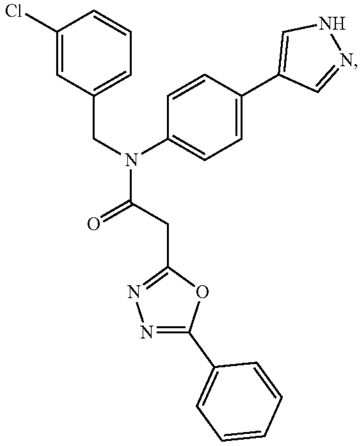
,
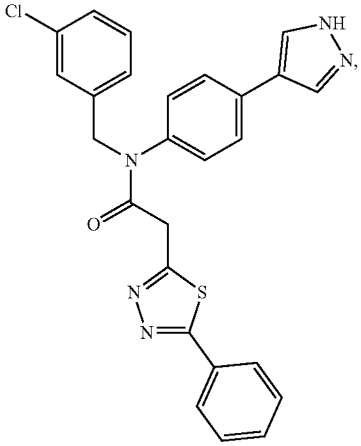
,
-continued
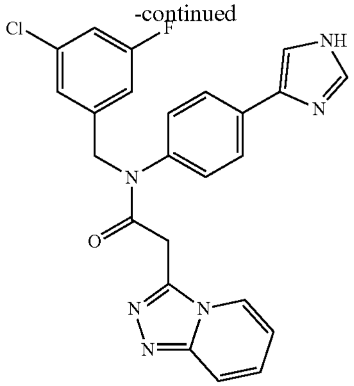
,
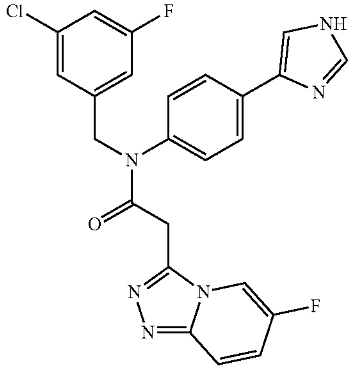
,
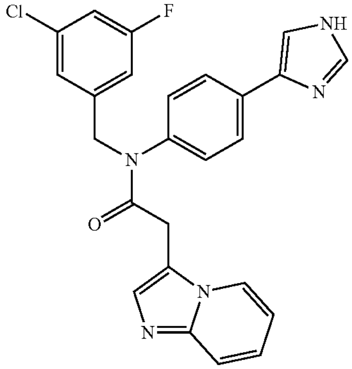
,
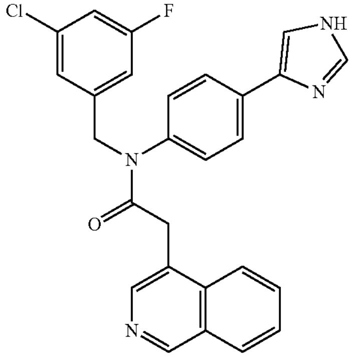
, -continued
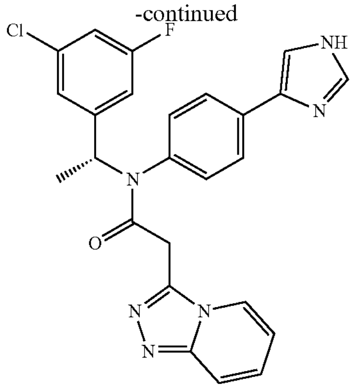
,
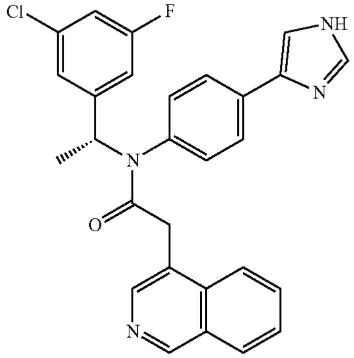
,
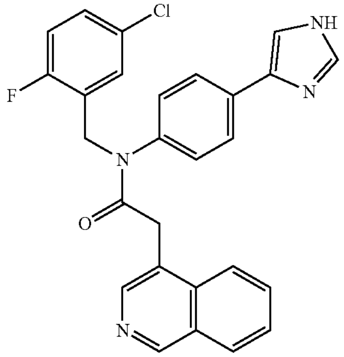
,
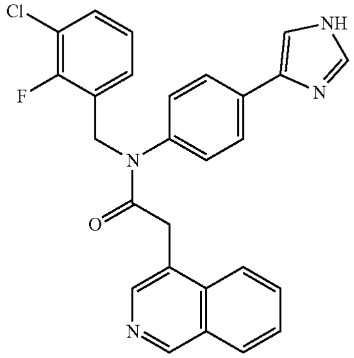
,
-continued
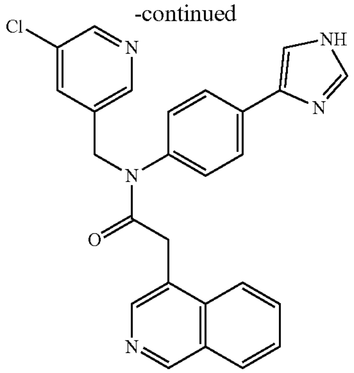
,
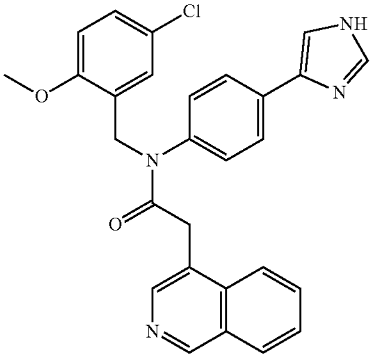
,
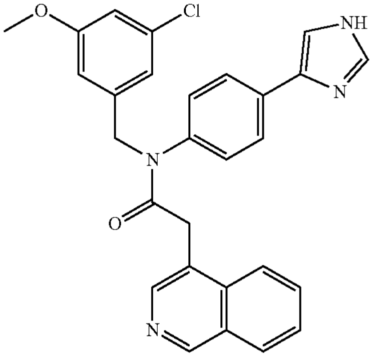
,
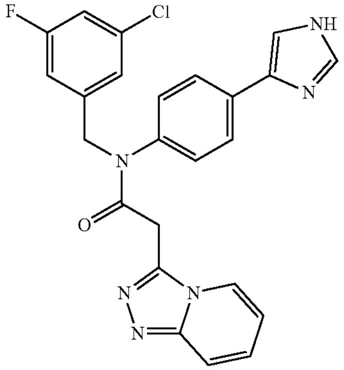
, -continued
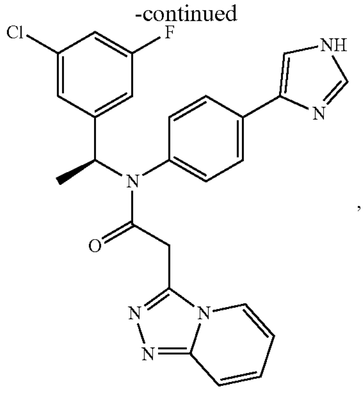
,
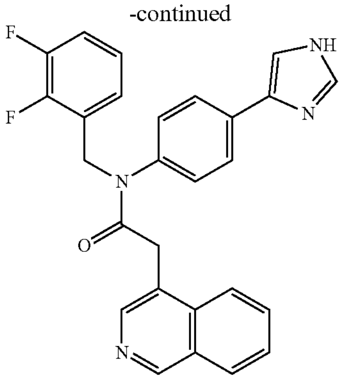
,
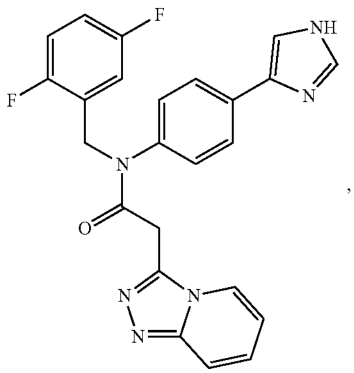
,
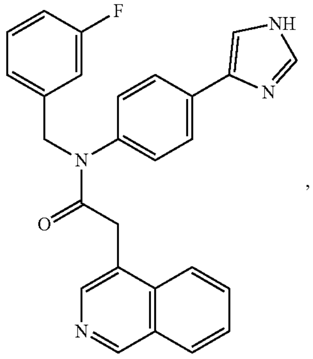
,
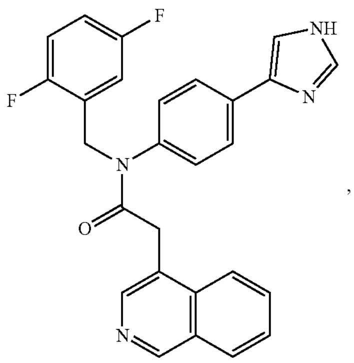
,
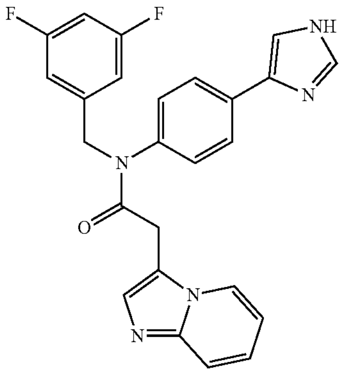
,
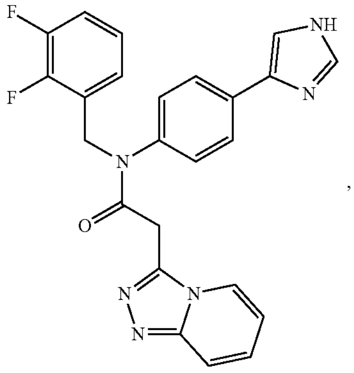
,
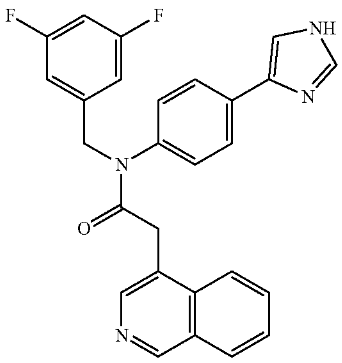
, -continued
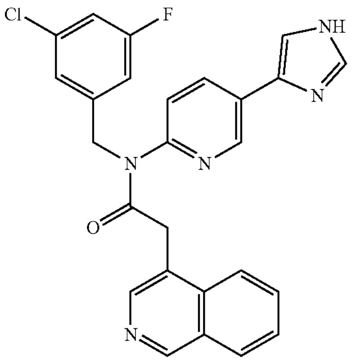
,
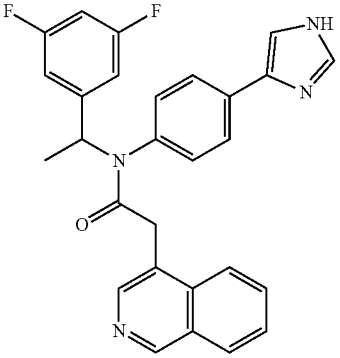
,
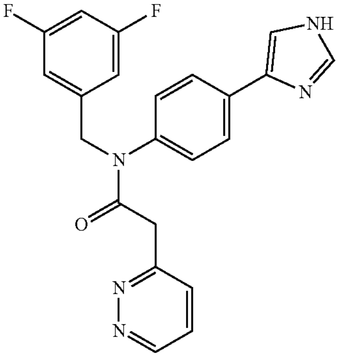
,
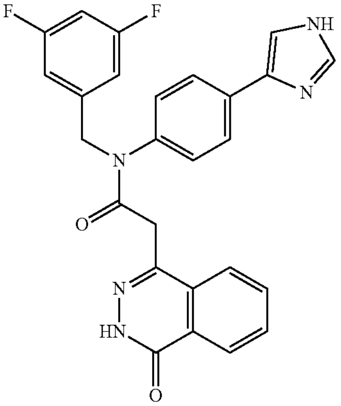
,
-continued
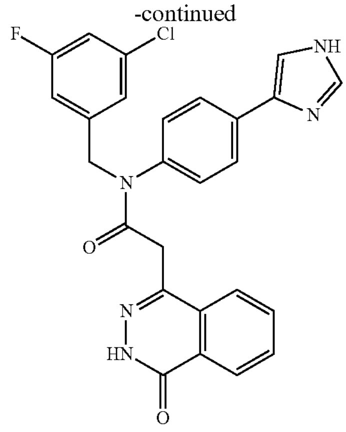
,
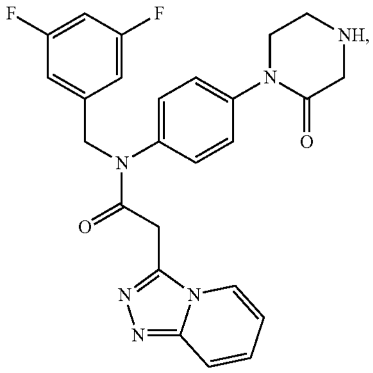
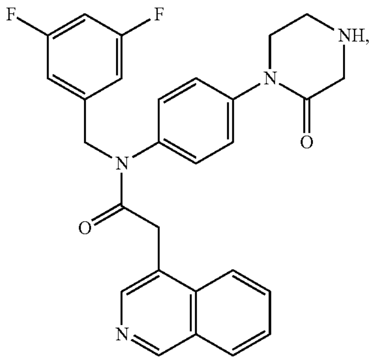
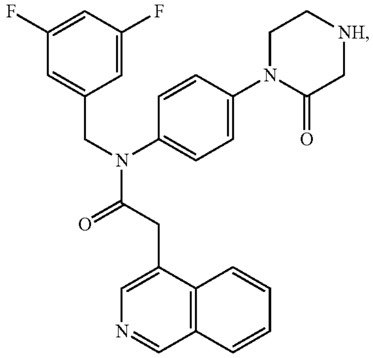

-continued
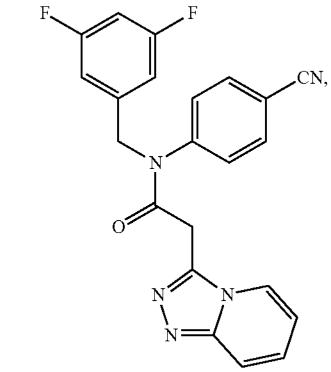
,
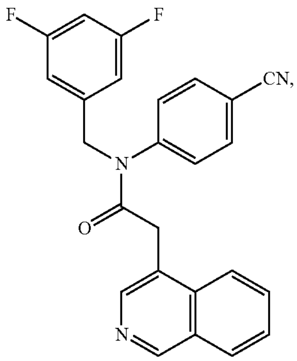
,
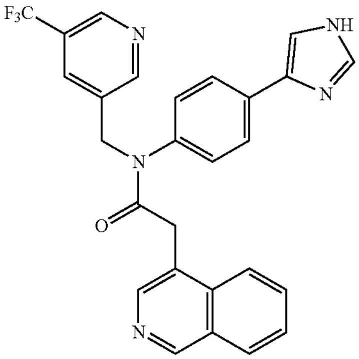
,
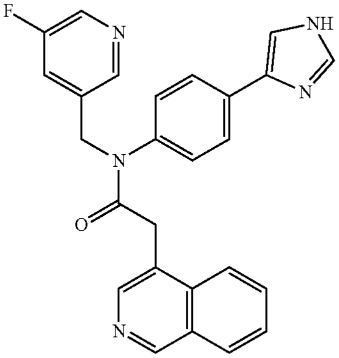
,
-continued
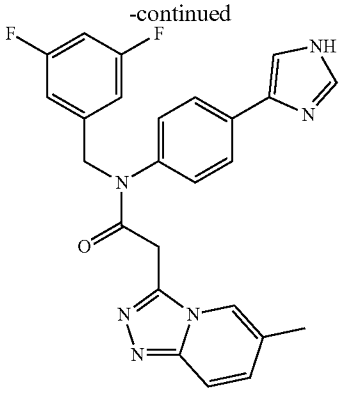
,
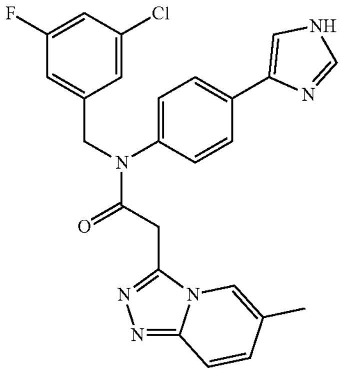
,
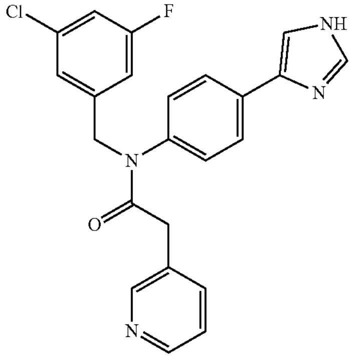
,
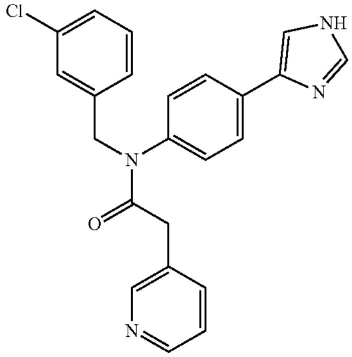
, -continued
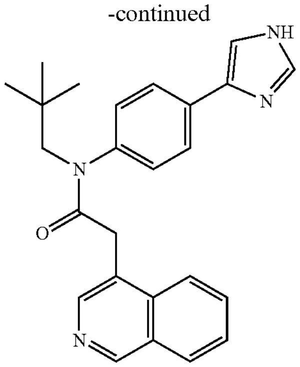
,
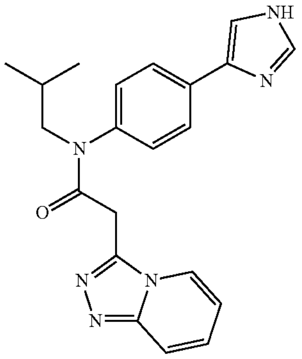
,
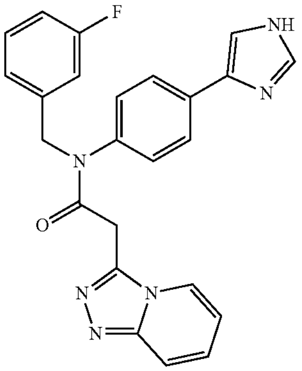
,
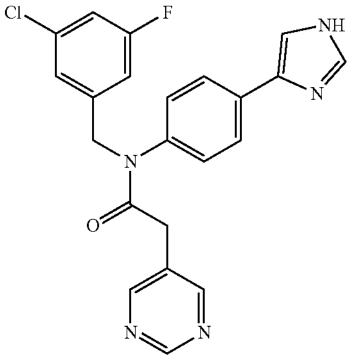
,
-continued
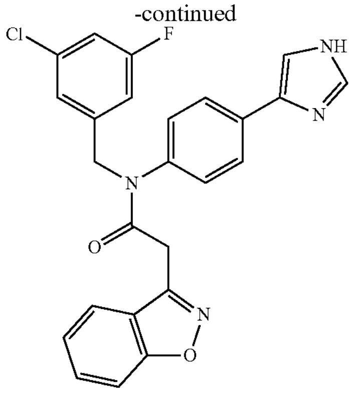
,
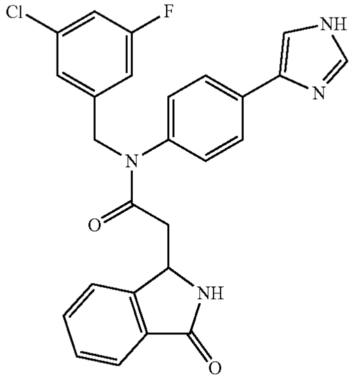
,
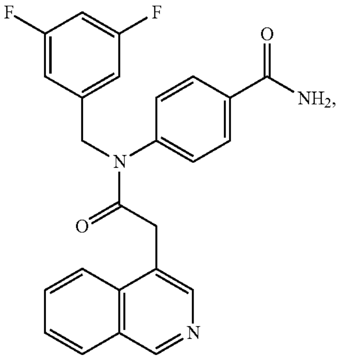
,
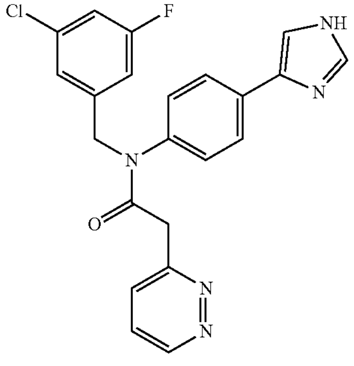
, -continued
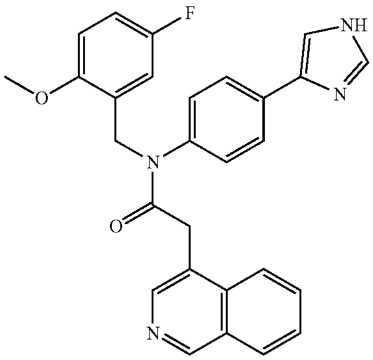
,
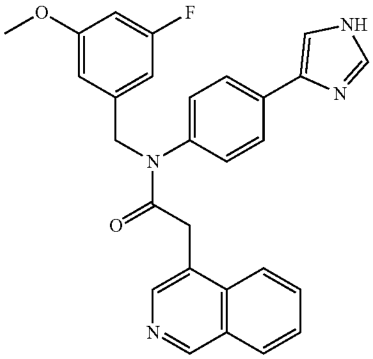
,
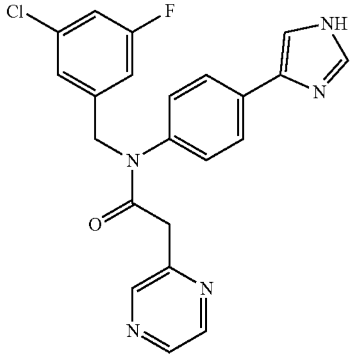
,
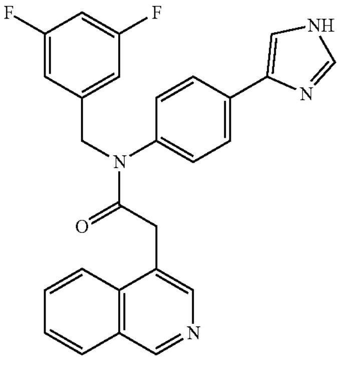
,
-continued
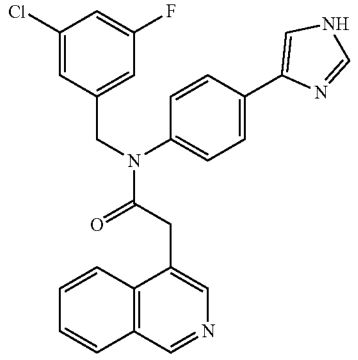
,
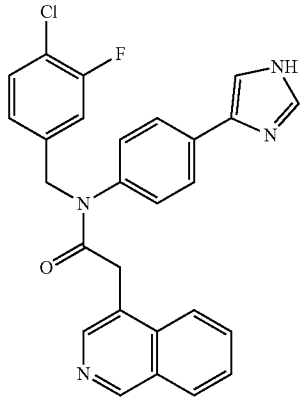
,
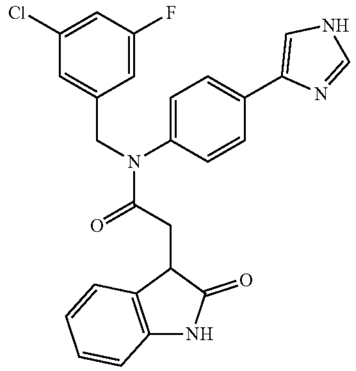
,
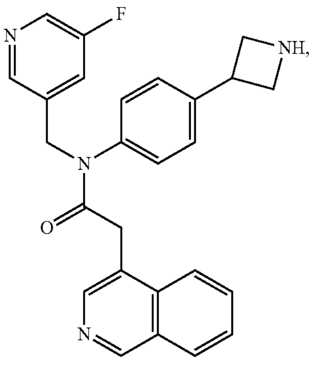

-continued
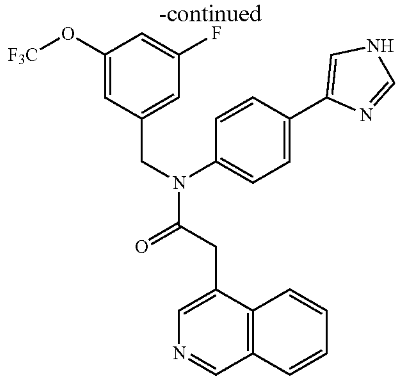
,
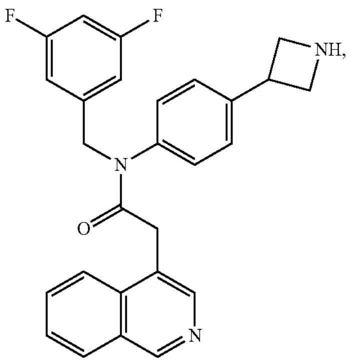
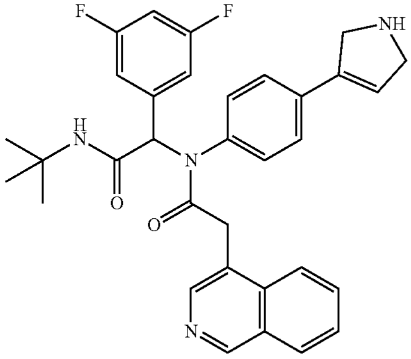
,
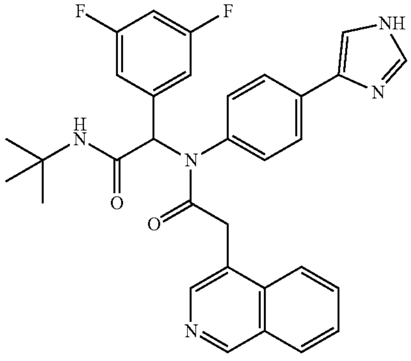
,
-continued
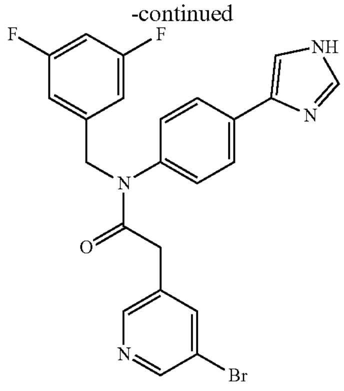
,
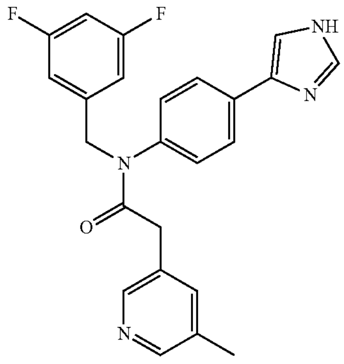
,
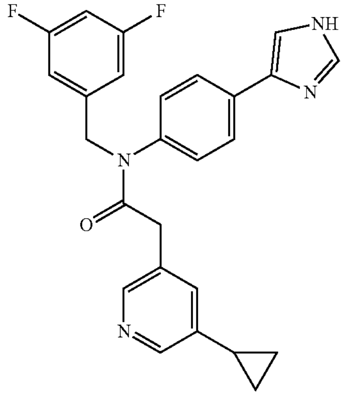
,
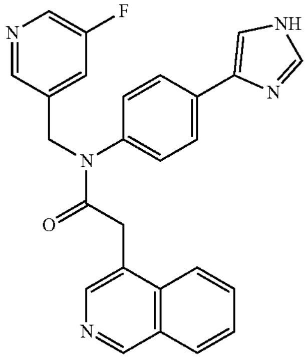
, -continued
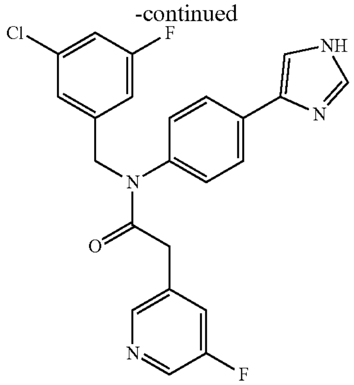
,
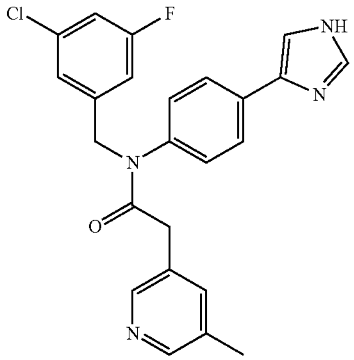
,
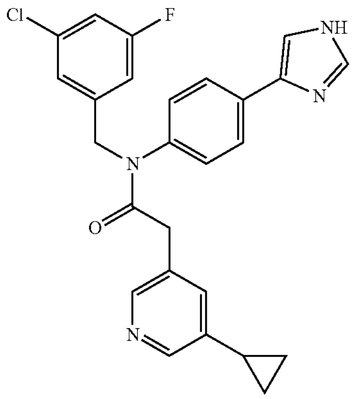
,
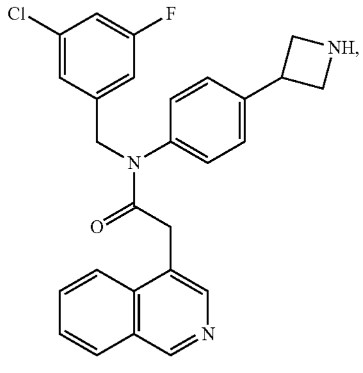
-continued
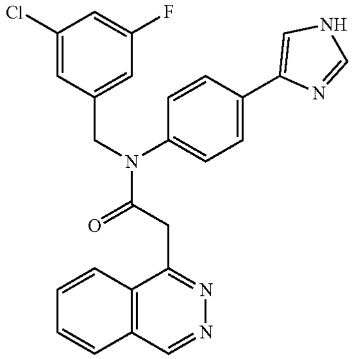
,
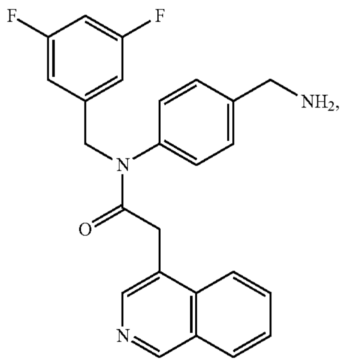
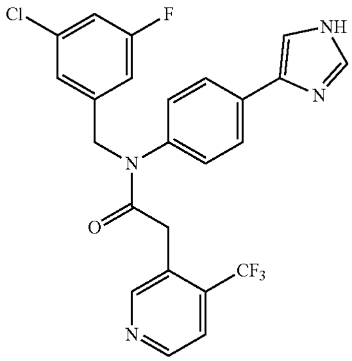
,
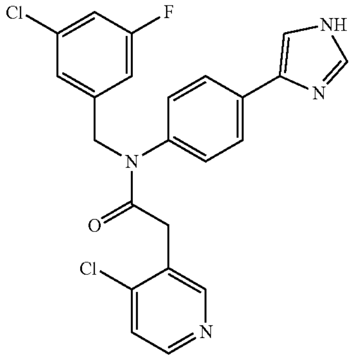
, -continued

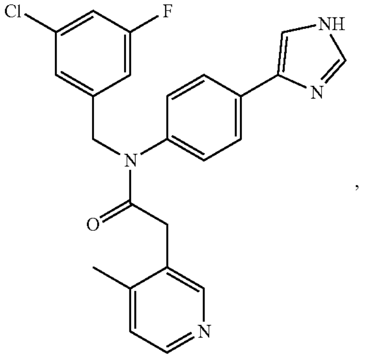

,

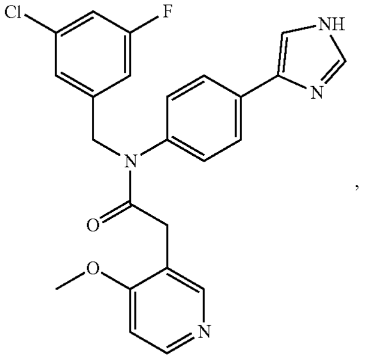

,

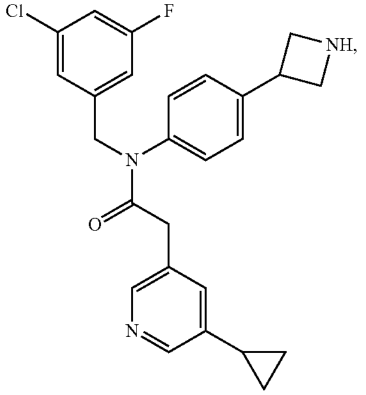

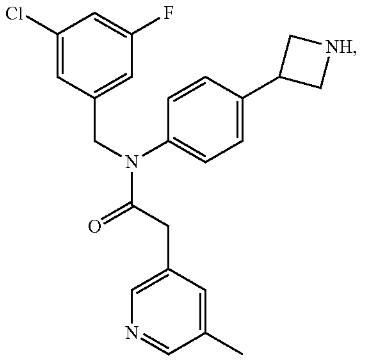

-continued

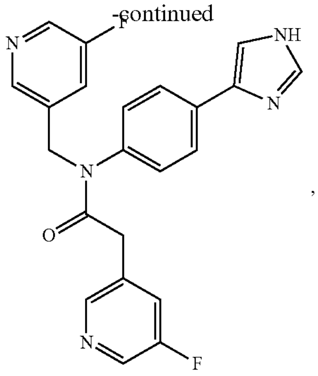

,

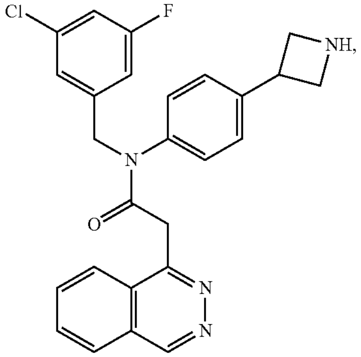

and

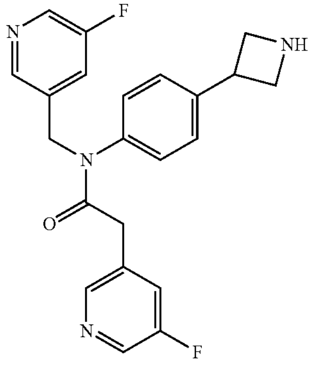

and pharmaceutically acceptable salts thereof.

15. A pharmaceutical composition comprising a compound of claim 1, or a pharmaceutically acceptable salt thereof, and a pharmaceutically acceptable carrier.

16. A method of treating a viral infection in a subject in need thereof, comprising administering to the subject a therapeutically effective amount of a compound of claim 1, or a pharmaceutically acceptable salt thereof.

17. A method of inhibiting viral replication in a sample, comprising contacting the sample with a compound of claim 1, or a pharmaceutically acceptable salt thereof, in an amount effective to inhibit viral replication.

18. The method of claim 16, wherein the viral infection is a coronavirus infection.

19. The method of claim 18, wherein the coronavirus infection is a SARS-CoV-2 infection.

* * * * *